(12) United States Patent
Onoda et al.

(10) Patent No.: US 8,439,826 B2
(45) Date of Patent: May 14, 2013

(54) MEDICAL INSTRUMENT HAVING A DISPLAY UNIT THAT DISPLAYS A SHAPE OF AN INSERTION BODY INSERTED INTO AN INTERIOR OF AN OBJECT TO BE EXAMINED

(75) Inventors: Fumiyuki Onoda, Tama (JP); Hiroyuki Ushifusa, Tama (JP); Tomohiko Oda, Kawagoe (JP); Jun Hasegawa, Hino (JP); Masami Fukuchi, Hachioji (JP); Katsumi Hirakawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 92 days.

(21) Appl. No.: 12/847,223

(22) Filed: Jul. 30, 2010

(65) Prior Publication Data

US 2011/0098533 A1    Apr. 28, 2011

Related U.S. Application Data

(63) Continuation of application No. PCT/JP2009/068529, filed on Oct. 28, 2009.

(30) Foreign Application Priority Data

| Oct. 28, 2008 | (JP) | 2008-277086 |
| Oct. 28, 2008 | (JP) | 2008-277087 |
| Oct. 28, 2008 | (JP) | 2008-277089 |
| Oct. 28, 2008 | (JP) | 2008-277090 |
| Oct. 28, 2008 | (JP) | 2008-277091 |

(51) Int. Cl.
*A61B 1/00*     (2006.01)
*A61B 1/005*    (2006.01)

(52) U.S. Cl.
USPC ........................................ 600/117; 600/182

(58) Field of Classification Search .................. 600/103, 600/117, 146, 182, 424
See application file for complete search history.

(56) References Cited

U.S. PATENT DOCUMENTS 5,876,325 A * 3/1999 Mizuno et al. ................ 600/102
5,957,833 A * 9/1999 Shan ............................. 600/117

(Continued)

FOREIGN PATENT DOCUMENTS

| EP | 1 635 034 A1 | 3/2006 |
| JP | 06-261858 | 9/1994 |

(Continued)

OTHER PUBLICATIONS

Abstract of WO 01/33165 A1 dated May 10, 2001 corresponding to JP 2003-51504.
International Search Report dated Feb. 2, 2010.

*Primary Examiner* — John P Leubecker
(74) *Attorney, Agent, or Firm* — Scully, Scott, Murphy & Presser, P.C.

(57) ABSTRACT

A medical instrument including a distortion detection probe disposed in an insertion portion to be inserted into the interior of an examinee provided with a plurality of FBG sensor sections that detect distortion of the insertion portion, a coordinate calculation section that calculates first three-dimensional coordinates of the respective FBG sensor sections according to a first three-dimensional coordinate system whose origin is a predetermined position based on the detection results of the FBG sensor sections, a coordinate system setting section that sets a second three-dimensional coordinate system based on the first three-dimensional coordinates of the respective FBG sensor sections, a coordinate transformation section that transforms the first three-dimensional coordinates of the respective FBG sensor sections into second three-dimensional coordinates according to the second three-dimensional coordinate system set by the coordinate system setting section and a shape display section that displays the shape of the insertion portion based on the second three-dimensional coordinates transformed by the coordinate transformation section.

10 Claims, 39 Drawing Sheets

U.S. PATENT DOCUMENTS

| | | | |
|---|---|---|---|
| 6,059,718 A | 5/2000 | Taniguchi et al. | |
| 6,203,493 B1* | 3/2001 | Ben-Haim | 600/117 |
| 6,470,205 B2* | 10/2002 | Bosselmann et al. | 600/424 |
| 6,773,393 B1 | 8/2004 | Taniguchi et al. | |
| 6,868,195 B2* | 3/2005 | Fujita | 385/12 |
| 7,440,661 B2* | 10/2008 | Kobayashi | 385/117 |
| 7,585,273 B2* | 9/2009 | Adler et al. | 600/117 |
| 7,824,328 B2* | 11/2010 | Gattani et al. | 600/117 |
| 2002/0183592 A1* | 12/2002 | Suzuki et al. | 600/145 |
| 2004/0116775 A1 | 6/2004 | Taniguchi et al. | |
| 2004/0165810 A1 | 8/2004 | Fujita | |
| 2004/0204645 A1* | 10/2004 | Saadat et al. | 600/424 |
| 2006/0045408 A1 | 3/2006 | Jones et al. | |
| 2007/0106116 A1* | 5/2007 | Sugimoto | 600/117 |
| 2007/0265503 A1* | 11/2007 | Schlesinger et al. | 600/182 |
| 2007/0270686 A1* | 11/2007 | Ritter et al. | 600/424 |
| 2008/0071143 A1* | 3/2008 | Gattani et al. | 600/117 |

FOREIGN PATENT DOCUMENTS

| | | |
|---|---|---|
| JP | 08-107875 A | 4/1996 |
| JP | 2000-079088 | 3/2000 |
| JP | 2001-046319 A | 2/2001 |
| JP | 2001-169998 A | 6/2001 |
| JP | 2003-51504 | 4/2003 |
| JP | 2004-000551 | 1/2004 |
| JP | 2004-251779 | 9/2004 |
| WO | WO 2006/021751 A1 | 3/2006 |

* cited by examiner

MEDICAL INSTRUMENT HAVING A DISPLAY UNIT THAT DISPLAYS A SHAPE OF AN INSERTION BODY INSERTED INTO AN INTERIOR OF AN OBJECT TO BE EXAMINED

CROSS REFERENCE TO RELATED APPLICATION

This application is a continuation application of PCT/JP2009/068529 filed on Oct. 28, 2009 and claims benefit of Japanese Applications No. 2008-277086 filed in Japan on Oct. 28, 2008, No. 2008-277087 filed in Japan on Oct. 28, 2008, No. 2008-277089 filed in Japan on Oct. 28, 2008, No. 2008-277090 filed in Japan on Oct. 28, 2008, No. 2008-277091 filed in Japan on Oct. 28, 2008, the entire contents of each of which are incorporated herein by their reference.

BACKGROUND OF THE INVENTION

1. Field of the Invention

The present invention relates to a medical instrument provided with an insertion body to be inserted into the interior of an object to be examined.

2. Description of the Related Art

As a method of calculating a shape of an insertion portion of an endoscope or the like to be inserted into the interior of an examinee, one using a magnetic field sensor as described in Japanese Patent Application Laid-Open Publication No. 2000-79088 is known. The method using a magnetic field sensor detects a magnetic field from a magnetic field generation coil disposed outside the body of the examinee using a plurality of magnetic field detection coils arranged in an insertion portion and thereby calculates relative positions of the respective magnetic field detection coil with respect to the magnetic field generation coil. Since the positions of the plurality of magnetic field detection coils, that is, the position of the insertion portion, are calculated with reference to the position of the magnetic field generation coil, even if the examinee changes his/her posture or the insertion portion moves, the shape of the insertion portion displayed on a display screen is relatively stable. However, the method using a magnetic field sensor requires the magnetic field generation coil to be installed outside the body of the examinee, which results in an increase in the scale of the system.

By contrast, Japanese Patent Application Laid-Open Publication No. 6-261858 and Japanese Patent Application Laid-Open Publication No. 2007-130151 disclose a method of calculating a shape of an insertion portion by placing a distortion sensor in an insertion portion. Furthermore, Japanese Patent Application Laid-Open Publication No. 2003-515104 and Japanese Patent Application Laid-Open Publication No. 2004-251779 disclose a method of calculating a shape of an insertion portion by detecting distortion of an insertion portion using an optical fiber Bragg grating (Fiber Bragg Grating: hereinafter referred to as "FBG") sensor.

The method of calculating a shape of an insertion portion based on distortion of the insertion portion does not require a magnetic field generation coil or the like to be installed outside the body of the examinee, and can thereby reduce the size of the system.

SUMMARY OF THE INVENTION

The medical instrument according to an embodiment of the present invention includes an insertion body to be inserted into an interior of an object to be examined, a distortion detection probe disposed in the insertion body in which a plurality of distortion detection sections for detecting distortion of the insertion body are formed, a coordinate calculation section that calculates first coordinates of the respective distortion detection sections using any one of the plurality of distortion detection sections as a reference point in a first coordinate system defined by a correlation between the reference point and the distortion detection sections, a reference coordinate system setting section that sets a second coordinate system having a reference point and axial directions different from those of the first coordinate system, a coordinate transformation section that transforms the first three-dimensional coordinates of the respective distortion detection sections to second three-dimensional coordinates in the second coordinate system set by the coordinate system setting section based on a relative positional relationship between the reference point set by the reference coordinate system setting section and the reference point set by the first coordinate system, and a display section that displays a shape of the insertion body based on the second coordinates transformed by the coordinate transformation section.

DETAILED DESCRIPTION OF THE PREFERRED EMBODIMENTS

First Embodiment

Hereinafter, a medical instrument 1 according to a first embodiment of the present invention will be described with reference to the accompanying drawings.

Figure 1:
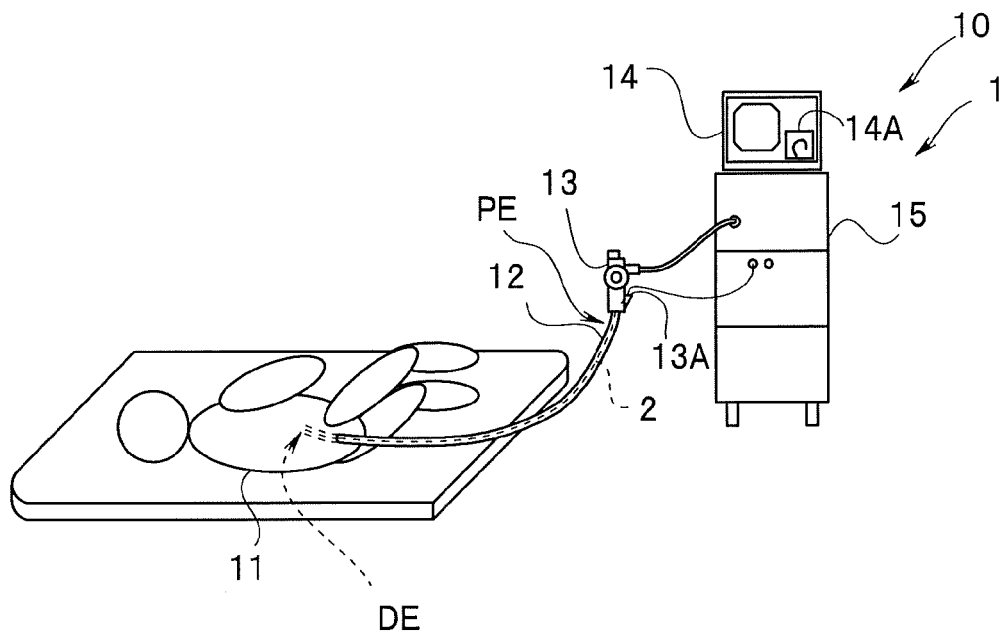
FIG. 1 is a diagram illustrating a situation in which a medical instrument according to a first embodiment is used.
Figure 2:
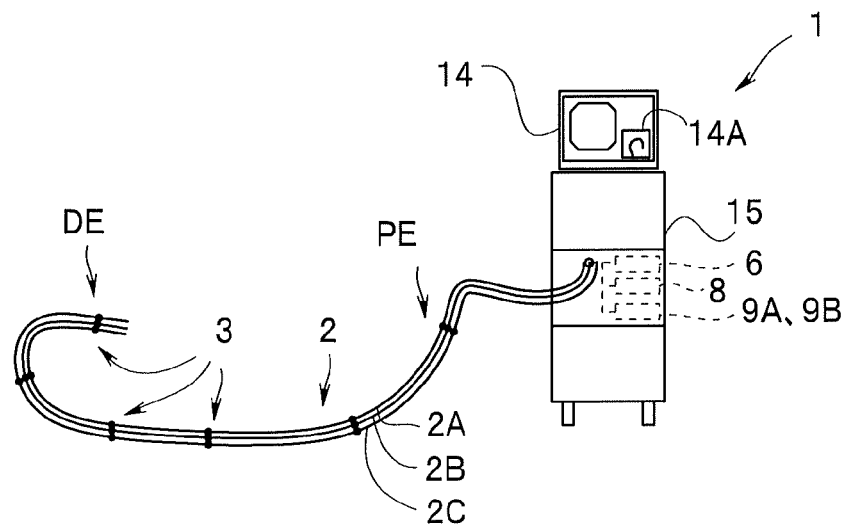
FIG. 2 is a diagram illustrating a configuration of the medical instrument according to the first embodiment.

FIG. 1 is a diagram illustrating a situation in which the medical instrument according to the present embodiment is used and FIG. 2 is a diagram illustrating a configuration of the medical instrument according to the present embodiment.

The medical instrument 1 according to the first embodiment shown in FIG. 1 measures the shape of an insertion portion 12 of an endoscope of an endoscope system 10 using an FBG sensor (see FIG. 2). The endoscope system 10 includes the insertion portion 12 of the endoscope which is a medical appliance inserted in the interior of an examinee 11 who is an object to be examined, for performing an observation or treatment and is an elongated insertion body, an operation portion 13 for operating the insertion portion 12, a main unit 15 that performs control over the entire endoscope system 10 and image processing or the like, and a monitor 14 that displays an endoscope image and a two-dimensional shape or the like of the insertion portion 12.

The optical fiber sensor 2 which is distortion detecting means of the medical instrument 1 is inserted from a treatment instrument hole 13A which is an opening disposed in the vicinity of the operation portion 13 on the proximal end portion PE (Proximal End) side of a channel that passes through the insertion portion 12 to the distal end portion DE (Distal End) side in a channel 12A (not shown) and is thereby deformed into the same shape as that of the insertion portion 12.

The optical fiber sensor 2 can be gently fixed to the insertion portion 12 as long as the shape of the insertion portion 12 matches the shape of the optical fiber sensor 2 to a degree that poses no practical problem. For example, the optical fiber sensor 2 may be gently fixed by inserting it into the channel as described above or the optical fiber sensor 2 may be incorporated in the insertion portion 12 beforehand.

The monitor 14 of the endoscope system 10 also serves as display means for the medical instrument 1 and the monitor 14 has a display region 14A for displaying the shape of the optical fiber sensor 2, that is, the shape of the insertion portion 12 on the same screen as that of the endoscope image. The optical fiber sensor 2 may be incorporated in the insertion portion 12 instead of being inserted into the channel 12A.

Figure 3A:
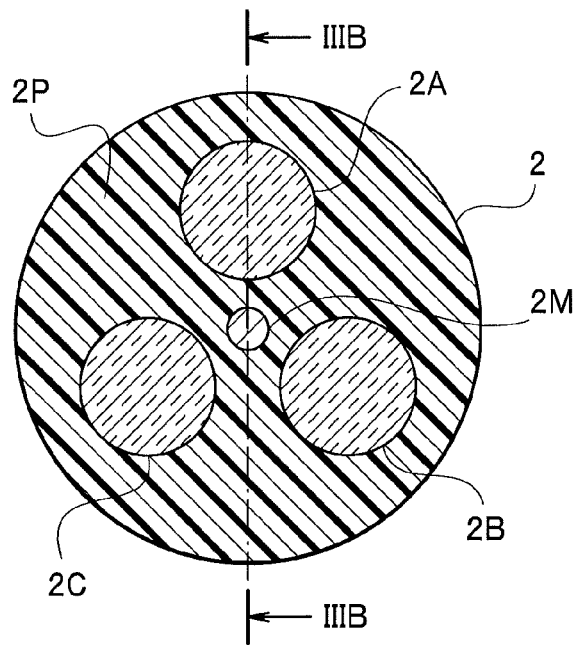
FIG. 3A is a configuration diagram illustrating a configuration of an optical fiber sensor of the medical instrument according to the first embodiment.
Figure 3B:
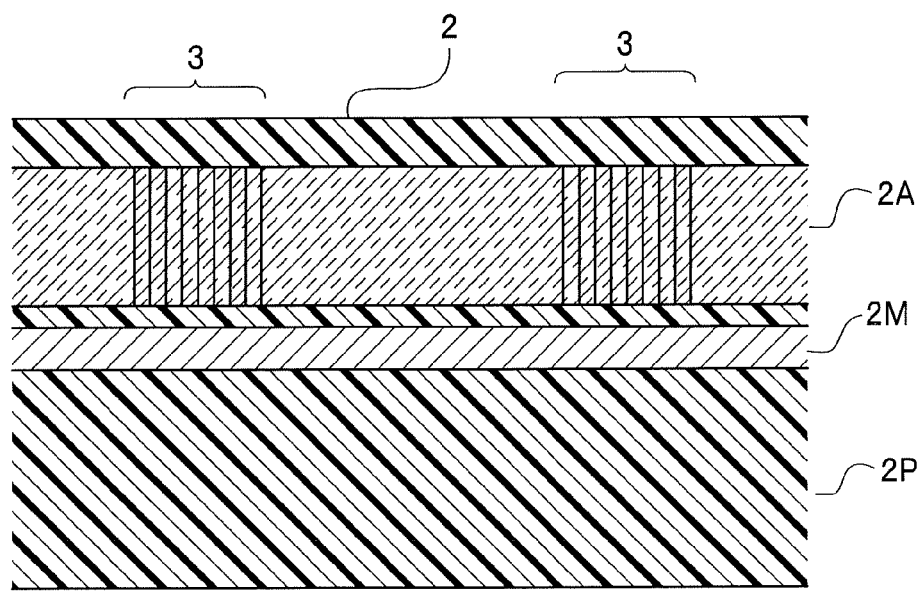
FIG. 3B is a cross-sectional view along the line IIIB-IIIB of FIG. 3A.
Figure 4:
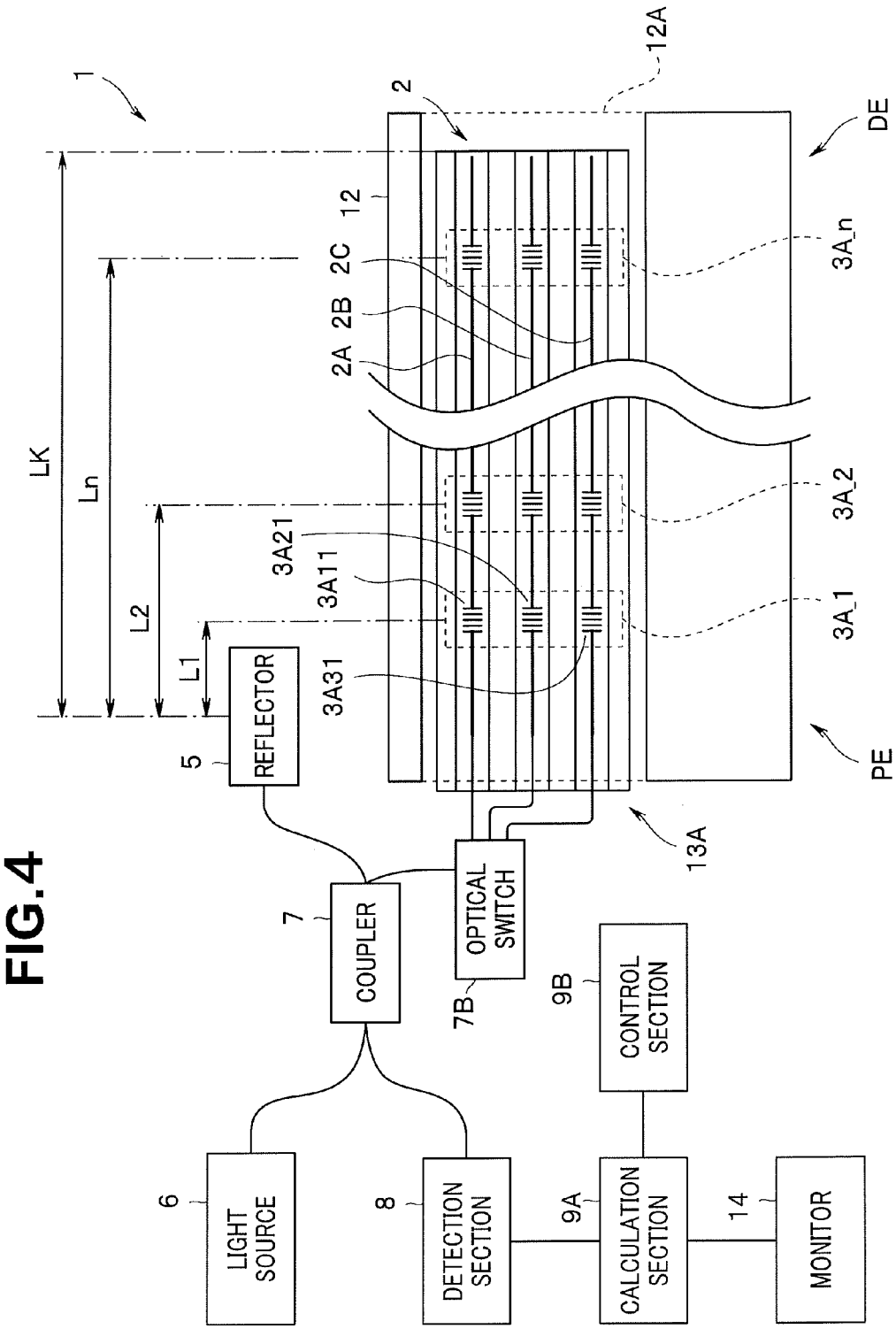
FIG. 4 is a diagram illustrating a configuration of the medical instrument according to the first embodiment.
Figure 5:
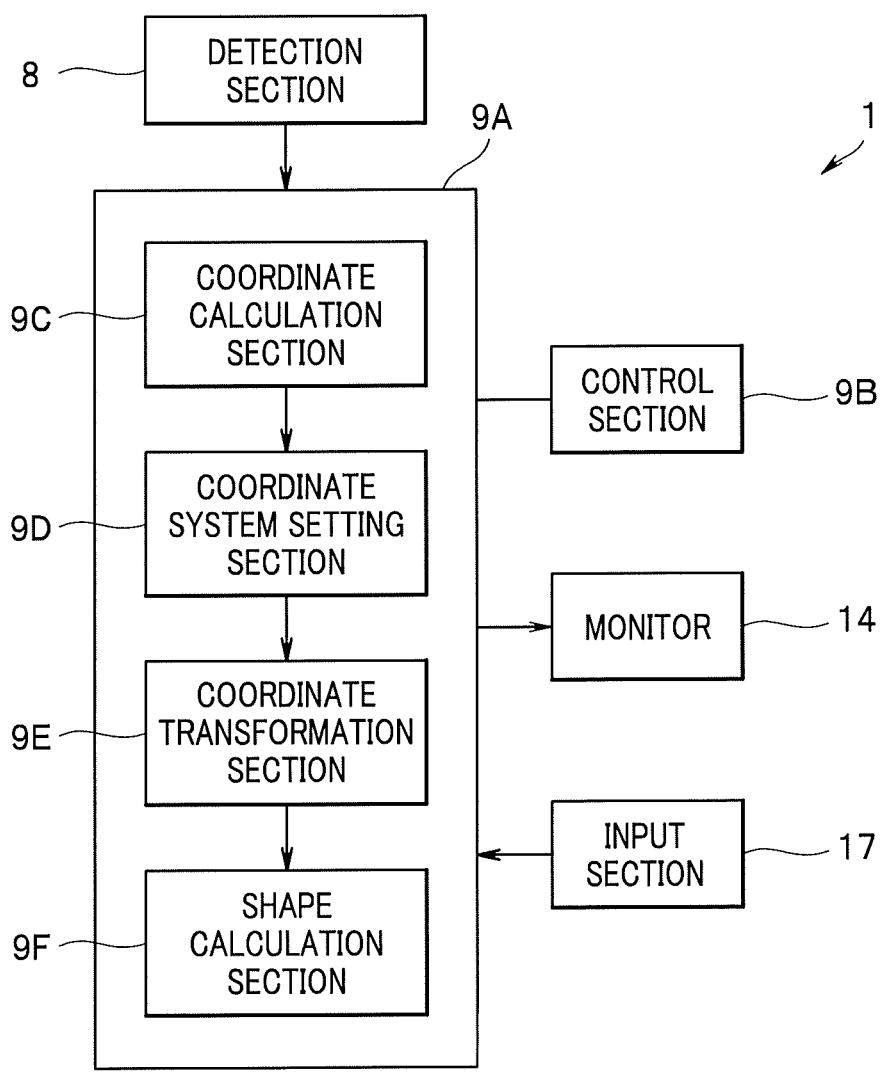
FIG. 5 is a configuration diagram illustrating a configuration of a calculation section of the medical instrument of the first embodiment.
Figure 6:
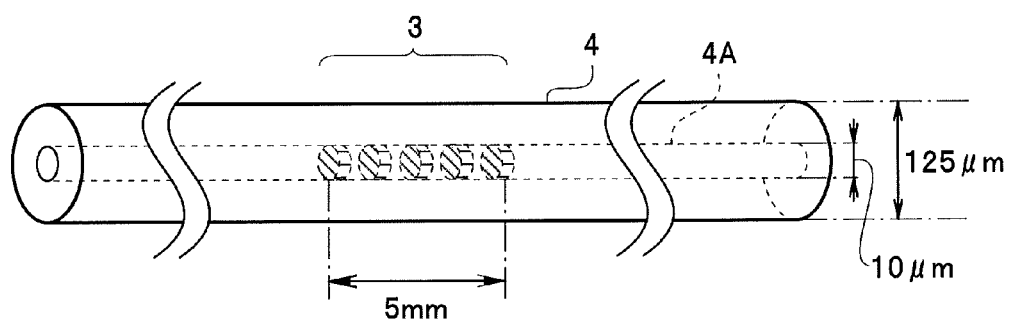
FIG. 6 is a structural diagram illustrating a structure of an FBG sensor section of the medical instrument of the first embodiment.
Figure 7:
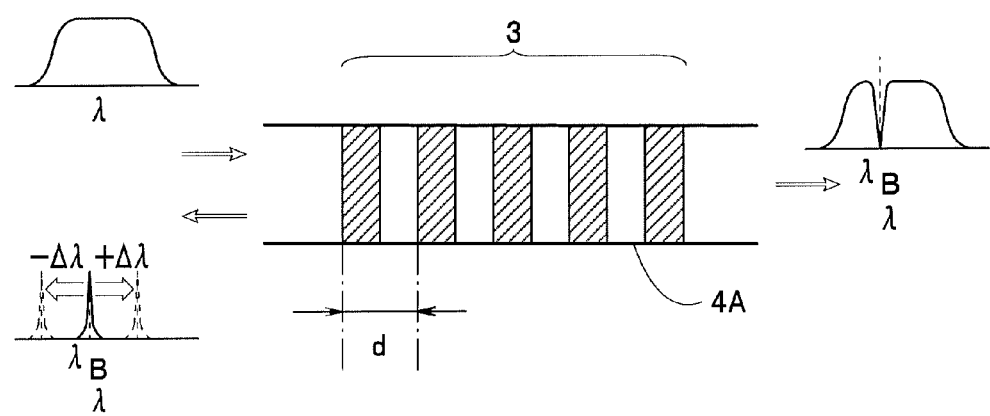
FIG. 7 is a diagram illustrating a function of the FBG sensor section of the medical instrument of the first embodiment.

Next, FIG. 3A is a configuration diagram illustrating a configuration of the optical fiber sensor of the medical instrument according to the present embodiment and FIG. 3B is a cross-sectional view along the line IIIB-IIIB of FIG. 3A. FIG. 4 is a configuration diagram of the medical instrument of the present embodiment, FIG. 5 is a configuration diagram illustrating a configuration of a calculation section of the medical instrument of the present embodiment, FIG. 6 is a configuration diagram illustrating a structure of an FBG sensor section of the medical instrument of the present embodiment and FIG. 7 is a diagram illustrating a function of the FBG sensor section of the medical instrument of the present embodiment.

An optical fiber Bragg grating (Fiber Bragg Grating: hereinafter referred to as "FBG") sensor is an optical fiber provided with a grating section having a variable refractive index in a core section thereof and the grating section thereof reflects light of a predetermined wavelength of incident light. This specific wavelength is referred to as a "Bragg wavelength."

The FBG sensor has a feature that an increase/decrease of the length in a longitudinal direction of the grating section causes its Bragg wavelength to vary. Thus, the FBG sensor is used to measure a temperature or distortion or the like.

An optical fiber sensor based on an optical frequency domain reflectometry multiplexing (OFDR: Optical Frequency Domain Reflectometry) scheme, which is an optical fiber sensor in which a plurality of FBG sensor sections having the same Bragg wavelength are created in an optical fiber, causes reflected light from a reflector which is total reflection termination and reflected light from the optical fiber sensor to interfere with each other, and can thereby detect the degree of deformation of the respective FBG sensor sections, in other words, the degree of distortion generated. Therefore, optical fiber sensors using the OFDR scheme are used as sensors for measuring distortion of, for example, an elongated object.

As shown in FIGS. 3A and 3B, the optical fiber sensor 2, which is distortion detecting means, is a fiber array probe made up of three optical fiber sensors 2A, 2B and 2C bundled around a metal wire 2M via resin 2P and has flexibility.

As shown in FIG. 2, the respective optical fiber sensors 2A, 2B and 2C are provided with FBG sensor sections 3 which are their respective distortion detection sections at the same positions in the axial direction. That is, since the three FBG sensor sections 3 are disposed at the same positions in the axial direction, the optical fiber sensor 2 can measure displacements in three axial directions of the insertion portion 12 where the three FBG sensor sections 3 are arranged.

As shown in FIG. 4, the medical instrument 1 includes the optical fiber sensor 2, a light source 6 disposed in the main unit 15 for emitting wideband light, and a coupler 7 which is an optical part serving as light splitting means for splitting the light emitted from the light source 6 and supplying the light to the optical fiber sensor 2 and a reflector 5 which is reflection means and also serving as interference means for causing the light reflected from the reflector 5 and the light reflected from the FBG sensor sections 3 of the optical fiber sensor 2 to interfere with each other. That is, the light splitting means and the interference means are constructed of the coupler 7 which is a one optical part. An optical switch 7B time-sequentially supplies light to the three optical fiber sensors 2A, 2B and 2C.

Furthermore, the medical instrument 1 includes a detection section 8 which is detecting means for converting the interference light from the coupler 7 to an electric signal for detection, a calculation section 9A which is calculation means for calculating an amount of wavelength shift (difference between the wavelength without deformation and the wavelength with deformation in the portions where the FBG sensor sections 3 exist) of each FBG sensor section 3 from the signal detected by the detection section 8, calculating amounts of deformation of the FBG sensor sections 3 from the calculated amounts of wavelength shift and calculating the shape of the optical fiber sensor 2 from the amount of deformation of the respective FBG sensor sections 3 and a control section 9B that controls the entire medical instrument 1.

As shown in FIG. 5, in the medical instrument 1, the calculation section 9A includes a coordinate calculation section 9C which is coordinate calculating means, a coordinate system setting section 9D which is coordinate system setting means, a coordinate transformation section 9E which is coordinate transformation means, a shape calculation section 9F which is shape calculation means, and allows the two-dimensional shape of the insertion portion 12 from a viewpoint easily recognizable to the operator to be displayed on the monitor 14. The operator performs operation for changing the mode of the two-dimensional shape display of the insertion portion 12 from an input section which is input means or the like.

Here, the operation principles of the FBG sensor will be described using FIG. 6. As shown in FIG. 6, the FBG sensor section 3 is a diffraction grating (grating) where a refractive index of a core section 4A periodically varies over a predetermined length (e.g., 5 mm) of an optical fiber 4. By irradiating ultraviolet rays onto the germanium-doped core section 4A via a mask, the refractive index slightly increases due to a photo refractive effect.

It is the FBG sensor section 3 that takes advantage of this effect and includes portions (gratings) having a high refractive index periodically formed in the axial direction. The number of gratings and the grating width with respect to the core section in the axial direction in FIG. 6 or the like are different from those of the actual FBG sensor section for ease of understanding of the structure.

As shown in FIG. 7, the FBG sensor section 3 reflects only light having a Bragg wavelength $\lambda B$ which is a predetermined wavelength and expressed by the following equation, out of the incident light according to a distance d of the diffraction grating, in other words, the period.

$$\lambda B = 2 \times n \times d$$

where n is a refractive index of the core section 4A.

When, for example, the refractive index n of the core section 4A is 1.45 and the Bragg wavelength $\lambda B$ is 1550 nm, the distance d of the diffraction grating is on the order of 0.53 μm.

FIG. 7 is a diagram illustrating operation of the FBG sensor section and the figure at the top left is a diagram illustrating the intensity of light with respect to the wavelength $\lambda$ of the incident light and the incident light has a predetermined width of wavelength, that is, band. The figure at the bottom left is a diagram illustrating the intensity of light with respect to the wavelength $\lambda$ of reflected light reflected by the FBG sensor section 3 and the reflected light is light having a Bragg wavelength $\lambda B$. The figure on the right side is a diagram illustrating the intensity of light with respect to the wavelength $\lambda$ of the incident light that has passed through the FBG sensor section 3 and shows that the transmitted light includes no Bragg wavelength $\lambda B$ component reflected by the FBG sensor section 3.

As is clear from the above described equation, when the FBG sensor section 3 extends in length, the distance d of the diffraction grating also increases, and therefore the Bragg wavelength $\lambda B$ moves toward the longer wavelength side. On the contrary, when the FBG sensor section 3 contracts, the distance d of the diffraction grating also decreases, and therefore the Bragg wavelength $\lambda B$ moves toward the shorter wavelength side.

Thus, the FBG sensor section 3 can be used as a sensor to detect temperature or external force, and the FBG sensor section 3 in the present embodiment detects the amount of deflection of the optical fiber sensor 2, that is, the amount of bending deformation in the axial direction.

According to the optical frequency domain reflectometry (OFDR) scheme, interference light is formed of the reflected light from the FBG sensor section 3 and the reflected light from the reflector 5, and therefore even if a plurality of FBG sensor sections 3 are formed in one optical fiber sensor 2, the amounts of deformation of the respective FBG sensor sections 3 can be measured.

Figure 8:
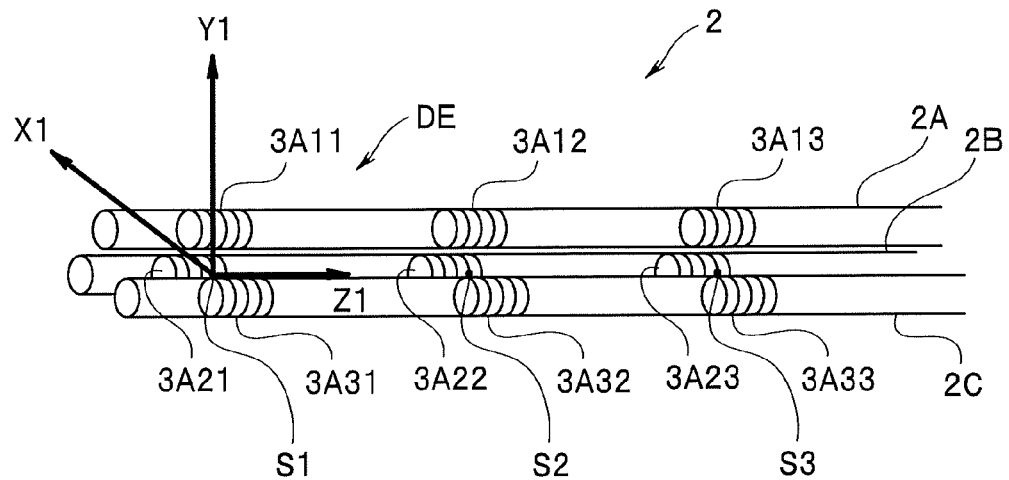
FIG. 8 is a diagram illustrating a coordinate system of the optical fiber sensor of the medical instrument of the first embodiment.
Figure 9:
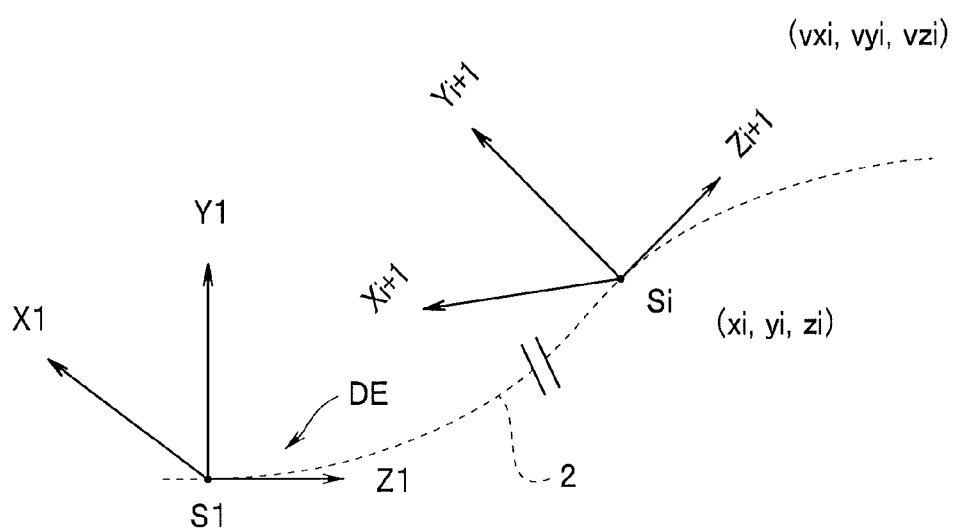
FIG. 9 is a diagram illustrating processing by the calculation section of the medical instrument of the first embodiment.

Next, processing carried out by the calculation section 9A will be described using FIG. 8 and FIG. 9. FIG. 8 is a diagram illustrating a coordinate system in the optical fiber sensor 2 of the medical instrument and FIG. 9 is a diagram illustrating processing of the calculation section of the medical instrument.

As shown in FIG. 8, the FBG sensor sections 3 formed in each of the optical fiber sensors 2A to 2C are formed at equal intervals in the axial direction and the three FBG sensor sections 3 of the three optical fiber sensors 2A to 2C are fixed to the insertion body located at the same positions with respect to the axial direction. As shown in FIG. 8, when the term "position of the FBG sensor section 3" is simply used, this means a center position of the FBG sensor group made up of the three FBG sensor sections 3 arranged at the same positions in the axial direction.

First, the coordinate calculation section 9C of the calculation section 9A calculates first three-dimensional coordinates of the respective FBG sensor sections 3 in the first three-dimensional coordinate system whose origin is a position S of any one FBG sensor section 3, or more precisely, the center position of the three FBG sensor sections 3 arranged at the same positions with respect to the axial direction of the optical fiber sensor 2 based on the measurement results of the FBG sensor sections 3.

The coordinate calculation section 9C sets, for example, an $XYZ_1$ coordinate system which is a first three-dimensional coordinate system whose origin is the center position S1 of the three FBG sensor sections $3A1_1$, $3A2_1$ and $3A3_1$ formed at the position closest to the proximal end portion PE side of the optical fiber sensor 2 and calculates a center position $S2(x_1, y_1, z_1)$ and an orientation $(vx_1, vy_1, vz_1)$ of the neighboring three FBG sensor sections $3A1_2$, $3A2_2$ and $3A3_2$ from the amount of deformation of the FBG sensor sections $3A1_1$, $3A2_1$ and $3A3_1$.

The coordinate calculation section 9C further calculates a matrix $T_1^2$ of transformation into a three-dimensional coordinate system $XYZ_2$ whose reference origin is the center position S2 of the FBG sensor sections $3A1_2$, $3A2_2$ and $3A3_2$ from the calculated center position $S2(x_1, y_1, z_1)$ and orientation $(vx_1, vy_1, vz_1)$ of the FBG sensor sections $3A1_2$, $3A2_2$ and $3A3_2$ using the following (Equation 1).

$$T_1^2 = \begin{pmatrix} r11 & r12 & r13 & tx \\ r21 & r22 & r23 & ty \\ r31 & r32 & r33 & tz \\ 0 & 0 & 0 & 1 \end{pmatrix} \quad \text{(Equation 1)}$$

Here, $r_{ij}$ (i=1, 2, 3: j=1, 2, 3) denotes a rotation from a three-dimensional coordinate system $XYZ_1$ to a three-dimensional coordinate system $XYZ_2$ (a rotation matrix is calculated from the Z-axis and orientation $(vx_1, vy_1, vz_1)$ of the three-dimensional coordinate system $XYZ_2$) and $t_x$, $t_y$ and $t_z$ denote translation (same as the position $(x_1, y_1, z_1)$).

Likewise, the coordinate calculation section 9C calculates a center position $S3(x_2, y_2, z_2)$ and orientation $(vx_2, vy_2, vz_2)$ of three FBG sensor sections $3A1_3$, $3A2_3$ and $3A3_3$ adjacent to the set three-dimensional coordinate system $XYZ_2$ and calculates a transformation matrix T.

By repeating similar processing, the coordinate calculation section 9C finally calculates a center position $Sn(x_{n-1}, y_{n-1}, z_{n-1})$ and orientation $(vx_{n-1}, vy_{n-1}, vz_{n-1})$ of three FBG sensor sections $3A1_n$, $3A2_n$ and $3A3_n$ closest to the distal end portion DE and transformation matrix $T_{n-1}{}^n$.

Using the transformation matrix, the coordinate calculation section 9C then transforms the center position S of the three FBG sensor sections 3 to a three-dimensional coordinate system $XYZ_1$. When, for example, a center position $Si+1(x_i, y_i, z_i)$ and orientation $(vx_i, vy_i, vz_i)$ of three FBG sensor sections $3A1_{i+1}$, $3A2_{i+1}$ and $3A3_{i+1}$ are calculated in a coordinate system using the center position Si of the three FBG sensor sections $3A1_i$, $3A2_i$, $3A3_i$ as a reference, a $(x^w_{i+1}, y^w_{i+1}, z^w_{i+1})$ position in the $XYZ_1$ coordinate system is calculated using the following (Equation 2).

$$\begin{pmatrix} x^w_{i+1} \\ y^w_{i+1} \\ z^w_{i+1} \\ 1 \end{pmatrix} = T_1^2 \; T_2^3 \; \ldots \; T_{i-1}^i \begin{pmatrix} x_i \\ y_i \\ z_i \\ 1 \end{pmatrix} \quad \text{(Equation 2)}$$

The coordinate calculation section 9C likewise transforms the center position S of all the three FBG sensor sections 3 into the $XYZ_1$ coordinate system, connects the transformed coordinates and thereby calculates the three-dimensional shape of the optical fiber sensor 2, that is, the three-dimensional shape of the insertion portion 12 to which the optical fiber sensor 2 is fixed.

The shape of the optical fiber sensor 2 can be calculated by performing interpolation processing or the like based on the three-dimensional coordinates of the position S of the FBG sensor section 3 according to the $XYZ_1$ coordinate system which is the first three-dimensional coordinate system calculated by the coordinate calculation section 9C of the calculation section 9A which has already been described.

Figure 10:
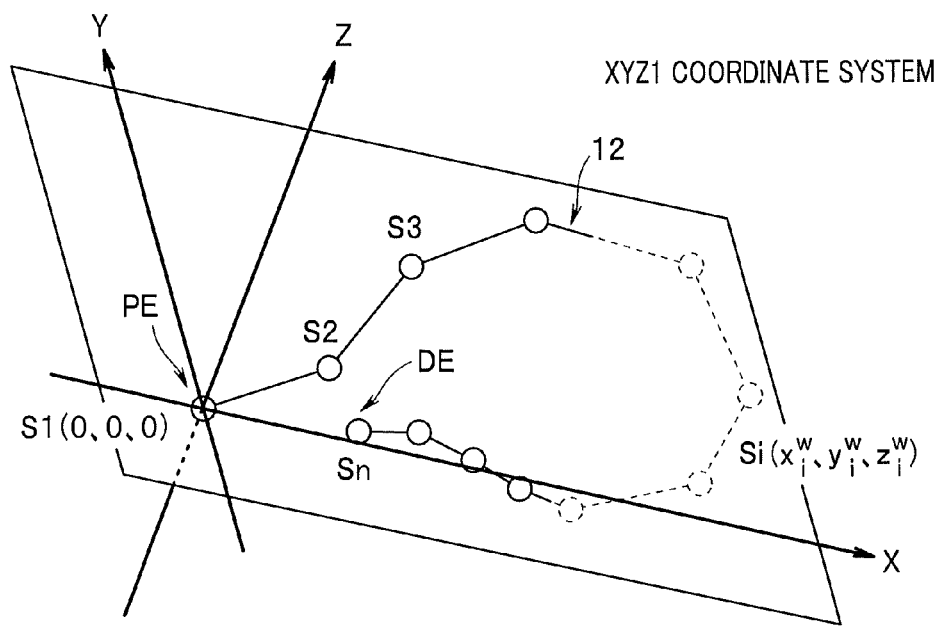
FIG. 10 is a diagram illustrating processing by the calculation section of the medical instrument of the first embodiment.

However, as shown in FIG. 10, the origin of the $XYZ_1$ coordinate system is the center position S1 of three FBG sensor sections $3A1_1$, $3A2_1$ and $3A3_1$ formed at a position closest to the proximal end portion PE side of the optical fiber sensor 2, but the axial direction is not a direction of particular significance. Thus, when the optical fiber sensor 2 rotates or the examinee 11 changes his/her posture, the two-dimensional shape of the optical fiber sensor 2 displayed on the monitor 14 considerably changes. Moreover, the two-dimensional shape of the optical fiber sensor 2 displayed on the monitor 14 is the shape of the optical fiber sensor 2 which is the three-dimensional shape transformed into the two-dimensional shape based on a certain viewpoint. The two-dimensional shape displayed greatly differs depending on the parameter used for transformation.

It is difficult for the operator to precisely recognize the two-dimensional shape of the insertion portion 12 when the $XYZ_1$ coordinate system shown in FIG. 10 is observed from the X-axis direction assuming the X-axis as a reference axis, in other words, projected onto the YZ plane.

On the other hand, it is often relatively easy for the operator to recognize the two-dimensional shape of the insertion portion 12 observed from the Z-axis direction, in other words, projected onto the XY plane. However, it is not easy to perform setting operation to display the two-dimensional shape of the insertion portion 12 from a viewpoint more easily recognizable to the operator.

By contrast, in order to display the two-dimensional shape of the insertion portion 12 from a viewpoint more easily recognizable to the operator, the calculation section 9A of the medical instrument 1 of the present embodiment performs further processing after the end of processing by the coordinate calculation section 9C.

Hereinafter, the processing by the calculation section 9A of the medical instrument 1 will be described using FIG. 11 to FIG. 15. FIG. 11 to FIG. 15 are diagrams illustrating the processing by the calculation section of the medical instrument according to the present embodiment.

The coordinate system setting section 9D which is coordinate system setting means of the calculation section 9A of the medical instrument 1 according to the present embodiment sets a second three-dimensional coordinate system based on the three-dimensional coordinates of the position S of n FBG sensor sections 3 in the $XYZ_1$ coordinate system which is the first three-dimensional coordinate system calculated by the coordinate calculation section 9C.

Figure 11:
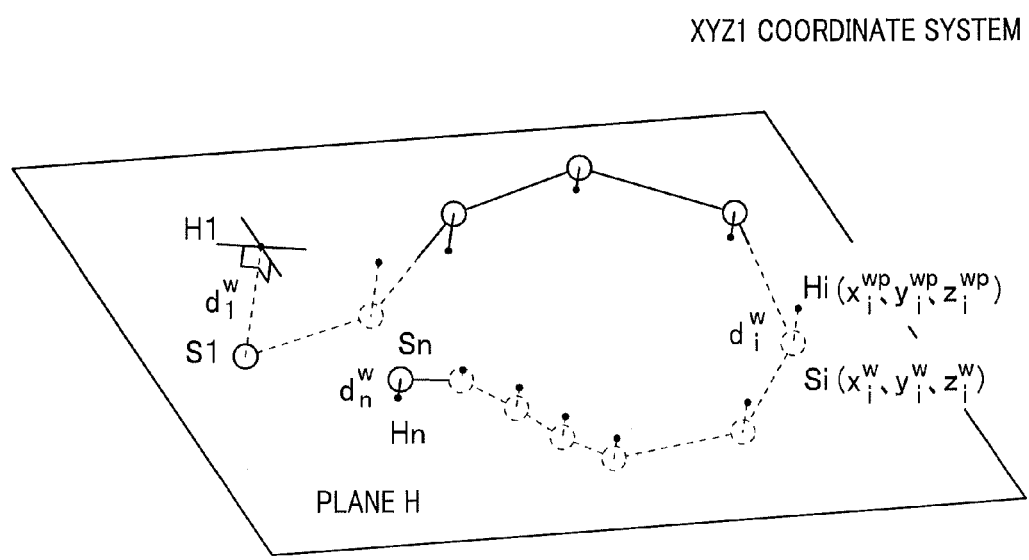
FIG. 11 is a diagram illustrating processing by the calculation section of the medical instrument of the first embodiment.

That is, as shown in FIG. 11, the coordinate system setting section 9D first calculates the sum of squares of distances from the position S of the respective FBG sensor sections 3 with respect to an arbitrary plane to calculate a plane H whose distance from the position S of the n FBG sensor sections 3 is minimum. Assuming the coordinates of the position Si are $(x_i^w, y_i^w, z_i^w)$ here, the minimum distance between the position Si and the arbitrary plane, that is, the length $d_i^w$ of the normal to the arbitrary plane from the position Si is calculated by the following (Equation 3).

$$d_1^w = \frac{|ax + by + cz + p|}{\sqrt{a^2 + b^2 + c^2}} \quad \text{(Equation 3)}$$

Here, suppose the equation of the arbitrary plane is "$ax+by+cz+p=0$".

The coordinate system setting section 9D then calculates the plane H where the sum total D of lengths of n normals $d_i^w$ shown in the following (Equation 4) is minimum, that is, calculates coefficients a, b, c and p of the equation of the plane.

$$D = \sum_{n=1}^{n} d_i^w \quad \text{(Equation 4)}$$

Figure 12:
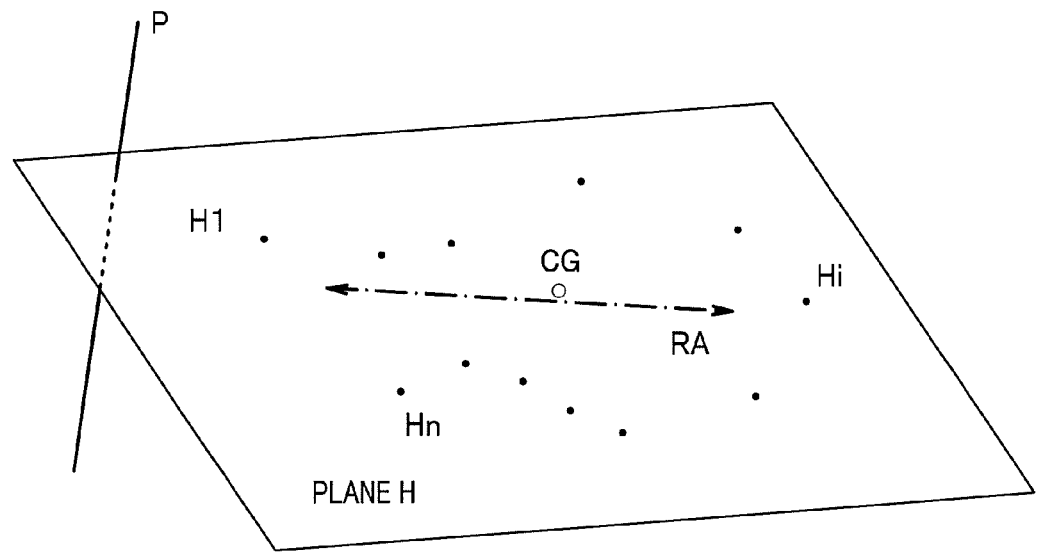
FIG. 12 is a diagram illustrating processing by the calculation section of the medical instrument of the first embodiment.

Next, as shown in FIG. 11, the coordinate system setting section 9D calculates points H1 to Hn at which the normals from positions S1 to Sn of the n FBG sensor sections 3 to the plane H cross the plane H. As shown in FIG. 12, the coordinate system setting section 9D then calculates a center of gravity CG and a distribution direction RA of the points H1 to Hn on the plane H.

That is, the coordinate system setting section 9D calculates a point $Hi(x_i^{wp}, y_i^{wp}, z_i^{wp})$ at which the normal is drawn from the position $Si(x_i^w, y_i^w, z_i^w)$ of the FBG sensor section 3 to the plane H and further calculates the center of gravity $CG(gx^w, gy^w, gz^w)$ from the following (Equation 5).

$$\begin{pmatrix} gx^w \\ gy^w \\ gz^w \end{pmatrix} = \begin{pmatrix} \frac{1}{n}\sum_{n=1}^{n} x_i^{wp} \\ \frac{1}{n}\sum_{n=1}^{n} y_i^{wp} \\ \frac{1}{n}\sum_{n=1}^{n} z_i^{wp} \end{pmatrix} \quad \text{(Equation 5)}$$

Furthermore, the coordinate system setting section 9D calculates the distribution direction RA of the point $Hi(x_i^{wp}, y_i^{wp}, z_i^{wp})$ through a publicly known main component analysis or the like.

Figure 13:
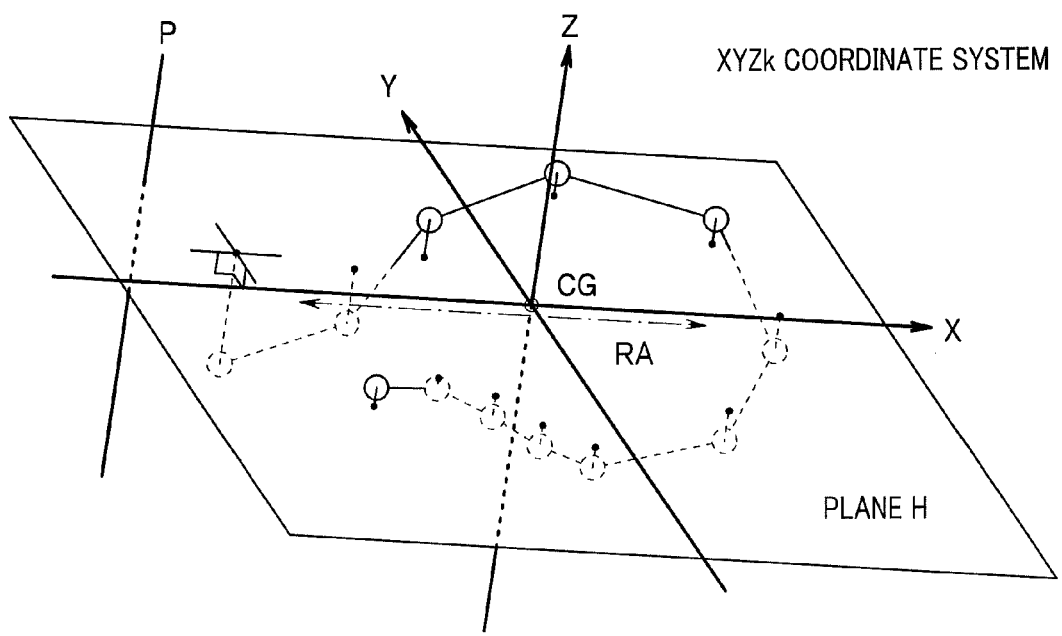
FIG. 13 is a diagram illustrating processing by the calculation section of the medical instrument of the first embodiment.

Next, as shown in FIG. 13, the coordinate system setting section 9D sets a second three-dimensional coordinate system XYZk based on the center of gravity $CG(gx^w, gy^w, gz^w)$, the distribution direction RA of the point $Hi(x_i^{wp}, y_i^{wp}, z_i^{wp})$ and the normal P direction of the plane H. That is, the coordinate system setting section 9D sets the center of gravity CG as the origin, the distribution direction RA as the X-axis, and the normal P direction of the plane H as the Z-axis and the direction orthogonal to the respective axes as the Y-axis (right-hand system).

Next, as shown in FIG. 13, the coordinate transformation section 9E which is the coordinate transformation means transforms the position Si of the FBG sensor section 3 from the first three-dimensional coordinates according to the first three-dimensional coordinate system $XYZ_1$ to second three-dimensional coordinates according to the second three-dimensional coordinate system XYZk.

Figure 14:
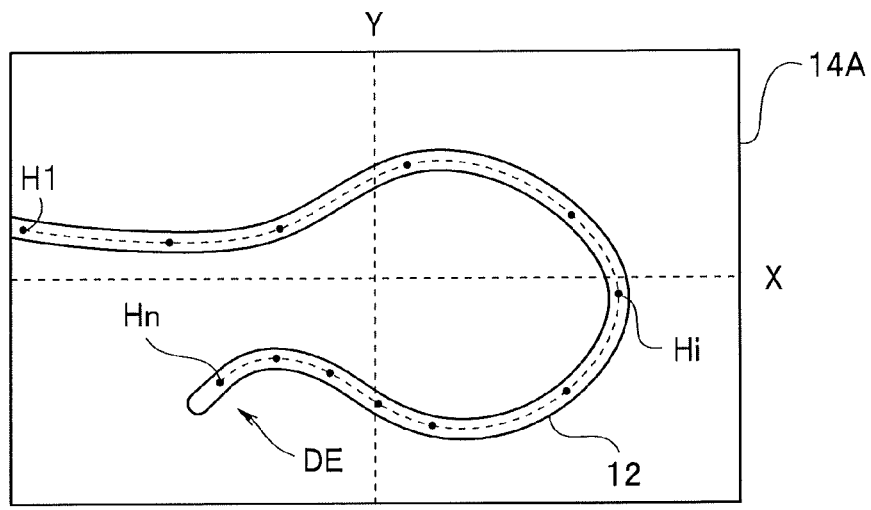
FIG. 14 is a diagram illustrating processing by the calculation section of the medical instrument of the first embodiment.

Furthermore, as shown in FIG. 14, the shape calculation section 9F which is the shape calculating means projects the positions of the n FBG sensor sections 3 of the optical fiber sensor 2 according to the second three-dimensional coordinate system XYZk onto the plane XY, in other words, assuming the direction of the line of sight as the Z-axis, and then calculates the two-dimensional shape of the optical fiber sensor 2, that is, the two-dimensional shape of the insertion portion 12 through interpolation processing or the like and outputs the two-dimensional shape to the monitor 14.

That is, the two-dimensional shape of the insertion portion 12 displayed on the display region 14A of the monitor 14 is the three-dimensional shape of the insertion portion 12 projected onto the XY plane of the second three-dimensional coordinate system.

Figure 15:
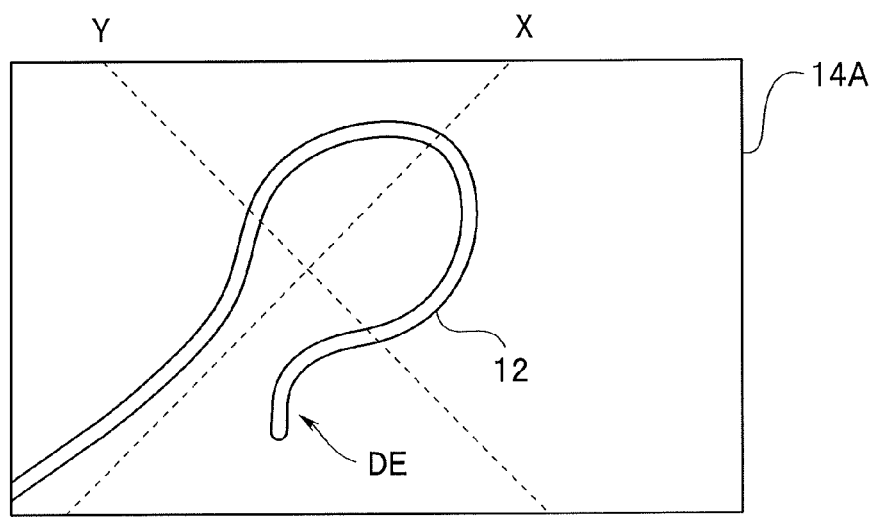
FIG. 15 is a diagram illustrating processing by the calculation section of the medical instrument of the first embodiment.

As shown in FIG. 15, the two-dimensional shape of the insertion portion 12 displayed on the display region 14A of the monitor 14 can be rotated or displayed on an enlarged or reduced scale by the operator operating the input section 17.

The two-dimensional shape of the insertion portion 12 calculated by the calculation section 9A of the medical instrument 1 through the above described processing is a shape from a viewpoint easily recognizable to the operator. Furthermore, even if the examinee changes his/her posture or the insertion portion moves, the two-dimensional shape of the insertion portion 12 displayed on the monitor 14 is stable.

That is, since the medical instrument 1 sets the viewpoint based on the coordinates of the FBG sensor section 3 which is the shape of the insertion portion 12 inserted into the body cavity and displays the two-dimensional image, a stable display image can be obtained.

Here, it may also be possible to calculate the three-dimensional shape of the optical fiber sensor 2 from the position of the FBG sensor section 3 according to the first three-dimensional coordinate system XYZ1 through interpolation processing or the like, then determine a viewpoint based on the second three-dimensional coordinate system XYZk by the coordinate system setting section 9D and it may be possible for the shape calculation section 9F to calculate the two-dimensional shape of the insertion portion 12.

Furthermore, the coordinate system setting section 9D may detect an FBG sensor section 3 where the first calculated distance between the plane H and the FBG sensor section 3 is considerably large and calculate a new plane H based on information on any FBG sensor section other than the detected FBG sensor section 3. This is because it is highly possible that the FBG sensor section 3 whose distance from the plane H is considerably large may have not been inserted into the body of the examinee 11 yet.

Furthermore, instead of calculating the plane H based on information on all the FBG sensor sections 3, the coordinate system setting section 9D may also calculate the plane H based on, for example, information on three FBG sensor sections 3: the FBG sensor section 3 on the proximal end portion PE side, the FBG sensor section 3 on the distal end portion DE side and the FBG sensor section 3 located intermediate between the proximal end portion PE and the distal end portion DE.

Furthermore, the calculation section 9A may have storage means (not shown) for time-sequentially storing shapes of the insertion portion 12, calculate an average normal direction and center of gravity from the normal direction P of the plane H and center of gravity CG calculated in the past and set the second three-dimensional coordinate system XYZk.

Furthermore, deformation of each section of the insertion portion 12 may be detected using a distortion gauge or the like instead of the optical fiber sensor 2 as the distortion detecting means.

Second Embodiment

Hereinafter, a medical instrument 1B according to a second embodiment of the present invention will be described with reference to the accompanying drawings. Since the configuration and operation of the medical instrument 1B are similar to those of the medical instrument 1 of the first embodiment, the same components will be assigned the same reference numerals and descriptions thereof will be omitted.

Figure 16:
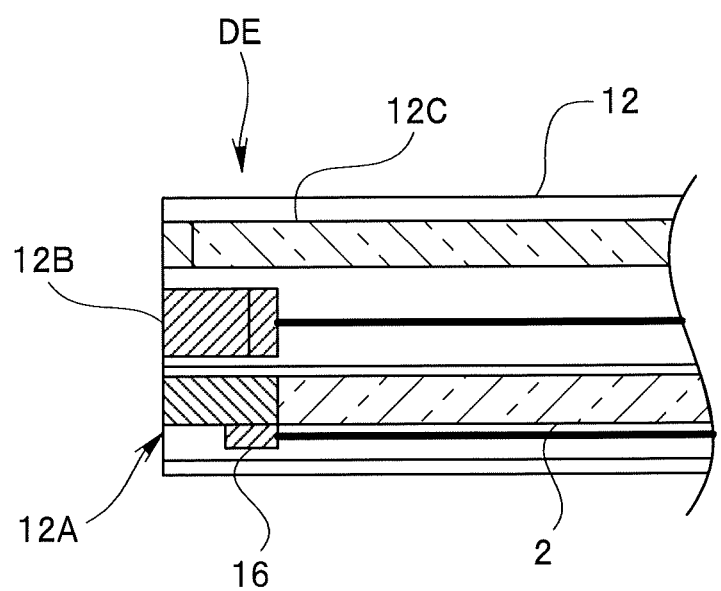
FIG. 16 is a structural diagram illustrating a structure of a cross section of a distal end portion DE of an insertion portion of a medical instrument according to a second embodiment.
Figure 17:
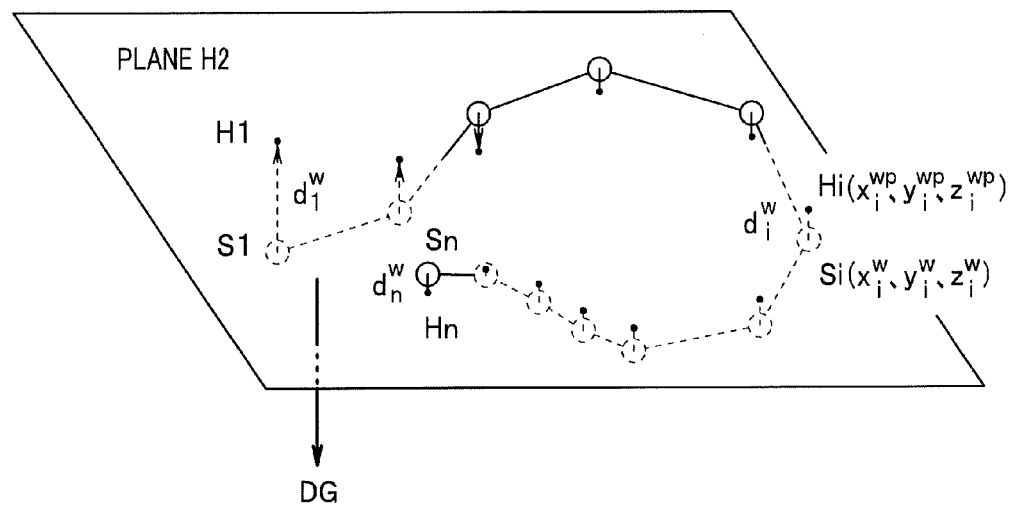
FIG. 17 is a diagram illustrating processing by the calculation section of the medical instrument of the second embodiment.
Figure 18:
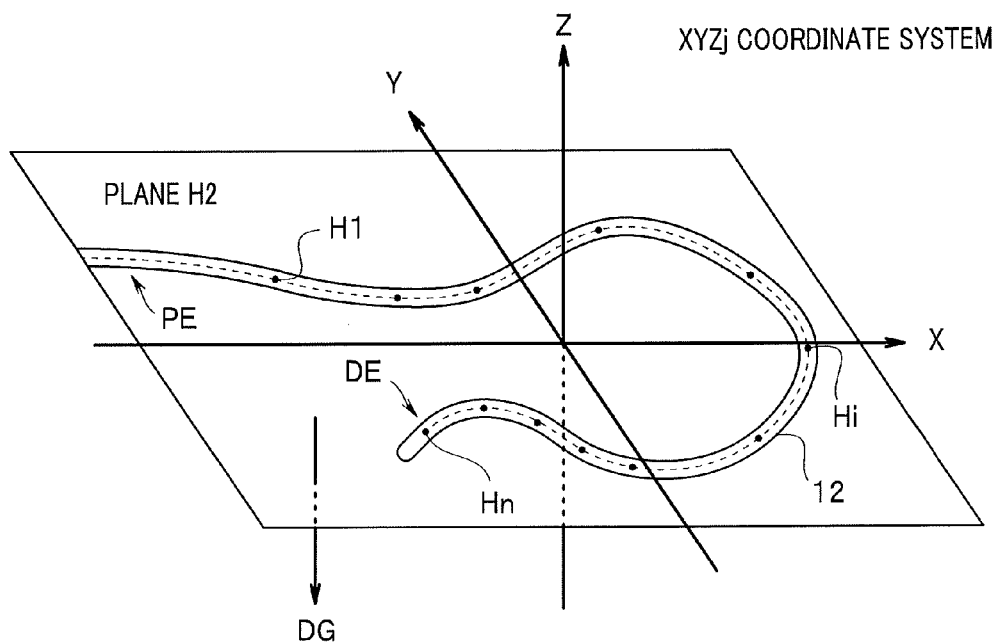
FIG. 18 is a diagram illustrating processing by the calculation section of the medical instrument of the second embodiment.

FIG. 16 is a structural diagram illustrating a structure of a cross section of a distal end portion DE of an insertion portion of the medical instrument according to the second embodiment, and FIG. 17 and FIG. 18 are diagrams illustrating processing by the calculation section of the medical instrument 1 of the second embodiment.

As shown in FIG. 16, in the medical instrument 1B of the present embodiment, a gravity sensor 16, which is gravity detecting means, is disposed at a distal end portion DE of the insertion portion 12. A CCD 12B which is image pickup means and a light guide 12C which is illumination means or the like are also disposed at the distal end portion DE as shown in FIG. 16. The gravity sensor 16 for detecting the direction of gravity is disposed at the distal end portion of the optical fiber sensor 2 inserted in the channel 12A of the insertion portion 12.

As shown in FIG. 17 and FIG. 18, the calculation section 9C of the medical instrument 1B sets a three-dimensional coordinate system based on the direction of gravity DG detected by the gravity sensor 16. A $XYZ_1$ coordinate system tp which is a first three-dimensional coordinate system and a XYZj coordinate system which is a second three-dimensional coordinate system set a plane H2 whose Z-axis is the direction of gravity DG.

Thus, in addition to the effect of the medical instrument 1 of the first embodiment, the medical instrument 1B always sets a stable direction, and can thereby provide images easily observable to the operator. Furthermore, since the calculation processing by the calculation section 9C of the medical instrument 1B becomes simple, it is possible to realize simplification of the apparatus and high-speed processing.

The medical instrument 1B may calculate the direction of gravity using a sensor for detecting the orientation of a specific direction such as an azimuth sensor or the like instead of the gravity sensor 16.

Third Embodiment

Figure 19:
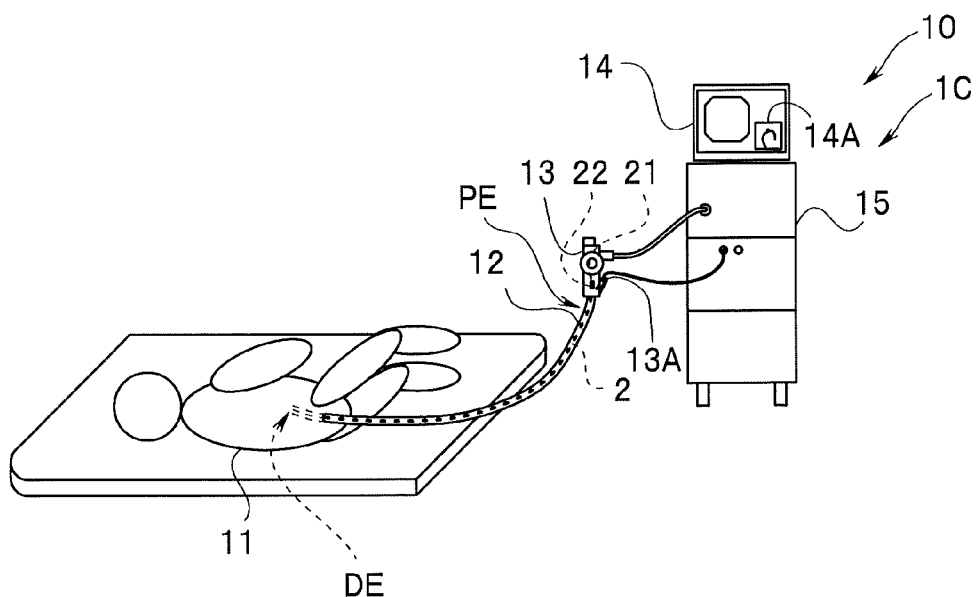
FIG. 19 is a diagram illustrating a situation in which a medical instrument according to a third embodiment is used.
Figure 20:
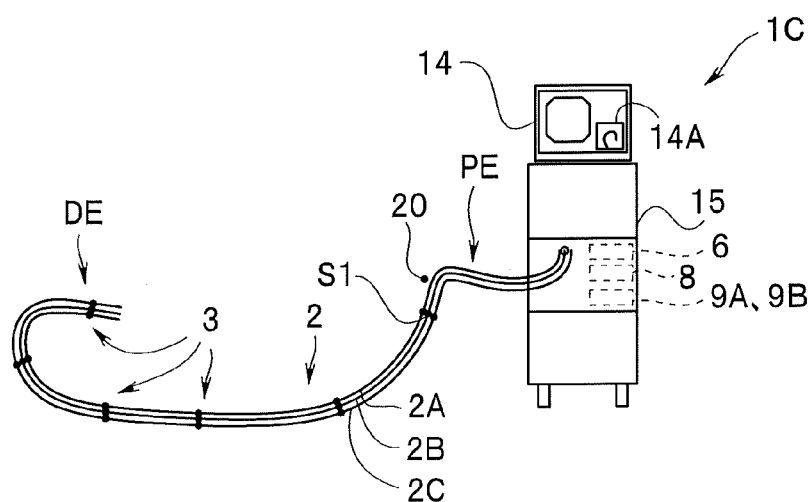
FIG. 20 is a diagram illustrating a configuration of the medical instrument according to the third embodiment.

FIG. 19 is a diagram illustrating a situation in which a medical instrument according to the present embodiment is used and FIG. 20 is a diagram illustrating a configuration of the medical instrument according to the present embodiment.

The configuration of the medical instrument according to the third embodiment is different from the medical instrument of the first embodiment shown in aforementioned FIG. 1 to FIG. 15 and the medical instrument according to the second embodiment shown in FIG. 16 to FIG. 18 in that the operation portion is provided with a gyroscope and an acceleration sensor. Therefore, only the differences will be described and the same components as those in the first embodiment will be assigned the same reference numerals and descriptions thereof will be omitted.

In the medical instrument 1C of the third embodiment shown in FIG. 19, the operation portion 13 is provided with a gyroscope 21 and an acceleration sensor 22 which are movement sensors for detecting movement of the operation portion 13.

The gyroscope 21 is a measuring section that detects angular velocity ω which is a rotation velocity of an object and the acceleration sensor 22 is a measuring section that measures acceleration of an object. Since the operation portion 13 is provided with the position sensor, when the operator sets an initial position of the position sensor at a certain point in time as a reference point 20 (see FIG. 20), the medical instrument 1C can calculate a correlation between the position of the position sensor and the reference point 20 corresponding to the movement of the operation portion 13 thereafter. The acceleration sensor 22 is a three-axis acceleration sensor and, for example, a small three-axis acceleration sensor created using a MEMS technique can be used.

Here, FIG. 10 of the aforementioned first embodiment has shown that the origin of the XYZ1 coordinate system is the center position S1 of the three FBG sensor sections $3A1_1$, $3A2_1$ and $3A3_1$ formed at a position closest to the proximal end portion PE side of the optical fiber sensor 2, but when the optical fiber sensor 2 rotates or the examinee 11 changes his/her posture, the shape of the optical fiber sensor 2 displayed on the monitor 14 considerably changes.

However, in the medical instrument 1C of the present embodiment, the reference coordinate system setting section 9D sets a reference coordinate system reference three-dimensional coordinate system XYZk whose origin is the reference point 20 which is the initial position of the gyroscope 21 and the acceleration sensor 22 which are movement sensors.

The coordinate transformation section 9E then transforms first coordinates according to the first three-dimensional coordinate system XYZ1 coordinate system of the FBG sensor sections 3 which are their respective distortion detection sections into second coordinates according to the reference three-dimensional coordinate system XYZk and the shape calculation section 9F calculates the shape of the insertion portion 12 based on the second coordinates and displays the second coordinates on the monitor 14.

Though the reference point 20 is an arbitrary point in space, but is a fixed point that never moves. Thus, even if the optical fiber sensor 2 rotates or the examinee 11 changes his/her posture, the medical instrument 1 can stably display the shape of the insertion portion 12.

Figure 21:
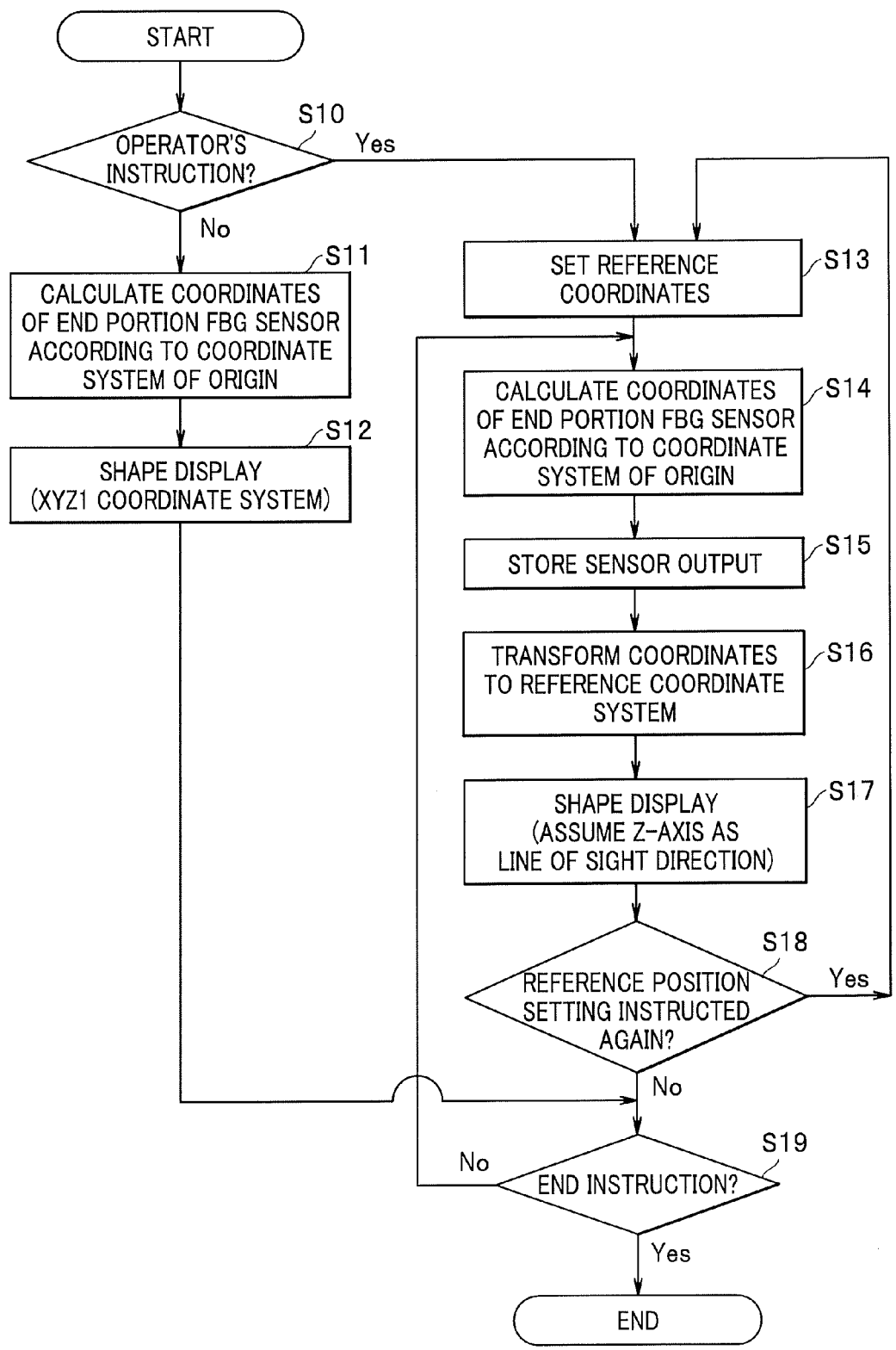
FIG. 21 is a flowchart illustrating a processing flow of the medical instrument of the third embodiment.

Next, the processing flow of the medical instrument 1C will be described according to the flowchart in FIG. 21. FIG. 21 is a flowchart illustrating the processing flow of the medical instrument of the present embodiment.

First, in step S10, upon receiving an instruction for starting processing from the operator, the medical instrument 1C starts the processing. In the case where there is no instruction for starting processing, in step S11, the shape calculation section 9F calculates the shape of the optical fiber sensor 2 through interpolation processing or the like from the first coordinates of the respective FBG sensor sections 3 according to the first three-dimensional coordinate system XYZ1 calculated by the coordinate calculation section 9C.

In step S12, the monitor 14 displays the shape of the optical fiber sensor 2 according to the first three-dimensional coordinate system XYZ1, that is, the shape of the insertion portion 12. The process then moves to step S19.

Here, in the case where there is an instruction for starting processing in step S10, to be more specific, when an instruction is received from the operator by pressing a switch (not shown) disposed in the operation portion 13, the process branches to step S13 and the medical instrument 1C sets the position of the operation portion 13 when the switch is pressed, or to be exact, the positions of the gyroscope 21 and the acceleration sensor 22, which are position sensors as the reference point 20 in step S13. Assuming the reference point 20 as the origin, the medical instrument 1C sets the reference three-dimensional coordinate system XYZk based on the orientation of the position sensor.

Next, in step S14, the coordinate calculation section 9C sets the XYZ1 coordinate system which is the first three-dimensional coordinate system whose origin is the center position S1 of the three FBG sensor sections $3A1_1$, $3A2_1$ and $3A3_1$ formed at the position closest to the proximal end portion PE side of the optical fiber sensor 2 and transforms a center position Sn of the three FBG sensor sections 3 into the three-dimensional coordinate system XYZ1.

Next, in step S15, the coordinate transformation section 9E incorporates and stores the outputs of the movement sensors disposed in the operation portion 13 (parallel movement Hi and rotation Ri).

Next, in step S16, the coordinate transformation section 9E performs coordinate transformation processing from the first three-dimensional coordinate system XYZ1 to the reference three-dimensional coordinate system XYZk. That is, from the outputs of the movement sensors, a transformation matrix from the first three-dimensional coordinate system XYZ1 to the reference three-dimensional coordinate system XYZk is expressed by the following (Equation 6).

$$T_0^1 = \begin{pmatrix} r11 & r12 & r13 & hx \\ r21 & r22 & r23 & hy \\ r31 & r32 & r33 & hz \\ 0 & 0 & 0 & 1 \end{pmatrix} \quad \text{(Equation 6)}$$

Assuming the coordinates in the three-dimensional coordinate system XYZ1 are (Xs, Ys, Zs), the post-transformation coordinates (Xw, Yw, Zw) in the reference three-dimensional coordinate system XYZk are transformed according to the following (Equation 7).

$$\begin{pmatrix} x_w \\ y_w \\ z_w \\ 1 \end{pmatrix} = T_0^1 \begin{pmatrix} x_s \\ y_s \\ z_s \\ 1 \end{pmatrix}$$ (Equation 7)

Furthermore, assuming the nth transformation matrix is $T^n_{n-1}$ and the position coordinates are (Xs, Ys, Zs), the coordinates are transformed according to the following (Equation 8).

$$\begin{pmatrix} x_w \\ y_w \\ z_w \\ 1 \end{pmatrix} = T_0^1 \; T_1^2 \; \ldots \; T_{n-1}^n \begin{pmatrix} x_s \\ y_s \\ z_s \\ 1 \end{pmatrix}$$ (Equation 8)

The shape calculation section 9F then connects the coordinates in the transformed reference three-dimensional coordinate system XYZk and performs interpolation processing or the like and thereby calculates the three-dimensional shape of the optical fiber sensor 2, that is, the shape of the insertion portion 12 in which the optical fiber sensor 2 is disposed.

Next, in step S17, the shape calculation section 9F generates a display image for the three-dimensional shape of the insertion portion 12 by assuming the Z-axis direction in the reference three-dimensional coordinate system XYZk as the direction of line of sight and displays the display image on the monitor 14.

Next, in step S18, when the switch for instructing the start of processing is pressed again, the medical instrument 1C returns to step S13, resets the position of the operation portion 13 at that moment as a new reference point 20 and repeats the processing from step S13 to step S18 over again.

On the other hand, if the switch for an instruction for starting the processing is not pressed again, in step S19, the medical instrument 1C repeats the processing from step S14 until an instruction for a processing end is received from the operator and displays the shape of the insertion portion 12 in real time on the monitor 14.

Figure 22A:
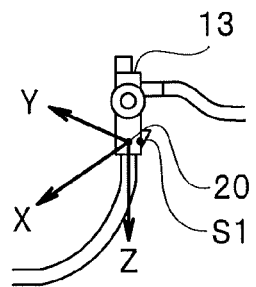
FIG. 22A is a diagram illustrating the position of the operation portion in the diagram illustrating the shape of the insertion portion displayed in the display region of the monitor in FIG. 20.
Figure 22B:
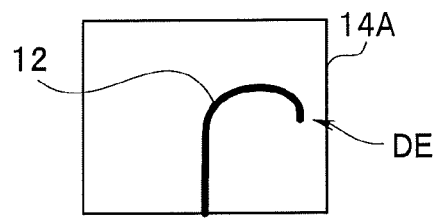
FIG. 22B is a diagram illustrating the shape of the insertion portion in a three-dimensional coordinate system XYZ1 whose origin is the position of the FBG sensor section in the diagram illustrating the shape of the insertion portion displayed in the display region of the monitor in FIG. 20.
Figure 22C:
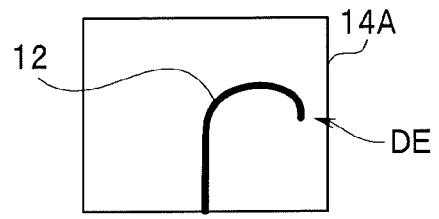
FIG. 22C is a diagram illustrating the shape of the insertion portion in a reference three-dimensional coordinate system XYZk in the diagram illustrating the shape of the insertion portion displayed in the display region of the monitor in FIG. 20.
Figure 23A:
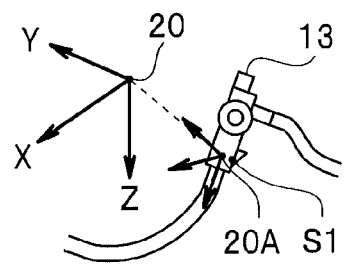
FIG. 23A is a diagram illustrating the position of the operation portion different from FIG. 22A in the diagram illustrating the shape of the insertion portion displayed in the display region of the monitor in FIG. 20.
Figure 23B:
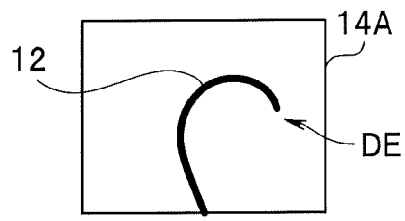
FIG. 23B is a diagram illustrating the shape of the insertion portion different from FIG. 22B in the three-dimensional coordinate system XYZ1 whose origin is the position of the FBG sensor section in the diagram illustrating the shape of the insertion portion displayed in the display region of the monitor in FIG. 20.
Figure 23C:
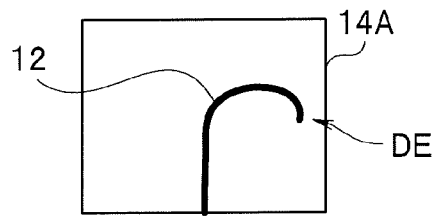
FIG. 23C is a diagram illustrating the shape of the insertion portion different from FIG. 22C in the reference three-dimensional coordinate system XYZk in the diagram illustrating the shape of the insertion portion displayed in the display region of the monitor in FIG. 20.
Figure 24A:
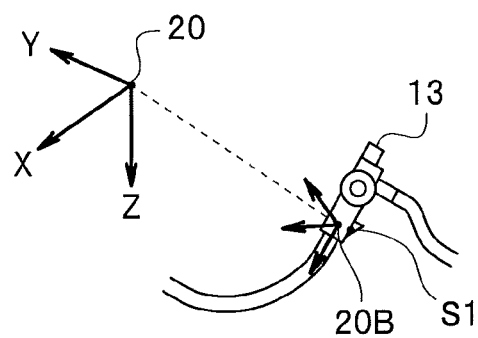
FIG. 24A is a diagram illustrating the position of the operation portion different from FIG. 22A and FIG. 23A in the diagram illustrating the shape of the insertion portion displayed in the display region of the monitor in FIG. 20.
Figure 24B:
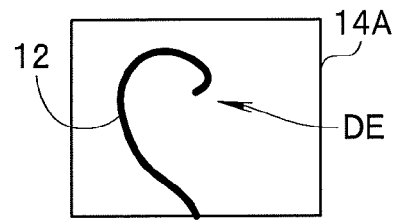
FIG. 24B is a diagram illustrating the shape of the insertion portion different from FIG. 22B and FIG. 23B in the three-dimensional coordinate system XYZ1 whose origin is the position of the FBG sensor section in the diagram illustrating the shape of the insertion portion displayed in the display region of the monitor in FIG. 20.
Figure 24C:
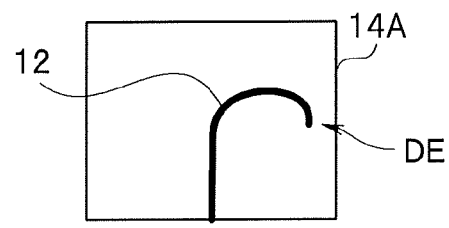
FIG. 24C is a diagram illustrating the shape of the insertion portion different from FIG. 22C and FIG. 23C in the reference three-dimensional coordinate system XYZk in the diagram illustrating the shape of the insertion portion displayed in the display region of the monitor in FIG. 20.

Here, FIG. 22, FIG. 23 and FIG. 24 are diagrams illustrating the shape of the insertion portion 12 displayed in the display region 14A of the monitor 14 when the operation portion 13 moves, FIGS. 22A to 24A illustrate the position of the operation portion 13, FIGS. 22B to 24B illustrate the shape of the insertion portion 12 according to the three-dimensional coordinate system XYZ1 whose origin is the position S1 of the FBG sensor section and FIGS. 22C to 24C illustrate the shape of the insertion portion 12 according to the reference three-dimensional coordinate system XYZk. In FIG. 22, FIG. 23 and FIG. 24, suppose the insertion portion 12 inserted in the examinee 11 is not moving.

At the position of the operation portion 13 shown in FIG. 22A, suppose the operator has pressed the switch disposed in the operation portion. The medical instrument 1 sets the reference three-dimensional coordinate system XYZk based on the orientation of the position sensor assuming the position 20 of the operation portion 13 when the switch is pressed as a reference point.

As shown in FIG. 22B and FIG. 22C, when the switch is pressed, the shape of the insertion portion 12 according to the three-dimensional coordinate system XYZ1 and the shape of the insertion portion 12 according to the reference three-dimensional coordinate system XYZk are the same.

However, when the operation portion 13 moves to a position 20A shown in FIG. 23A and a position 20B shown in FIG. 24 and the orientation of the operation portion 13 changes, the shape of the insertion portion 12 according to the three-dimensional coordinate system XYZ1 shown in FIG. 23B and FIG. 24B changes as the operation portion 13 moves or changes.

On the contrary, the shape of the insertion portion 12 according to the three-dimensional coordinate system XYZk shown in FIG. 23C and FIG. 24C remains stable without being affected by the movement/change of the operation portion 13.

As described above, the medical instrument 1C can detect movement and rotation from the position and orientation of the reference point 20 through the movement sensors, and can thereby transform the shape of the insertion portion 12 calculated according to the first three-dimensional coordinate system XYZ1 whose origin is the unstable position S1 of the FBG sensor sections into a shape display based on the reference three-dimensional coordinate system XYZk having a fixed origin, in other words, from a fixed viewpoint, and can display a stable shape.

The medical instrument 1C of the present embodiment uses the probe made up of the three optical fiber sensors 2A, 2B and 2C to measure the three-dimensional shape of the insertion portion 12, but the number of optical fiber sensors can be any number equal to 3 or more. For example, a probe made up of four optical fiber sensors may be used to improve the measuring accuracy.

Furthermore, to measure a longer range, for example, a probe made up of a number of optical fiber sensors, which is a multiple of 3 may be used. That is, a probe in which regions where the FBG sensor sections 3 are formed using a plurality of sets of three optical fiber sensors are shifted from each other, may be disposed in the longitudinal direction of the insertion portion 12.

Furthermore, the medical instrument 1 of the present embodiment can also use an optical fiber sensor according to a wavelength division multiplexing (WDM) scheme.

Furthermore, instead of the optical fiber sensor 2, a distortion gauge or the like may be used as the distortion detecting means to detect deformation of each section of the insertion portion 12.

Fourth Embodiment

Hereinafter, a medical instrument 1D according to a fourth embodiment of the present invention will be described with reference to the accompanying drawings. Since the configuration and operation of the medical instrument 1D are similar to those of the medical instrument 1C of the third embodiment, the same components will be assigned the same reference numerals and descriptions thereof will be omitted.

Figure 25:
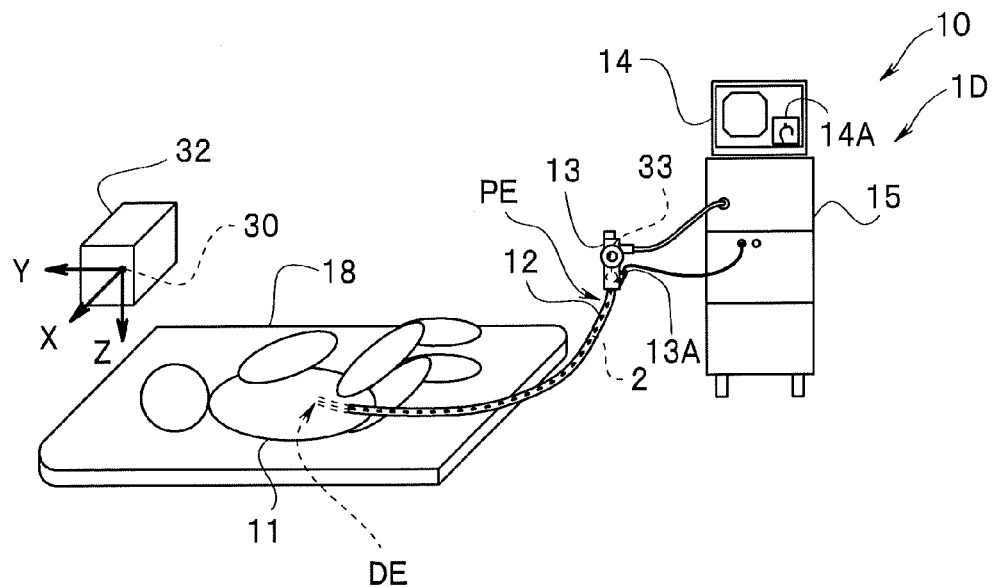
FIG. 25 is a diagram illustrating a situation in which a medical instrument according to a fourth embodiment is used.
Figure 26:
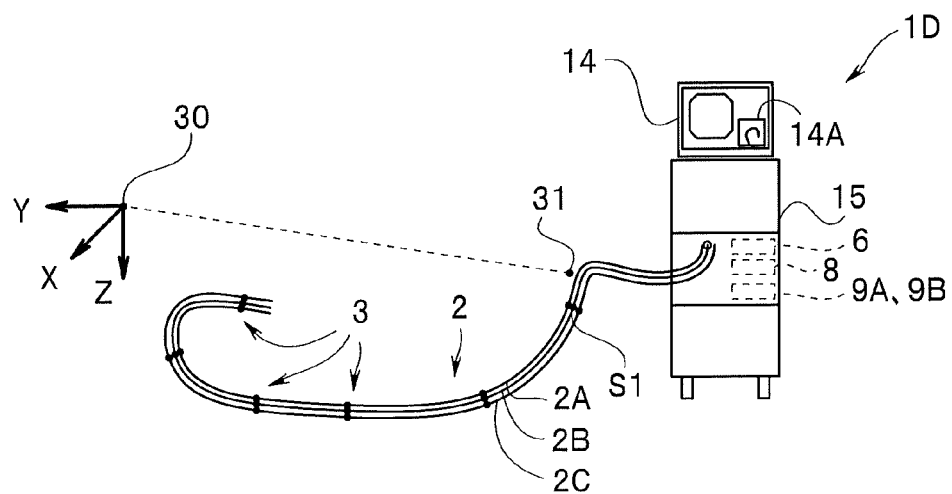
FIG. 26 is a diagram illustrating a configuration of the medical instrument according to the fourth embodiment.

FIG. 25 is a diagram illustrating a situation in which the medical instrument according to the fourth embodiment is used and FIG. 26 is a diagram illustrating a configuration of the medical instrument according to the fourth embodiment.

As shown in FIG. 25, the medical instrument 1D of the present embodiment has a magnetic field generating section 32 which is magnetic field generating means for generating a magnetic field and a magnetic field sensor 33 is disposed in the operation portion 13. The magnetic field sensor 33 is a three-axis magnetic field sensor using an MR sensor, Hall device, coil or the like.

The magnetic field generating section 32 is disposed near a bed 18 which is an inspection stand on which the examinee 11 lies and the position 30 of the magnetic field generating section 32 is fixed at least during display processing of the insertion portion 12 by the medical instrument 1D.

The magnetic field generating section 32 generates, for example, AC magnetic fields of different frequencies from a three-axis magnetic field generation coil. The magnetic field sensor 33 can detect a position of the magnetic field generating section 32 relative to the position 30 by distinctively detecting a plurality of AC magnetic fields of different frequencies.

Since the positional relationship between a position 31 of the magnetic field sensor 33 and a position S1 of the FBG sensor section 3 is fixed and known, it is possible to obtain a correlation between the position S1 of the FBG sensor section 3 and the position 30 of the magnetic field generating section 32.

Thus, the medical instrument 1D can transform coordinates of the first three-dimensional coordinate system XYZ1 whose origin is the position S1 of the FBG sensor sections 3 into coordinates of the reference three-dimensional coordinate system XYZk whose reference point is the position 30 of the magnetic field generating section 32. Since the position 30 of the magnetic field generating section 32 is fixed, the medical instrument 1D can stably display the shape of the insertion portion 12.

Furthermore, when the magnetic field generating section 32 and the bed 18 are arranged such that the XY plane of the reference three-dimensional coordinate system XYZk is parallel to the plane of the bed 18, and the width direction of the bed 18 is parallel to the X-axis of the reference three-dimensional coordinate system XYZk, the medical instrument 1D can calculate the two-dimensional shape resulting from projecting the three-dimensional shape of the insertion portion 12 onto the plane of the bed 18 and display the two-dimensional shape on the monitor 14.

Furthermore, the shape of the three-dimensional shape of the insertion portion 12 projected onto the YZ plane of the reference three-dimensional coordinate system XYZk becomes the shape of the insertion portion 12 when the examinee 11 lying in a lateral position is viewed from the front of the body shown in FIG. 25. Thus, with the medical instrument 1D, the operator can observe the shape of the insertion portion 12 in the body cavity of the examinee 11 from an arbitrary direction by operating the input section 17.

That is, since the positional relationship between the bed 18 and the magnetic field generating section 32 does not change during inspection, the medical instrument 1D in the above configuration can transform coordinates of the shape of the insertion portion 12 into coordinates of a stable second reference coordinate system with reference to the bed 18 from the relative positional relationship and display the shape.

Fifth Embodiment

Hereinafter, a medical instrument 1E according to a fifth embodiment of the present invention will be described with reference to the accompanying drawings. Since the configuration and operation of the medical instrument 1E are similar to those of the medical instrument 1D of the fourth embodiment, the same components will be assigned the same reference numerals and descriptions thereof will be omitted.

Figure 27:
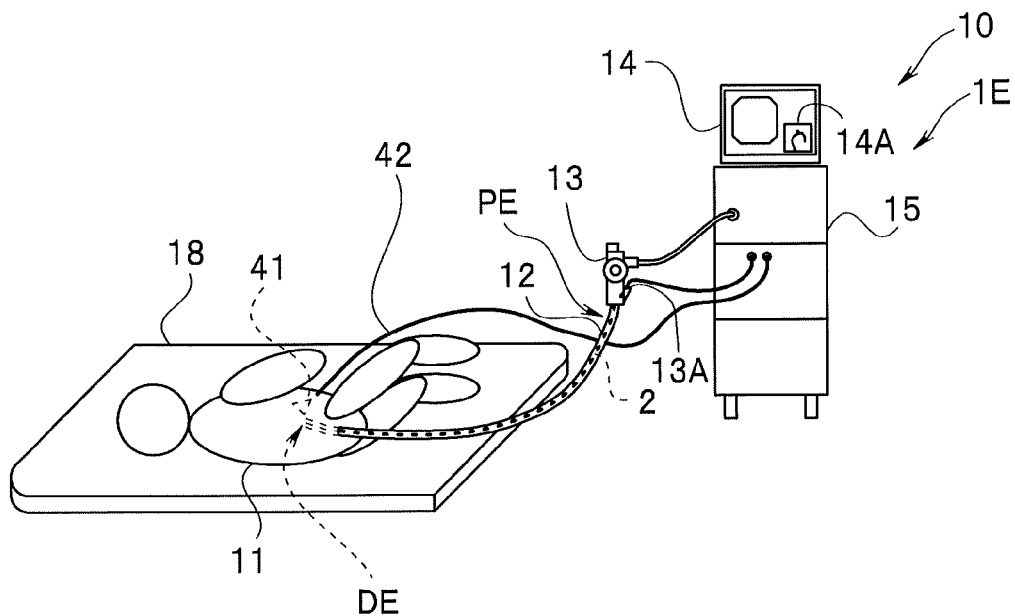
FIG. 27 is a diagram illustrating a situation in which a medical instrument according to a fifth embodiment is used.
Figure 28:
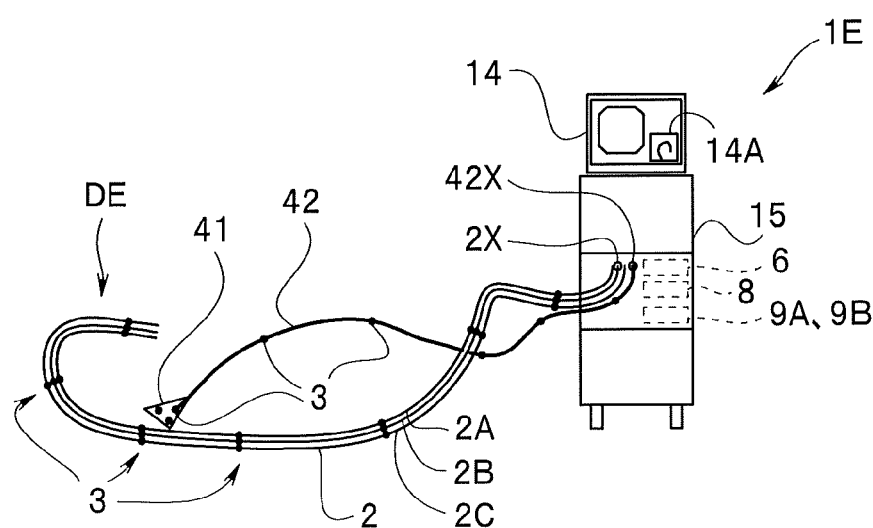
FIG. 28 is a diagram illustrating a configuration of the medical instrument according to the fifth embodiment.

FIG. 27 is a diagram illustrating a situation in which the medical instrument according to the fifth embodiment is used and FIG. 28 is a diagram illustrating a configuration of the medical instrument according to the fifth embodiment.

As shown in FIG. 28, in the medical instrument 1E of the present embodiment, a first sensor probe is the optical fiber sensor 2 in which the FBG sensor sections 3 are formed up to the vicinity of a connection portion 2X with the main unit 15. Thus, the medical instrument 1E can set the main unit 15, for example, the connection portion 2X as the origin of the first three-dimensional coordinate system XYZ1.

Furthermore, the medical instrument 1E includes an optical fiber sensor 42 which is a second sensor probe with a marker portion 41 attached to one end thereof and the other end of the optical fiber sensor 42 provided with the marker portion 41 is connected to the main unit 15 at a connection portion 42X. Since the connection portion 2X and the connection portion 42X are fixed to the main unit 15, the correlation between the connection portion 2X and the connection portion 42X is fixed and known.

Thus, the medical instrument 1E can transform first coordinates of the FBG sensor sections 3 according to the first coordinate system using the connection portion 2X as the origin of the first three-dimensional coordinate system XYZ1 into coordinates of the reference three-dimensional coordinate system XYZk using the marker portion 41 as the origin.

Figure 29A:
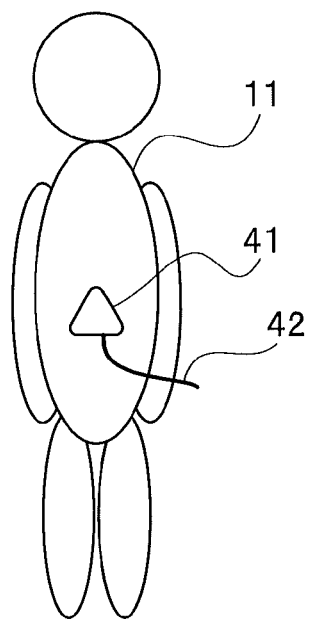
FIG. 29A is a diagram illustrating a marker portion of the medical instrument of the fifth embodiment.

Here, FIG. 29A is a diagram illustrating the marker portion of the medical instrument of the fifth embodiment. Furthermore, FIG. 29B is an enlarged view of the marker portion in FIG. 29A.

As shown in FIG. 29A, the marker portion 41 is pasted and fixed to the outer surface of the examinee 11, for example, the abdomen. The examinee may also wear clothes to which the marker portion 41 is attached.

Figure 29B:
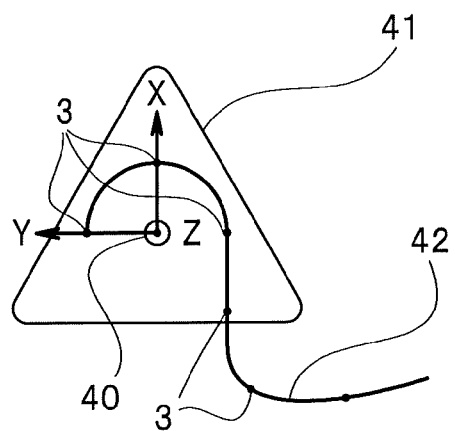
FIG. 29B is an enlarged view of the marker portion in FIG. 29A.

As shown in FIG. 29B, the marker portion 41 has at least three FBG sensor sections 3 on the one end side of the optical fiber sensor 42. Thus, the marker portion 41 can define a reference plane including the three FBG sensor sections 3. The relationship between the reference plane and the examinee 11 is fixed and known.

The medical instrument 1E in the above configuration sets a reference point 40 based on the reference plane defined by the marker portion 41 and sets the reference three-dimensional coordinate system XYZk, and can thereby transform coordinates from the first three-dimensional coordinate system XYZ1 whose origin is the position S1 of the FBG sensor sections 3 to the reference three-dimensional coordinate system XYZk.

Here, the positions of the three FBG sensor sections 3 of the marker portion 41 are expressed by the following (Equation 9).

$$\vec{P}_1 = (x_1, y_1, z_1)$$

$$\vec{P}_2 = (x_2, y_2, z_2)$$

$$\vec{P}_3 = (x_3, y_3, z_3) \quad \text{(Equation 9)}$$

The center position 40 of the reference three-dimensional coordinate system XYZk can be calculated according to the following (Equation 10).

$$\vec{O} = \left( \frac{(x_1 + x_3)}{2}, \frac{(y_1 + y_3)}{2}, \frac{(z_1 + z_3)}{2} \right) \quad \text{(Equation 10)}$$

A rotation matrix R between the first three-dimensional coordinate system XYZ1 using the optical fiber sensor 2 which is the first probe as a reference and the reference three-dimensional coordinate system XYZk is calculated according to the following (Equation 11).

$$R = \begin{pmatrix} r11 & r12 & r13 \\ r21 & r22 & r23 \\ r31 & r32 & r33 \end{pmatrix} \quad \text{(Equation 11)}$$

A transformation matrix $T_A^B$ whereby the first three-dimensional coordinate system XYZ1 is transformed into the reference three-dimensional coordinate system XYZk from the center position 40 of the reference three-dimensional coordinate system XYZk and the rotation matrix R is the following (Equation 12).

$$T_A^B = \begin{pmatrix} r11 & r12 & r13 & (x1+x3)/2 \\ r21 & r22 & r23 & (y1+y3)/2 \\ r31 & r32 & r33 & (z1+z3)/2 \\ 0 & 0 & 0 & 1 \end{pmatrix} \quad \text{(Equation 12)}$$

Using the above described method, the medical instrument 1E transforms coordinates of the FBG sensor sections 3 formed in the optical fiber sensor 2 which is the first probe into the reference three-dimensional coordinate system XYZk, which is in a relationship fixed to the examinee 11 according to the above described transformation matrix and can display the shape of the insertion portion 12.

The reference three-dimensional coordinate system XYZk uses the plane parallel to the top surface of the abdomen of the examinee 11 as a reference plane, and the medical instrument 1E can thereby stably display an image of the shape of the insertion portion 12 observed from the abdomen side even if the examinee changes his/her posture.

Hereinafter, a medical instrument according to a modification example of the fifth embodiment of the present invention will be described with reference to FIG. 30. Since the configuration and operation of the medical instrument of the present modification example are similar to those of the medical instrument 1E of the fifth embodiment, the same components will be assigned the same reference numerals and descriptions thereof will be omitted.

Figure 30:
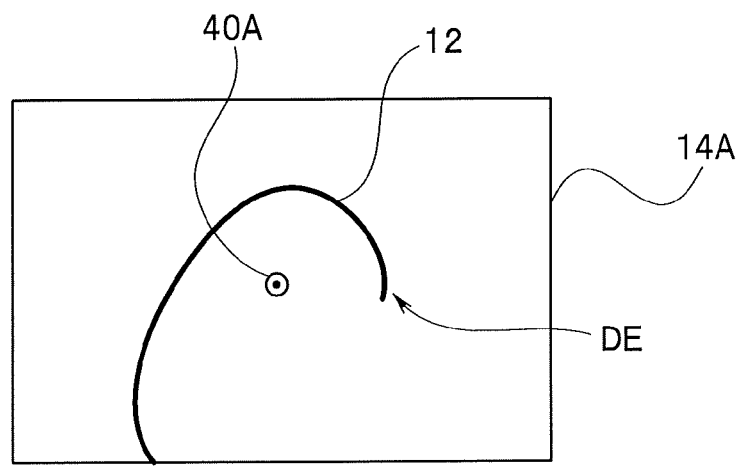
FIG. 30 is a diagram illustrating a display screen of a monitor of a medical instrument according to a modification example of the fifth embodiment.

FIG. 30 is a diagram illustrating a display screen of a monitor of the medical instrument according to the modification example of the fifth embodiment.

The medical instrument of the present modification example can display not only the shape of the insertion portion 12 as shown in FIG. 30 but also, for example, the center position 40 of the marker portion 41 on the display region 14A of the monitor 14.

In the case where the large intestine expands in the body cavity and the endoscope cannot be inserted, there is a technique which suppresses the expansion of the large intestine through manual compression by pressing the surface of the body by hand and inserting the endoscope. However, since the position of the distal end of the endoscope in the body cavity cannot be exactly known, it has been hard to accurately perform manual compression. However, the medical instrument of the present modification example simultaneously displays the marker portion 41 that specifies the region outside the body cavity and the shapes of the marker portion 41 and the insertion portion 12, and thereby a specific position of the insertion portion 12 can be checked from outside the body cavity.

According to the medical instrument of the present modification example, at least one FBG sensor section 3 may be formed for the marker.

Sixth Embodiment

Hereinafter, a medical instrument 1F according to a sixth embodiment of the present invention will be described with reference to the accompanying drawings. Since the configuration and operation of the medical instrument 1F are similar to those of the medical instrument 1E of the fifth embodiment, the same components will be assigned the same reference numerals and descriptions thereof will be omitted.

Figure 31:
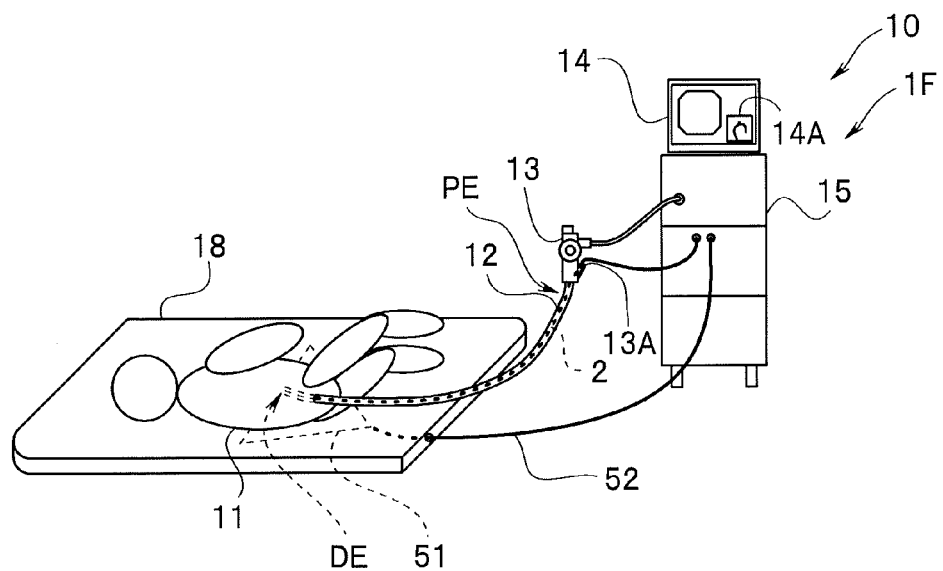
FIG. 31 is a diagram illustrating a situation in which a medical instrument according to a sixth embodiment is used.
Figure 32:
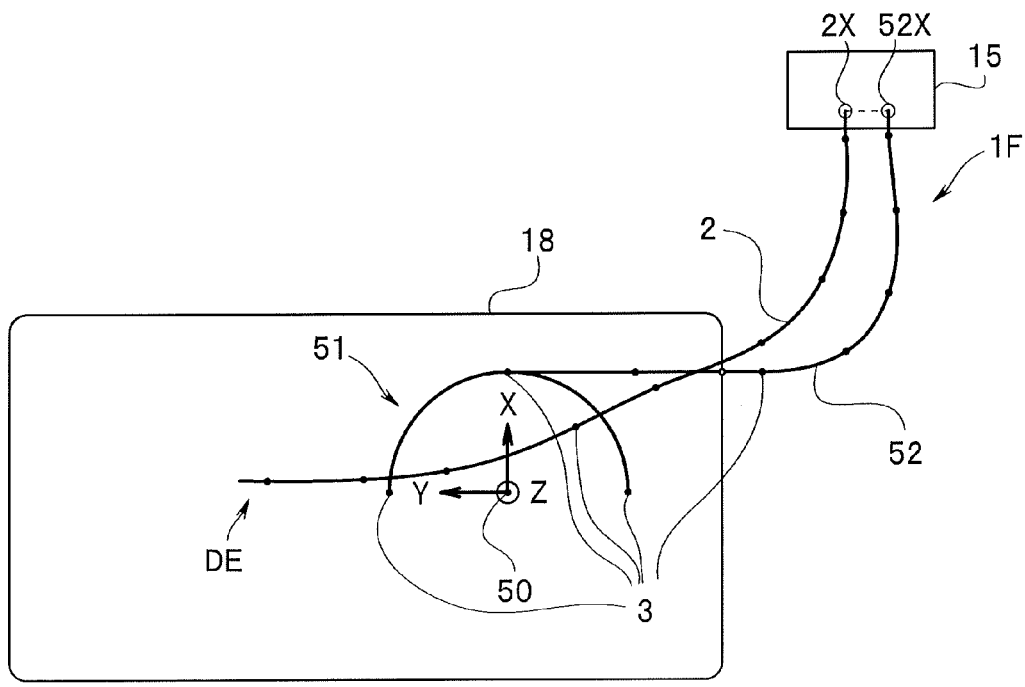
FIG. 32 is a diagram illustrating the medical instrument of the sixth embodiment.

FIG. 31 is a diagram illustrating a situation in which the medical instrument according to the sixth embodiment is used and FIG. 32 is a diagram illustrating a configuration of the medical instrument of the sixth embodiment.

As in the case of the medical instrument 1E, the medical instrument 1F of the present embodiment has an optical fiber sensor 2 which is a first sensor probe and an optical fiber sensor 52 which is a second sensor probe.

The optical fiber sensor 2 is fixed to the main unit 15 at a connection portion 2X and the optical fiber sensor 52 is fixed at a connection portion 52X. The optical fiber sensor 52 has a marker portion 51 in which three or more FBG sensor sections 3 are formed at one end as in the case of the marker portion 51 and the marker portion 51 is fixed to the bed 18 which is an inspection stand on which the examinee lies.

Thus, when the medical instrument 1F sets a reference point using the bed 18 defined by the marker portion 41 as a reference plane and sets a reference three-dimensional coordinate system XYZk, it is possible to transform coordinates from the first three-dimensional coordinate system XYZ1 using the position of the FBG sensor section 3 as the origin into the reference three-dimensional coordinate system XYZk using the surface of the bed 18 as a reference.

Thus, the medical instrument 1F can display an image resulting from projecting the shape of the insertion portion 12 onto the surface (XY plane) of the bed 18 or an image projected onto the YZ plane which is an image of the patient lying on the bed observed from the abdomen side on the monitor 14.

As described above, the medical instrument 1F can transform coordinate values of the first three-dimensional coordinate system XYZ1 using the position of the unstable FBG sensor section 3 as the origin into coordinate values of the reference three-dimensional coordinate system XYZk using the stable surface of the bed 18 as a reference, and can thereby display a stable shape.

Seventh Embodiment

In recent years, endoscopes are widely used in the medical field and industrial field. Endoscopes used in the medical field insert an elongated insertion portion into the body cavity to observe organs in the body cavity or can perform various kinds of treatment using, if necessary, a treatment instrument provided for the endoscope inserted into an insertion channel of the treatment instrument.

Furthermore, endoscopes used in the industrial field insert an elongated insertion portion of the endoscope into a jet engine or pipes in a factory, and can thereby make observations of damages and corrosion in a region to be inspected and perform various kinds of treatment.

Among endoscopes used in the medical field and industrial field, a configuration of endoscope is well known which is provided, on the distal end side in the insertion direction of the insertion portion, with a bending portion which not only helps the insertion portion move ahead in the crooked portion in the tube but also is freely bendable in a plurality of directions to make variable the observation direction of an observation optical system provided at a distal end of the insertion portion in the insertion direction.

Furthermore, regarding portions other than the bending portion of the insertion portion of the endoscope, flexible endoscopes are configured such that even when inserted into a crooked tube, those portions are allowed to bend along the shape of the crooked portion.

In view of such circumstances, Japanese Patent Application Laid-Open Publication No. 2004-251779 discloses a configuration in which an optical fiber where a plurality of known fiber Bragg gratings (hereinafter referred to as "FBG") are formed at a set interval over a total length is inserted over a total length of at least the insertion portion of an endoscope. Using such a configuration, light is inputted into the optical fiber, reflected light reflected by the FBG is detected and the amount of distortion caused by the deformation of the optical fiber in the region in which the FBG is formed is detected and the shape of the insertion portion can thereby be detected. As is generally known, the amount of distortion is detected using reflected light from the FBG by calculating a variation of the frequency from a frequency shift of the wavelength of the reflected light caused by a variation in the wavelength of the reflected light from the FBG, in other words, a variation in the amount of distortion of the optical fiber in the region where the FBG is formed accompanying the deformation.

Such a configuration allows the shape of the insertion portion to be detected and allows the operator to recognize the shape of the insertion portion, and can thereby prevent damages to the insertion portion accompanying the insertion. That is, upon recognizing that the insertion portion is excessively deformed, the operator can stop the progress of the insertion portion, and can thereby prevent damages to the insertion portion.

In addition to the aforementioned FBG, an image pickup unit for picking up an image of the region to be examined and a plurality of light guides (hereinafter, referred to as "LG") for supplying a light source for illuminating the region to be examined are provided in the insertion portion. The image pickup unit and LG constitute heat generating members for generating heat by being driven and through light guiding.

Here, as is generally known, the optical fiber has the property of becoming deformed such as expansion or contraction accompanying a temperature variation. Since the optical fiber becomes deformed by an amount corresponding to each temperature variation, even a temperature variation in units of 0.1° C., the optical fiber may also be used as a thermometer by detecting the amount of deformation.

Figure 33:
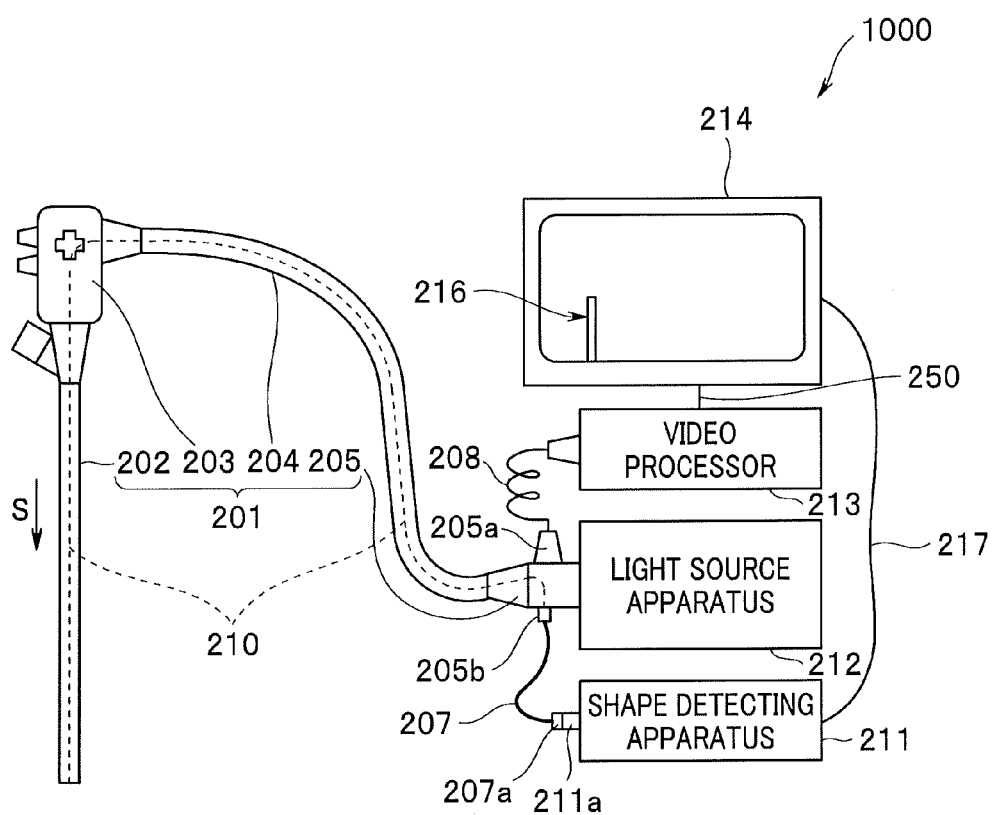
FIG. 33 is a diagram illustrating the endoscope shape detecting system provided with an endoscope illustrating a seventh embodiment.
Figure 34:
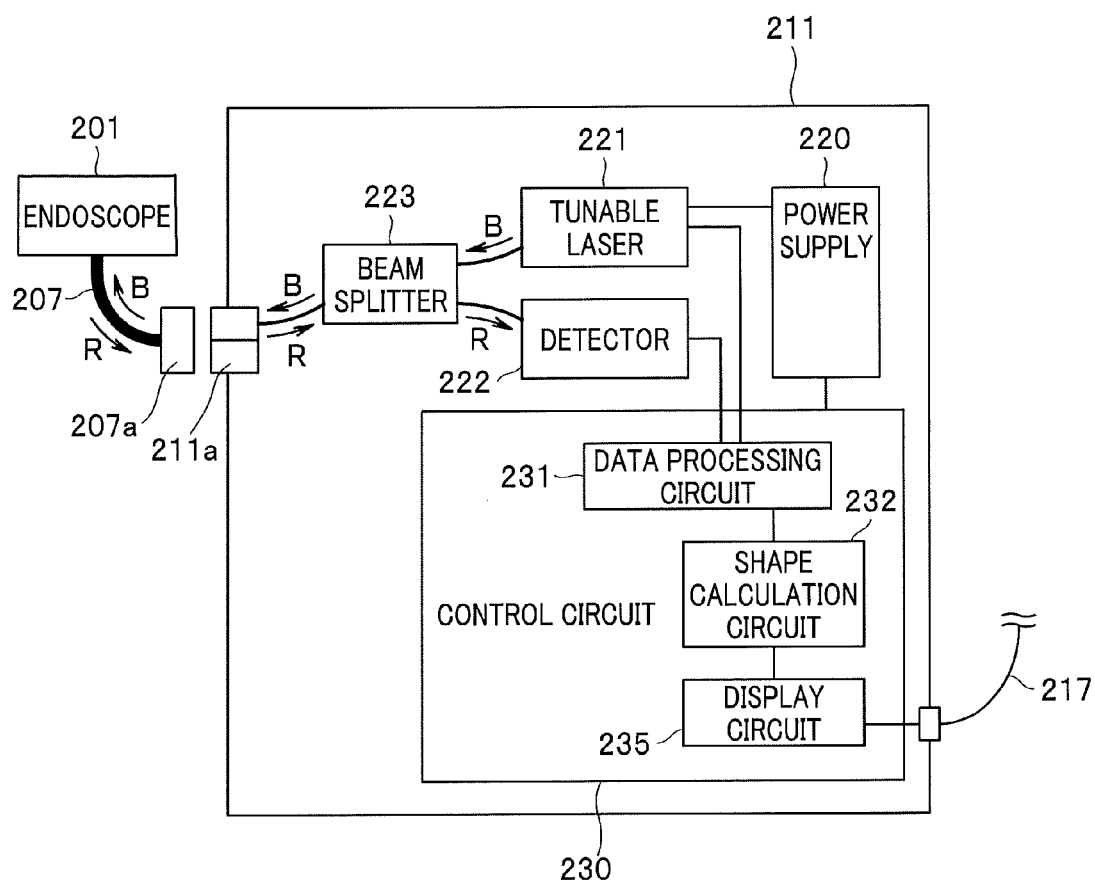
FIG. 34 is a block diagram schematically illustrating a configuration of the shape detecting apparatus in FIG. 33.

FIG. 33 is a diagram illustrating an endoscope shape detecting system provided with an endoscope illustrating the present embodiment and FIG. 34 is a block diagram schematically illustrating a configuration of the shape detecting apparatus in FIG. 33.

As shown in FIG. 33, main parts of the endoscope shape detecting system 1000 are configured by including an endoscope 201, an endoscope shape detecting apparatus (hereinafter, simply referred to as "shape detecting apparatus") 211, a light source apparatus 212, a video processor 213 and a monitor 214.

The main parts of the endoscope 201 are configured by including an insertion portion 202 inserted into a region to be examined, an operation portion 203 provided on a proximal end side of an insertion direction S of the insertion portion 202 (hereinafter, simply referred to as "proximal end side"), a universal cord 204 that extends from the operation portion 203 and an endoscope connector 205 provided at an extending end of the universal cord 204.

Furthermore, an optical fiber 210 for detecting at least the shape of the insertion portion 202 is inserted into the insertion portion 202 of the endoscope 201, the operation portion 203, the universal cord 204 and the endoscope connector 205.

Figure 35:
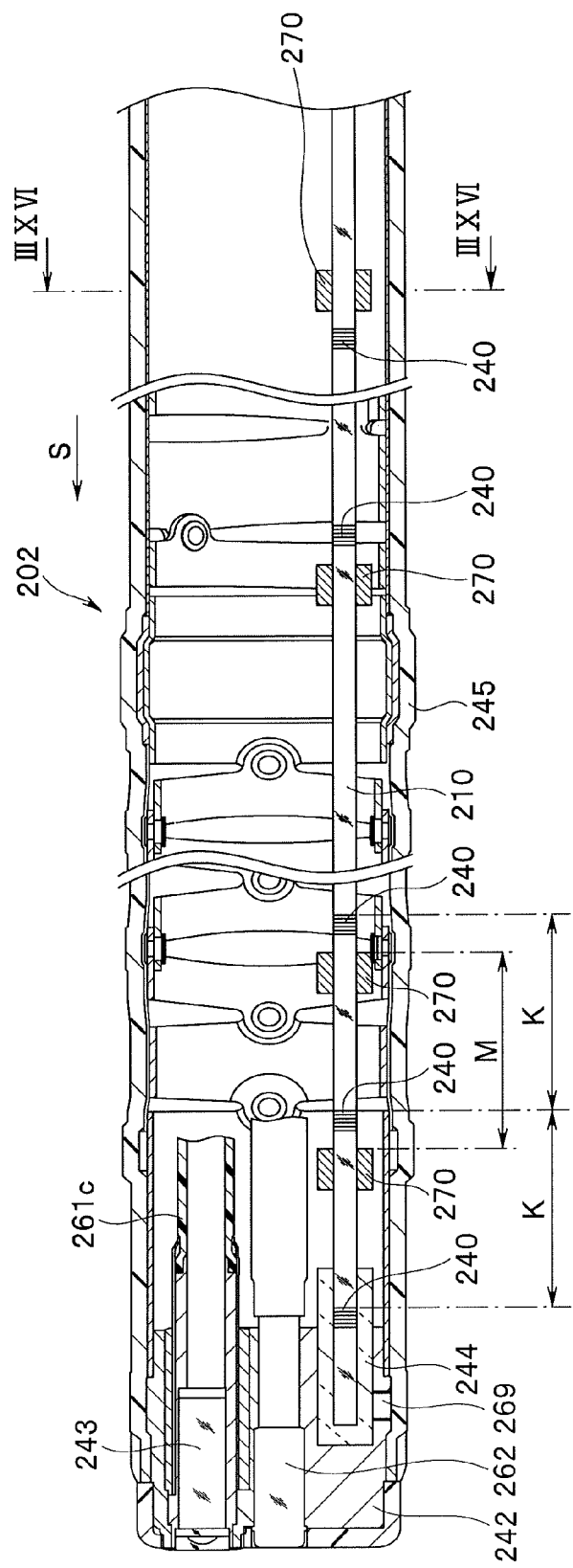
FIG. 35 is a partial cross-sectional view schematically illustrating an internal configuration of the distal end side of the insertion portion in FIG. 33.

As shown in FIG. 35, which will be described later, a plurality of the aforementioned FBGs 240 are formed in the region inserted in at least the insertion portion 202 of the optical fiber 210 at a set interval K along the insertion direction S.

The FBG 240 may also be formed in the regions inserted in the operation portion 203, the universal cord 204 and the endoscope connector 205 of the optical fiber 210.

Furthermore, as shown in FIG. 33, the endoscope connector 205 is connected to the light source apparatus 212 by a connector portion for light source connection (not shown) provided in the endoscope connector 205 being attached to the light source apparatus 212.

The light source apparatus 212 is intended to supply illumination light to, for example, an LG 262 (see FIG. 35), which will be described later, inserted in the endoscope 201. The illumination light supplied to the LG 262 is irradiated from an illumination lens (not shown) provided at a distal end of the insertion direction S of the LG 262 (hereinafter, simply referred to as "distal end") onto a region to be examined on the distal end face on the distal end side of the insertion direction S of the insertion portion 202 (hereinafter, simply referred to as "distal end side").

Furthermore, the endoscope connector 205 is provided with a connector portion 205a and the connector portion 205a is electrically connected to the video processor 213 via a cable 208.

The video processor 213 is intended to perform image pickup control of an image pickup device such as CCD in an image pickup unit 243 (see FIG. 35), which will be described later, provided on the distal end side of the insertion portion 202 via an image pickup cable 261 (see FIG. 36) inserted in the endoscope 201, which will be described later, via the cable 208 and perform image processing or the like on an endoscope image picked up by the image pickup device.

Furthermore, the endoscope connector 205 is provided with a connector portion 205b and the connector portion 205b is connected to the connector portion 211a of the shape detecting apparatus 211 via a cable 207.

A detachable connector portion 207a provided at an extending end of the cable 207 is detachably attached to the connector portion 211a. The proximal end side of the optical fiber 210 inserted in the endoscope 201 is connected to the detachable connector portion 207a.

The monitor 214 is electrically connected to the video processor 213 via a cable 250 and is also electrically connected to the shape detecting apparatus 211 via a cable 217.

Furthermore, the monitor 214 displays not only an endoscope image subjected to image processing by the video processor 213 but also a scope model 216 illustrating the shape of the insertion portion 202 outputted from the shape detecting apparatus 211.

As shown in FIG. 34, main parts of the shape detecting apparatus 211 are configured by including a power supply 220, a tunable laser 221 which is a light input section, a detector 222, a beam splitter 223 and a control circuit 230.

The power supply 220 is intended to supply power to the tunable laser 221 and the control circuit 230, and the tunable laser 221 which is a wavelength variable laser is intended to input laser light B to the optical fiber 210 from the proximal end side of the optical fiber 210 via the beam splitter 223, the connector portion 211a and the detachable connector portion 207a.

Furthermore, the detector 222 is intended to detect reflected light R from each FBG 240 of the laser light B inputted to the optical fiber 210 via the detachable connector portion 207*a*, the connector portion 211*a* and the beam splitter 223.

Main parts of the control circuit 230 are configured by including a data processing circuit 231 which is an amount of distortion measuring section, a shape calculation circuit 232 which is a shape calculation section and a display circuit 235.

The data processing circuit 231 is electrically connected to the tunable laser 221 and the detector 222, and is intended to measure an amount of distortion of each FBG 240 from the reflected light R detected by the detector 222.

The shape calculation circuit 232 is electrically connected to the data processing circuit 231 and the display circuit 235, and is intended to calculate the shape of the insertion portion 202 from the amount of distortion of each FBG 240 measured by the data processing circuit 231.

The display circuit 235 is intended to display the shape of the insertion portion 202 calculated by the shape calculation circuit 232 on the monitor 214 as the scope model 216.

Figure 36:
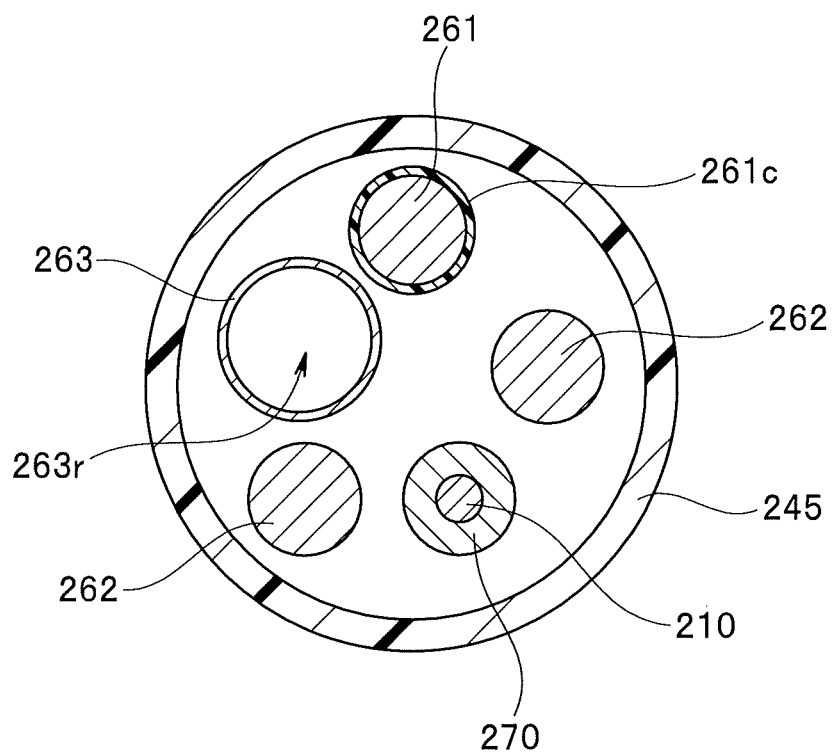
FIG. 36 is a cross-sectional view along the line IIIXVI-IIIXVI in FIG. 35.

Next, a schematic internal configuration on the distal end side of the insertion portion 202 of the endoscope 201 in FIG. 33 will be illustrated using FIG. 35 and FIG. 36. FIG. 35 is a partial cross-sectional view schematically illustrating an internal configuration of the distal end side of the insertion portion in FIG. 33 and FIG. 36 is a cross-sectional view along the line IIIXVI-IIIXVI in FIG. 35.

As shown in FIG. 35, the optical fiber 210 is inserted in the interior covered with a skin 245 on the distal end side of the insertion portion 202 and the distal end side of the optical fiber 210 is fixed to a distal end rigid portion 242 provided inside at the distal end of the insertion portion 202 via a holder 244 which is a fixing member. The holder 244 is fixed to the distal end rigid portion 242 by a stopper screw 269 inserted from the outer circumferential direction of the insertion portion 202.

Furthermore, the holder 244 is formed of a material of low thermal conductivity such as a heat insulator or foamed material. Thus, the holder 244 constitutes a reducing member that reduces heat transmitted to the optical fiber 210 from a heat generating section such as the image pickup unit 243, which will be described later, or LG 262 via the holder 244 and the distal end rigid portion 242 and reduces the amount of distortion caused by heat in the FBGs 240 formed in the optical fiber 210.

Furthermore, as shown in FIG. 35, a plurality of, for example, spacer-shaped protective members 270 are fixed to cover the outer perimeter of the optical fiber 210 at a set interval M along the insertion direction S.

As shown in FIG. 35, the protective members 270 are fixed at positions of the optical fiber 210 avoiding the plurality of FBGs 240 formed at a set interval K along the insertion direction S.

This is because if the protective members 270 are formed at the same positions as those of the FBGs 240, when the optical fiber 210 becomes deformed, it is hard for the FBGs 240 protected by the protective members 270 to be distorted, which may prevent the amount of distortion of the FBGs 240 from being detected accurately.

The protective members 270 prevent the optical fiber 210 from contacting the LG 262 and the image pickup unit 243. To be more specific, the protective members 270 prevent the optical fiber 210 from contacting the LG 262 and the image pickup unit 243 or the like due to the warpage of the insertion portion 202 or bending of the bending portion (not shown) provided in the insertion portion 202 and thereby constitutes a reducing member that reduces heat transmitted from the heat generating section such as the image pickup unit 243 or LG 262 to the optical fiber 210 as a result of the heat generating section contacting the optical fiber 210 due to warpage or bending and reduces the amount of distortion generated by heat in the FBGs 240 formed in the optical fiber 210.

Furthermore, as shown in FIG. 35 and FIG. 36, in addition to the optical fiber 210, the image pickup cable 261 coated with a blade 261*c*, the LG 262, and a channel tube 263 in which a fluid supply channel 263*r* is formed are inserted in the interior covered with the skin 245 of the insertion portion 202.

The distal end rigid portion 242 is provided with the image pickup unit 243 and the distal end of the image pickup cable 261 is electrically connected to the image pickup unit 243. Furthermore, the distal end of the LG 262 is fixed to the distal end rigid portion 242 so as to be proximate to an illumination lens (not shown) provided in the distal end rigid portion 242 and so as to be positioned opposed to the illumination lens. Furthermore, the channel 263*r* is open to the distal end face of the distal end rigid portion 242. Since the image pickup unit 243 generates heat by being driven and the LG 262 also generates heat through light guiding, the image pickup unit 243 and the LG 262 constitute heat generating sections of the present embodiment.

Other members are also inserted and various members are disposed in the insertion portion 202, but these are well known, and therefore descriptions thereof will be omitted.

Thus, the present embodiment has shown that the fixing member that fixes the distal end side of the optical fiber 210 to the distal end rigid portion 242 is formed of a material of low thermal conductivity such as a heat insulator or foamed material.

Accordingly, the holder 244 can reduce heat dissipated from the image pickup unit 243 and LG 262 transmitted to the optical fiber 210 from the image pickup unit 243 or LG 262 or the like via the holder 244 and distal end rigid portion 242, and can thereby reduce the amount of distortion generated in the FBG 240 caused by heat deformation of the optical fiber 210 due to heat compared with the conventional arts. That is, it is possible to prevent the data processing circuit 231 from measuring the amount of distortion of each FBG 240 more than the amount of distortion corresponding to the amount of bending of the optical fiber 210 caused by the deformation of the insertion portion 202 under the influence of heat.

Furthermore, the present embodiment has shown that a plurality of protective members 270 are fixed to cover the outer perimeter of the optical fiber 210 along the insertion direction S at the set interval M.

Thus, the protective members 270 prevent the optical fiber 210 from contacting the LG 262 or image pickup unit 243 or the like due to warpage of the insertion portion 202 or bending of the bending portion (not shown) provided in the insertion portion 202, and can thereby reduce heat dissipated from the image pickup unit 243 or LG 262 or the like transmitted to the optical fiber 210 from the image pickup unit 243 or LG 262 or the like, and can thereby reduce the amount of distortion generated in the FBG 240 due to heat deformation of the optical fiber 210 compared with the conventional arts.

That is, it is possible to prevent the data processing circuit 231 from measuring the amount of distortion of each FBG 240 more than the amount of distortion corresponding to the amount of bending of the optical fiber 210 caused by the deformation of the insertion portion 202 under the influence of heat.

As described so far, it is possible to provide the endoscope 201 and the endoscope shape detecting system 1000 capable of improving the shape detection accuracy of the insertion portion 202 by reducing deformation of the optical fiber 210 due to the heat transmitted to the optical fiber 210 from the heat generating member.

Hereinafter, modification examples will be illustrated.

The present embodiment has shown that the holder 244 and the protective members 270 can reduce the deformation of the optical fiber 210 due to heat transmitted from the image pickup unit 243 or LG 262, but the present invention is not limited thereto, and adopting any one of forming the holder 244 of a material of low thermal conductivity and providing the protective members 270 can reduce the deformation of the optical fiber 210 due to heat transmitted from the image pickup unit 243 or LG 262 compared with the conventional arts, though the effect is smaller than the present embodiment.

Figure 37:
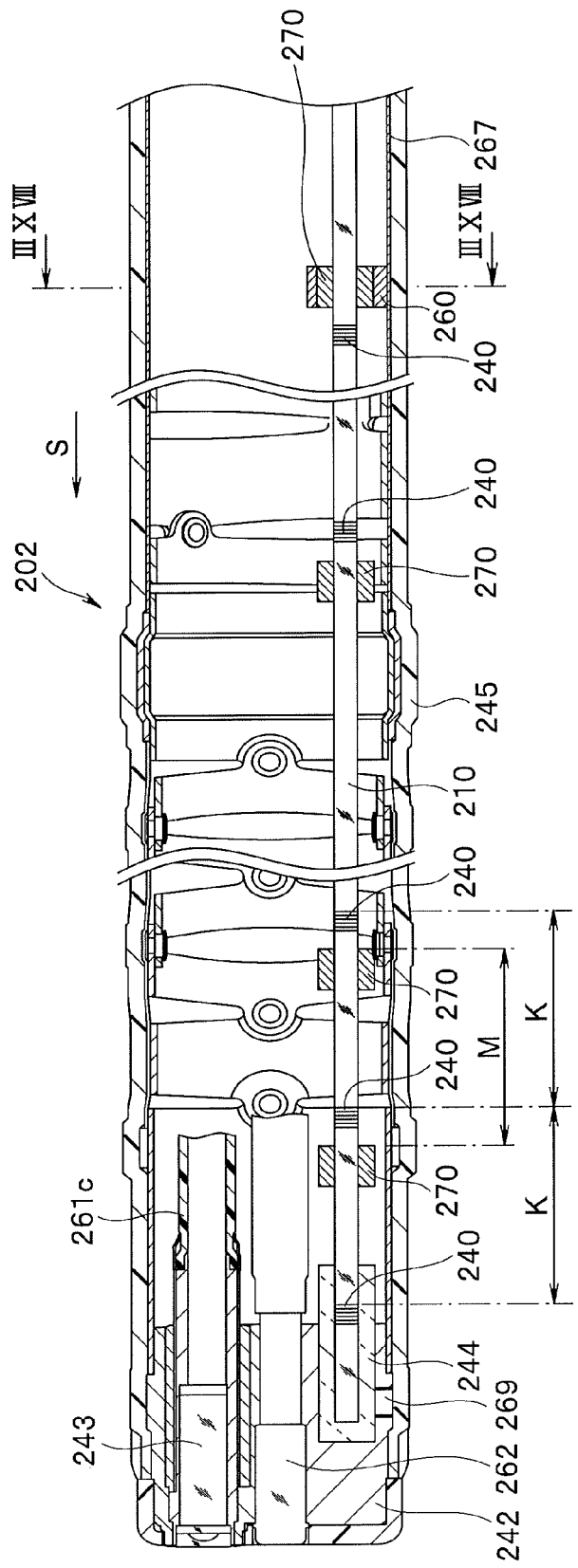
FIG. 37 is a partial cross-sectional view schematically illustrating a configuration of a modification example of the interior on the distal end side of the insertion portion in FIG. 33.
Figure 38:
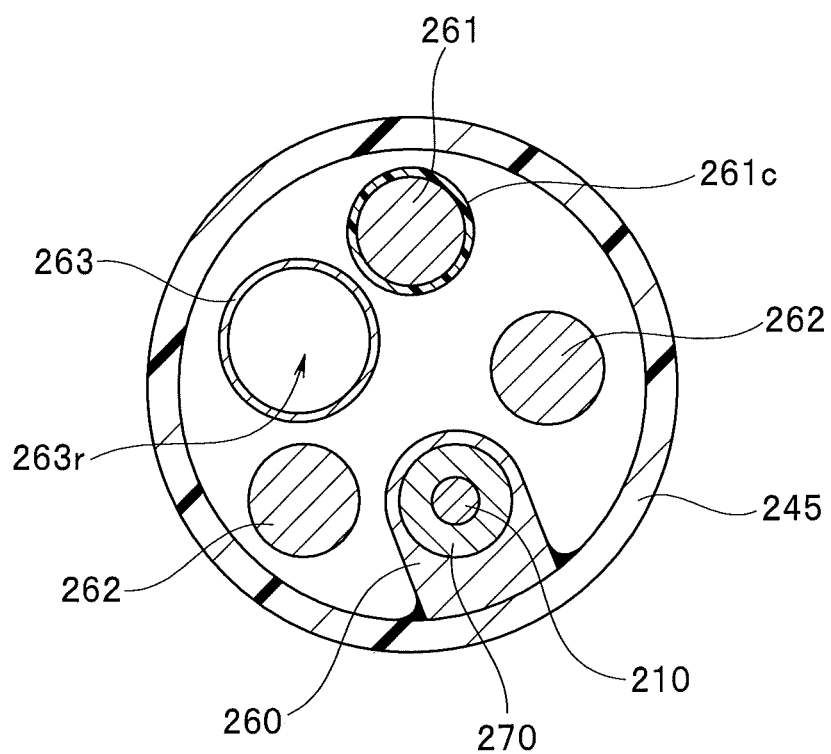
FIG. 38 is a cross-sectional view along the line IIIXVIII-IIIXVIII in FIG. 37.

Another modification example will be illustrated using FIG. 37 and FIG. 38. FIG. 37 is a partial cross-sectional view schematically illustrating a configuration of a modification example of the interior on the distal end side of the insertion portion in FIG. 33 and FIG. 38 is a cross-sectional view along the line IIIXVIII-IIIXVIII in FIG. 37.

The present embodiment has shown that the holder 244 is formed of a material of low thermal conductivity such as a heat insulator or foamed material to reduce deformation of the optical fiber 210 due to heat transmitted from the image pickup unit 243 or LG 262 and a plurality of protective members 270 are fixed to the optical fiber 210 at the set interval M.

Moreover, a support member 260 that supports part of the optical fiber 210 may also be provided on the inner surface of the insertion portion 202 to reduce deformation of the optical fiber 210 due to heat transmitted from the image pickup unit 243 or LG 262.

To be more specific, as shown in FIG. 37 and FIG. 38, part of the optical fiber 210 is covered and supported with a blade 267 provided on the inner surface of the skin 245 of the insertion portion 202 to position the optical fiber 210 in the diameter direction and a support member 260 is provided to prevent the optical fiber 210 from contacting the LG 262 or image pickup unit 243. The support member 260 also supports a region other than the positions at which the FBGs 240 of the optical fiber 210 are formed for the purpose of accurately detecting the amount of distortion of the FBGs 240.

The support member 260 regulates the movement of the optical fiber 210 in the diameter direction, prevents the optical fiber 210 from contacting the LG 262 or image pickup unit 243 or the like due to warpage of the insertion portion 202 or bending of the bending portion (not shown) provided in the insertion portion 202, and thereby constitutes a reducing member that reduces heat transmitted from the heat generating section such as the image pickup unit 243 or LG 262 to the optical fiber 210 and reduces the amount of distortion generated by heat in the FBGs 240 formed in the optical fiber 210.

Thus, the support member 260 regulates the movement of the optical fiber 210 in the diameter direction, prevents the optical fiber 210 from contacting the LG 262, image pickup unit 243 or the like due to warpage of the insertion portion 202 or bending of the bending portion (not shown) provided in the insertion portion 202, and can thereby further reduce heat transmitted from the heat generating section such as the image pickup unit 243 or LG 262 to the optical fiber 210 and dissipated from the image pickup unit 243 or LG 262 and thereby reduce the amount of distortion generated in the FBGs 240 accompanying heat deformation of the optical fiber 210 compared with the present embodiment.

That is, it is possible to prevent the data processing circuit 231 from measuring the amount of distortion of each FBG 240 more than the amount of distortion corresponding to the amount of bending of the optical fiber 210 caused by the deformation of the insertion portion 202 under the influence of heat. The rest of the configuration and effects are similar to those of the aforementioned present embodiment.

Furthermore, FIG. 37 and FIG. 38 have shown that the deformation of the optical fiber 210 due to heat transmitted from the image pickup unit 243 or LG 262 is reduced by the holder 244, the protective members 270 and the support member 260, but the present invention is not limited thereto and providing only the support member 260 can also reduce the deformation of the optical fiber 210 due to heat transmitted from the image pickup unit 243 or LG 262 compared with the conventional arts, though the effect is smaller than that of the configuration shown in FIG. 37 and FIG. 38.

Figure 39:
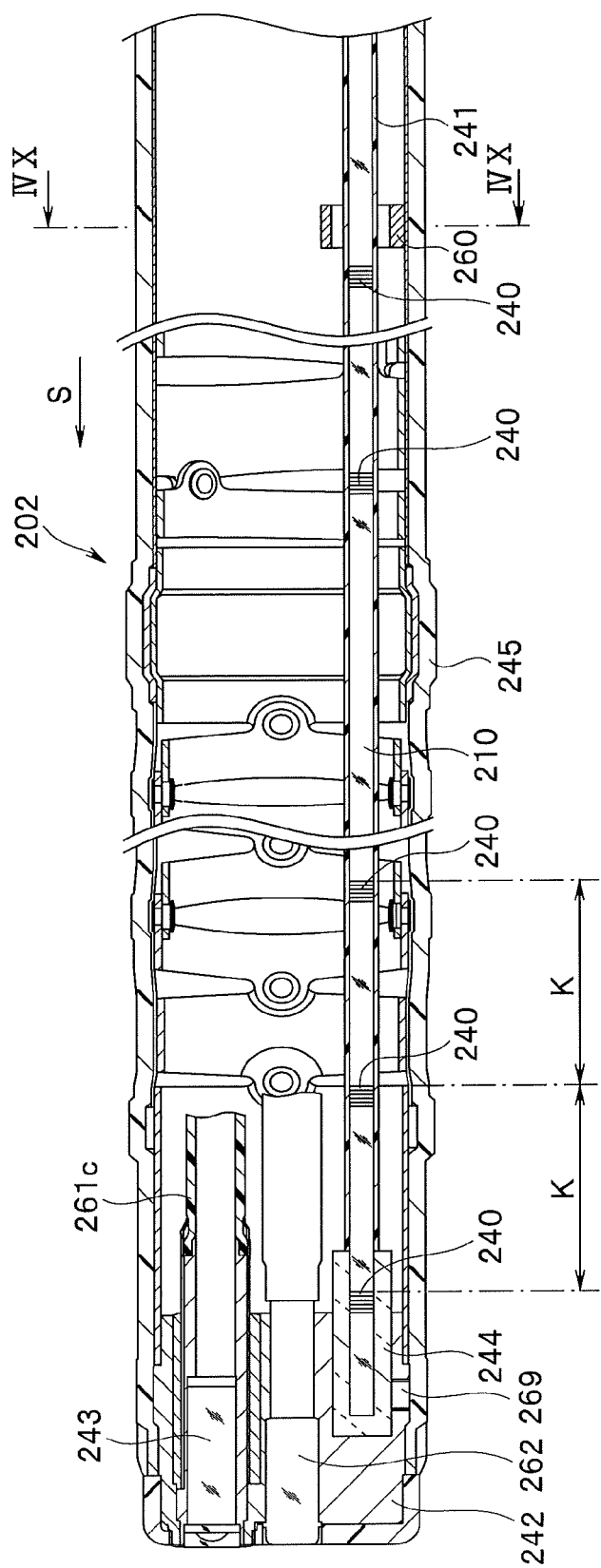
FIG. 39 is a partial cross-sectional view schematically illustrating a configuration of a modification example different from FIG. 37 of the interior on the distal end side of the insertion portion in FIG. 33.
Figure 40:
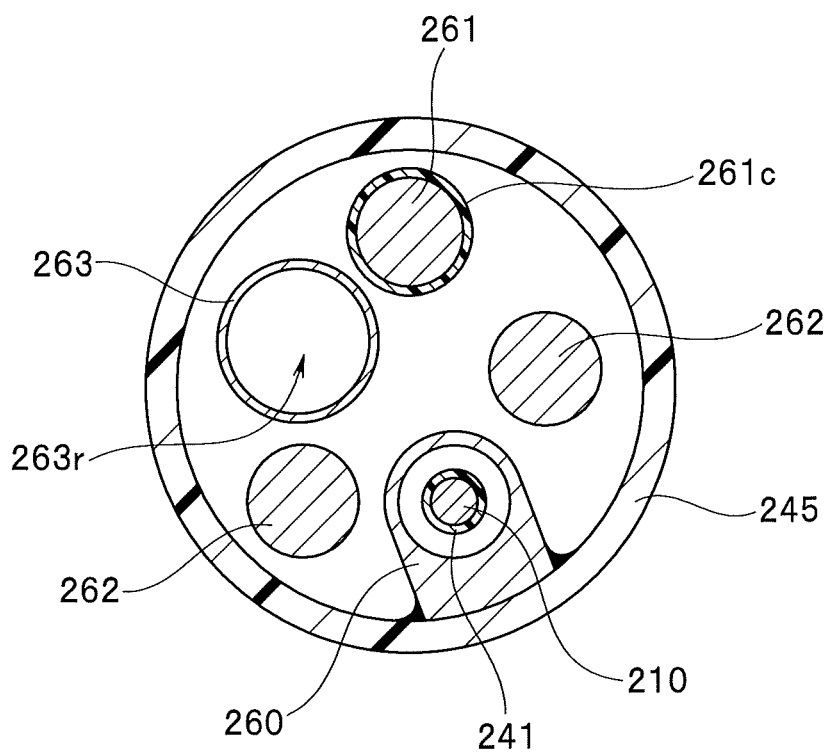
FIG. 40 is a cross-sectional view along the line IVX-IVX in FIG. 39.

Furthermore, another modification example will be illustrated using FIG. 39 and FIG. 40. FIG. 39 is a partial cross-sectional view schematically illustrating a configuration of a modification example different from FIG. 37 of the interior on the distal end side of the insertion portion in FIG. 33 and FIG. 40 is a cross-sectional view along the line IVX-IVX in FIG. 39.

The present embodiment has shown that a plurality of protective members 270 are fixed so as to cover the outer perimeter of the optical fiber 210 along the insertion direction S and at the set interval M.

The present invention is not limited thereto, and as shown in FIG. 39 and FIG. 40, instead of the protective members 270, the outer perimeter of the optical fiber 210 may be covered with a protective tube 241 made of a material having a high heat insulating property, for example, rubber for preventing the optical fiber 210 from contacting the LG 262 or image pickup unit 243 along the insertion direction S.

The protective tube 241 also prevents the optical fiber 210 from contacting the LG 262 or image pickup unit 243 due to warpage of the insertion portion 202 or bending of the bending portion (not shown) provided in the insertion portion 202, and thereby constitutes a reducing member that reduces heat transmitted from the heat generating section such as the image pickup unit 243 or LG 262 to the optical fiber 210 due to contact and reduces the amount of distortion generated due to heat in the FBGs 240 formed in the optical fiber 210. The rest of the configuration is similar to that of the aforementioned present embodiment.

Such a configuration also allows effects similar to those of the aforementioned present embodiment. Although the effect is smaller than that of the configuration shown in FIG. 39 and FIG. 40, only covering the outer perimeter of the optical fiber 210 with the protective tube 241 can reduce heat deformation of the optical fiber 210 due to heat transmitted from the image pickup unit 243 or LG 262.

Furthermore, although the aforementioned embodiment has described a case where the shape of the insertion portion 202 of the endoscope 201 is detected using the optical fiber 210 as an example, the present invention is not limited thereto, but effects similar to those of the present embodiment can be obtained even when the aforementioned shape detection configuration of the insertion portion is applied to any appliance other than an endoscope, for example, the insertion portion of the probe that can be inserted into the tube cavity formed in the endoscope insertion portion as long as such a configuration has an insertion portion to be inserted into a region to be examined and an optical fiber can be inserted into the insertion portion.

In the insertion portion, not only the aforementioned FBGs but also an image pickup unit that picks up an image of the region to be examined and a plurality of light guides (hereinafter referred to as "LG") that supply a light source for illuminating the region to be examined or the like are provided. The image pickup unit and the LG constitute heat generating members that generate heat by being driven and through light guiding.

Here, as is generally known, the optical fiber has the property of becoming deformed such as expansion or contraction with a temperature variation. Since the optical fiber becomes deformed by the amount corresponding to each temperature variation, even a temperature variation in units of 0.1° C., the optical fiber may also be used as a thermometer by detecting the amount of deformation.

Therefore, when the aforementioned heat generating member generates heat by being driven, heat dissipated from the heat generating member in the insertion portion is transmitted to the optical fiber and there is a problem that the optical fiber is deformed for causes other than the deformation of the insertion portion. When the insertion portion is inserted into a high temperature region to be examined, the deformation of the optical fiber occurs even by heat transmitted from the outside of the insertion portion.

As a result, when detecting the shape of the insertion portion by inputting light into the optical fiber and detecting reflected light from the FBG and thereby detecting the amount of distortion of the FBG, the optical fiber is deformed due to heat, that is, the FBG is distorted, which results in a problem that the amount of distortion of the detected FBG does not match the actual amount of deformation of the insertion portion. In other words, there is a problem that the detection accuracy of the insertion portion shape degrades.

The amount of heat generated from the heat generating member also differs depending on the type of endoscope, that is, the influence of heat on the optical fiber also differs depending on the type of endoscope, and therefore there is a problem that the detection accuracy of the shape of the insertion portion differs depending on the type of endoscope.

Hereinafter, an endoscope shape detecting apparatus and an endoscope shape detecting system capable of accurately detecting the shape of the insertion portion according to the type of endoscope will be illustrated using FIG. 41 to FIG. 43.

Figure 41:
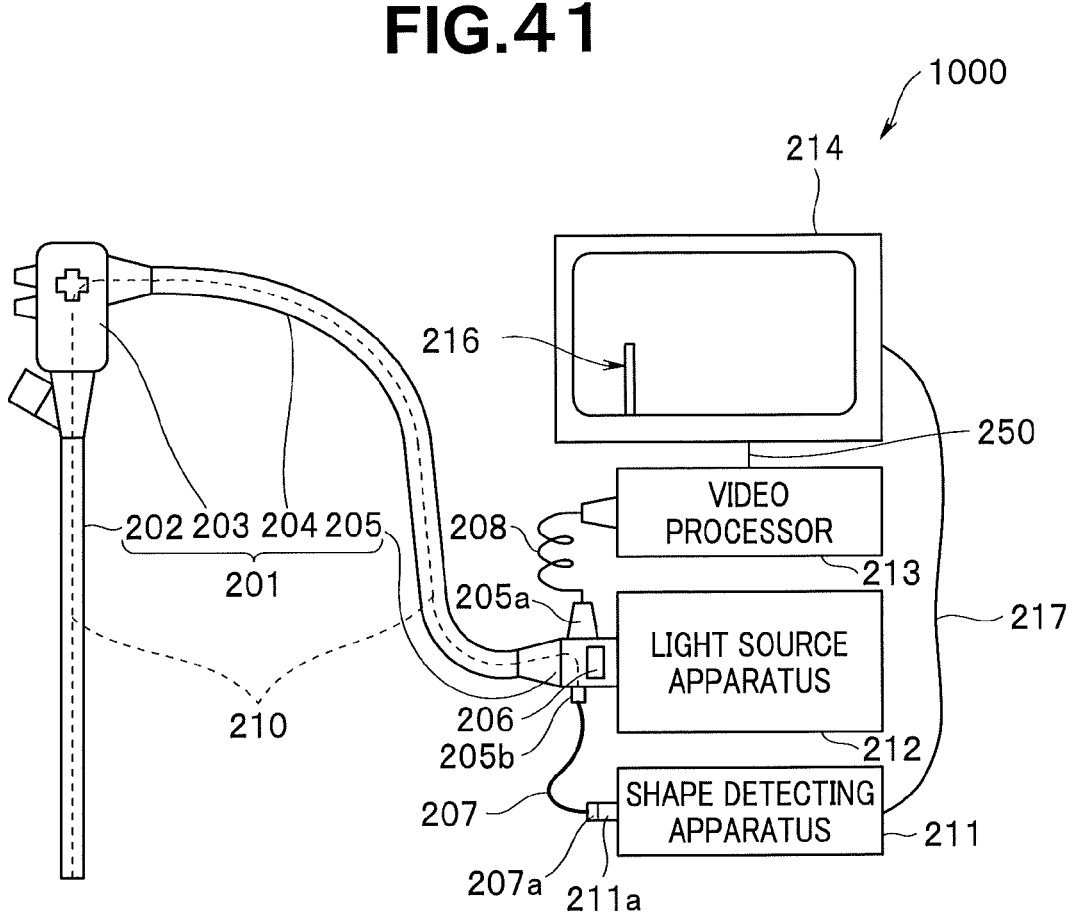
FIG. 41 is a diagram illustrating a shape detecting system of the endoscope.
Figure 42:
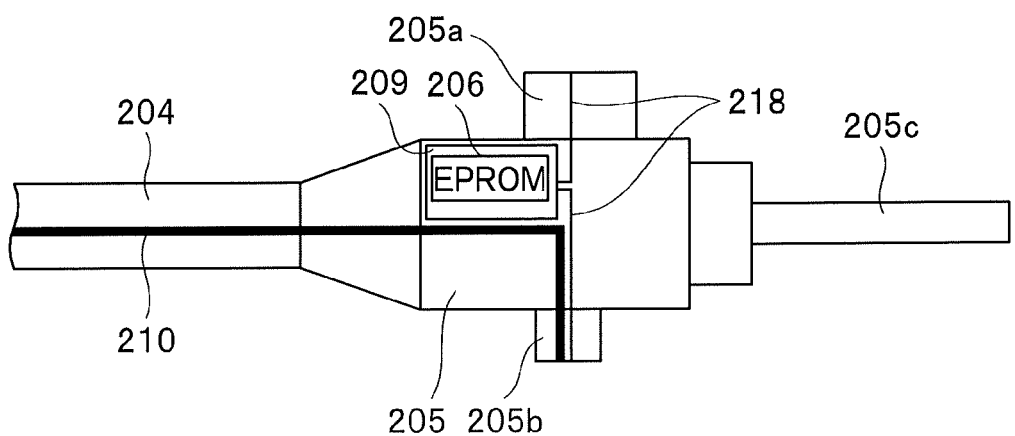
FIG. 42 is an enlarged view schematically illustrating an internal configuration of the endoscope connector in FIG. 41 together with part of a universal cord.
Figure 43:
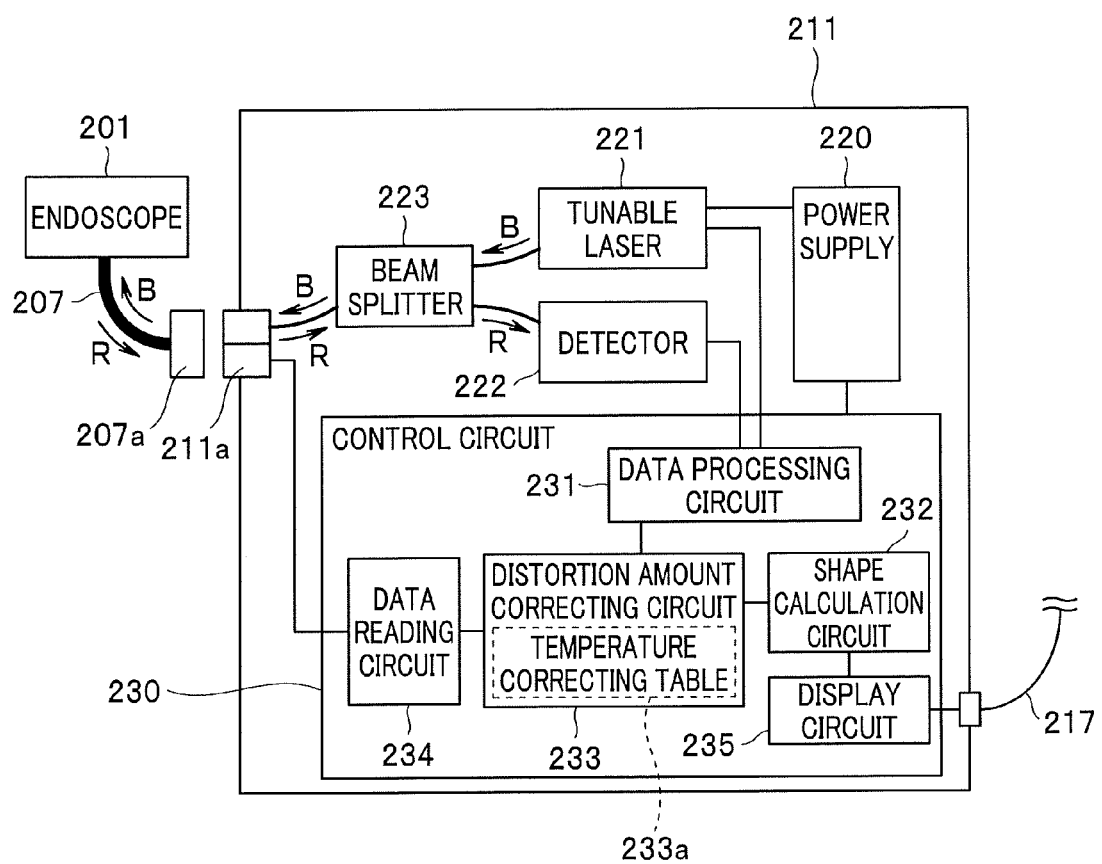
FIG. 43 is a block diagram schematically illustrating a configuration of the shape detecting apparatus in FIG. 41.

FIG. 41 is a diagram illustrating an endoscope shape detecting system, FIG. 42 is an enlarged view schematically illustrating an internal configuration of the endoscope connector in FIG. 41 together with part of a universal cord and FIG. 43 is a block diagram schematically illustrating a configuration of the shape detecting apparatus in FIG. 41.

As shown in FIG. 41, main parts of the shape detecting system 1000 of the endoscope are configured by including an endoscope 201, an endoscope shape detecting apparatus (hereinafter, simply referred to as "shape detecting apparatus") 211, a light source apparatus 212, a video processor 213 and a monitor 214 which is a display section.

Main parts of the endoscope 201 are configured by including an insertion portion 202 to be inserted into a region to be inspected, an operation portion 203 provided on the proximal end side in the insertion direction of the insertion portion 202 (hereinafter, simply referred to as "proximal end side"), a universal cord 204 that extends from the operation portion 203 and an endoscope connector 205 provided at an extending end of the universal cord 204.

Furthermore, an optical fiber 210 for detecting at least the shape of the insertion portion 202 is inserted into the insertion portion 202 of the endoscope 201, the operation portion 203, the universal cord 204 and the endoscope connector 205.

Furthermore, the aforementioned plurality of FBGs (not shown) are formed in the region inserted into at least the insertion portion 202 of the optical fiber 210 along the insertion direction at a set interval. The FBG may also be formed in the regions inserted into the operation portion 203, the universal cord 204 and the endoscope connector 205 of the optical fiber 210.

As shown in FIG. 41, the endoscope connector 205 is connected to the light source apparatus 212 by a connector portion 205c for light source connection provided in the endoscope connector 205 shown in FIG. 42 being attached to the light source apparatus 212.

The endoscope connector 205 incorporates a scope ID substrate 209 provided with an EPROM 206 which is a recording section. A scope ID, which is endoscope information, is recorded in the EPROM 206.

The light source apparatus 212 is intended to supply illumination light, for example, to an LG (not shown) inserted in the endoscope 201. The illumination light supplied to the LG is irradiated onto the region to be inspected from an illumination lens (not shown) provided at the distal end of the LG on the distal end face of the distal end of the insertion portion 202.

Furthermore, the endoscope connector 205 is provided with the connector portion 205a and the connector portion 205a is electrically connected to the video processor 213 via the cable 208. Not only signal lines for communication 218, which will be described later, that extend from the scope ID substrate 209, but also a lead wire for image pickup electrically connected to an image pickup cable (not shown) inserted in the endoscope 201 or the like is inserted in the cable 208

The video processor 213 is intended to perform image pickup control of an image pickup device such as CCD (not shown) provided on the distal end side of the insertion portion 202 via the aforementioned image pickup cable and image pickup lead wire and also perform image processing of an endoscope image picked up by the image pickup device.

Furthermore, the endoscope connector 205 is provided with a connector portion 205b and the connector portion 205b is connected to a connector portion 211a of the shape detecting apparatus 211 via a cable 207. A detachable connector portion 207a provided at an extending end of the cable 207 is detachably attached to the connector portion 211a.

The signal lines for communication 218, which will be described later, extending from the scope ID substrate 209 and the optical fiber 210 or the like are inserted in the cable 207. Furthermore, the extending end of the signal lines for communication 218 and the rear end of the optical fiber 210 are fixed to the detachable connector portion 207a.

The monitor 214 is electrically connected to the video processor 213 via a cable 250 and is also electrically connected to the shape detecting apparatus 211 via a cable 217.

Furthermore, the monitor 214 displays an endoscope image subjected to image processing by the video processor 213 and also displays a scope model 216 displaying the shape of the insertion portion 202 outputted from the shape detecting apparatus 211 or the like.

As shown in FIG. 43, main parts of the shape detecting apparatus 211 are configured by including a power supply 220, a tunable laser 221 which is a light input section, a detector 222, a beam splitter 223 and a control circuit 230.

The power supply 220 is intended to supply power to the tunable laser 221 and the control circuit 230 and the tunable laser 221 which is a wavelength variable laser is intended to input laser light B into the optical fiber 210 from the rear end of the optical fiber 210 via the beam splitter 223, the connector portion 211a and the detachable connector portion 207a.

Furthermore, the detector 222 is intended to detect reflected light R from each FBG of the laser light B inputted to the optical fiber 210 via the detachable connector portion 207a, the connector portion 211a and the beam splitter 223.

Main parts of the control circuit 230 are configured by including a data processing circuit 231 which is an amount of distortion measuring section, a shape calculation circuit 232 which is a shape calculation section, a distortion amount correcting circuit 233 which is an amount of distortion correcting section, a data reading circuit 234 which is a data reading section and a display circuit 235.

The data processing circuit 231 is electrically connected to the tunable laser 221 and the detector 222 and is intended to measure an amount of distortion of each FBG from reflected light R detected by the detector 222.

The distortion amount correcting circuit 233 is electrically connected to the data processing circuit 231 and the data reading circuit 234 and is provided with a temperature correcting table 233a. The temperature correcting table 233a stores information on an optimum amount of correction of the amount of distortion for each FBG position for each combination of parameters having influences on a temperature variation in the insertion portion 202 such as the type of endoscope, operating mode, light amount. Furthermore, the data reading circuit 234 is electrically connected to the connector portion 211a.

The distortion amount correcting circuit 233 is intended to correct the amount of distortion of each FBG measured by the data processing circuit 231 by reading the scope ID recorded in the EPROM 206 via the data reading circuit 234 and looking up the temperature correcting table 233a for each FBG or for the entire optical fiber.

In other words, in consideration of the fact that heat dissipated from the heat generating section such as the image pickup unit that generates heat by being driven or the LG that generates heat through light guiding is transmitted to the optical fiber 210 and the optical fiber 210 is thereby deformed, that is, each FBG is distorted, the distortion amount correcting circuit 233 corrects the amount of distortion of each FBG measured by the data processing circuit 231 into an amount of distortion free of any temperature influence on the FBG based on the scope ID in the EPROM 206 and by looking up the temperature correcting table 233a for each FBG or the entire optical fiber. As for a more specific correction method, the amount of distortion is corrected by detecting the amount of shift from the frequency of light at a certain reference temperature and looking up the temperature correcting table 233a.

The shape calculation circuit 232 is electrically connected to the distortion amount correcting circuit 233 and is intended to calculate the shape of the insertion portion 202 according to the amount of distortion corrected by the distortion amount correcting circuit 233.

The display circuit 235 is electrically connected to the shape calculation circuit 232 and is intended to display the shape of the insertion portion 202 calculated by the shape calculation circuit 232 on the monitor 214 as a scope model 216.

Thus, the present configuration has shown that the distortion amount correcting circuit 233 of the control circuit 230 corrects the amount of distortion of each FBG measured by the data processing circuit 231 based on the scope ID recorded in the EPROM 206 by looking up the temperature correcting table 233a for each FBG or the entire optical fiber.

Thus, even if the amount of heat generated and transmitted from the image pickup unit or LG to the optical fiber 210 differs depending on the type of endoscope, the distortion amount correcting circuit 233 corrects the amount of distortion of each FBG measured by the data processing circuit 231 for each FBG or the entire optical fiber according to the type of endoscope, and can thereby accurately detect the shape of the insertion portion 202.

As described above, it is possible to provide the endoscope shape detecting apparatus 211 and the endoscope shape detecting system 1000 capable of accurately detecting the shape of the insertion portion 202 according to the type of the endoscope 201.

Hereinafter, a modification example will be illustrated.

Although the aforementioned configuration has described a case where the shape of the insertion portion 202 of the endoscope 201 is detected using the optical fiber 210 as an example, the present invention is not limited thereto, but effects similar to those of the present embodiment can be obtained even when the aforementioned shape detection configuration of the insertion portion is applied to any appliance other than an endoscope, for example, the insertion portion of the probe that can be inserted into the tube cavity formed in the endoscope insertion portion as long as such a configuration has an insertion portion to be inserted into a region to be inspected and an optical fiber can be inserted into the insertion portion. Furthermore, the present configuration has shown that the temperature correcting table 233a is provided in the distortion amount correcting circuit 233, but the present invention is not limited thereto and the temperature correcting table 233a may be provided in the EPROM 206.

Eighth Embodiment

The distal end side of the optical fiber disclosed in Japanese Patent Application Laid-Open Publication No. 2004-251779 is fixed inside the distal end side of the insertion portion of the endoscope, to be more specific, to the distal end rigid portion provided inside, via a holder or the like and is thereby inserted in the insertion portion.

Not all light inputted to the optical fiber for detecting the shape of the insertion portion is reflected by the FBG, but part of the light passes through the FBG and is guided to the distal end of the optical fiber. Compared to the configuration of the endoscope shape detecting system according to the seventh embodiment shown in aforementioned FIG. 33 to FIG. 43, the configuration of the endoscope shape detecting system according to the eighth embodiment is different in the shape of a bottomed hole of a holder that fixes the distal end of the optical fiber to the distal end rigid portion. Thus, only the differences will be described and the same components as those in the seventh embodiment will be assigned the same reference numerals and descriptions thereof will be omitted.

Figure 44:
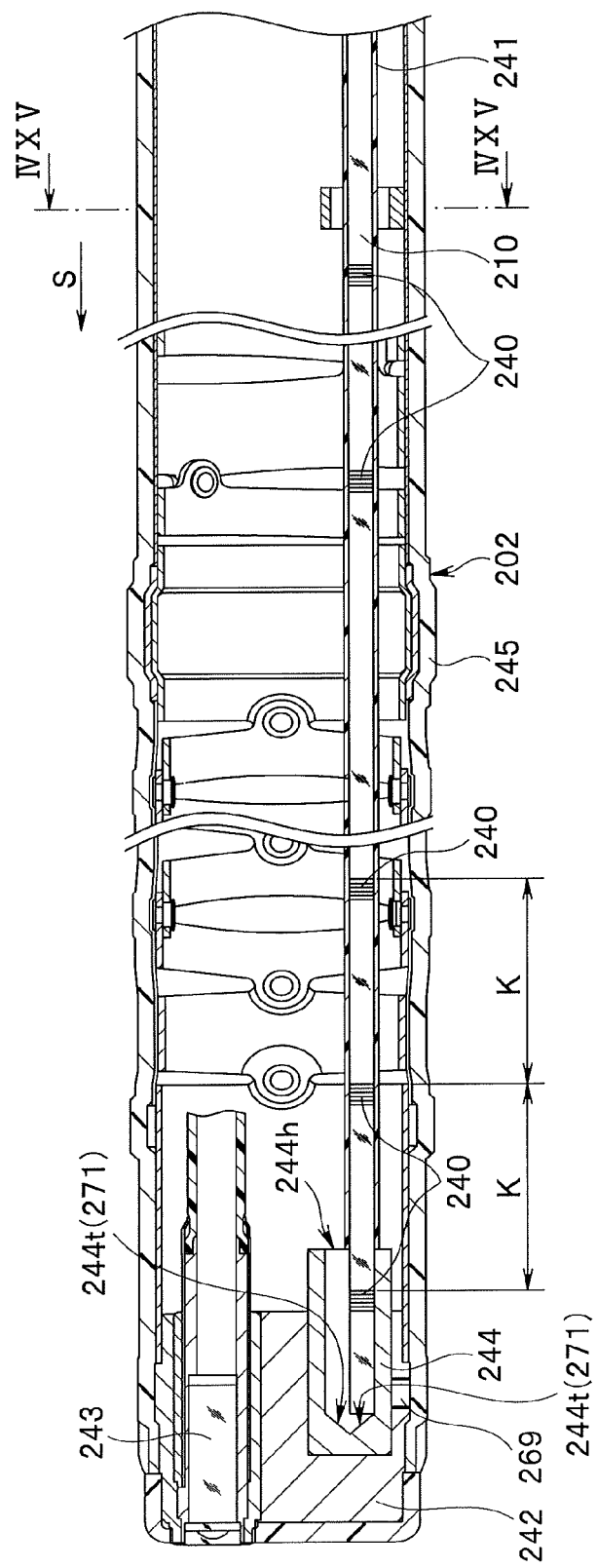
FIG. 44 is a partial cross-sectional view schematically illustrating an internal configuration on the distal end side of the insertion portion of an endoscope illustrating an eighth embodiment.
Figure 45:
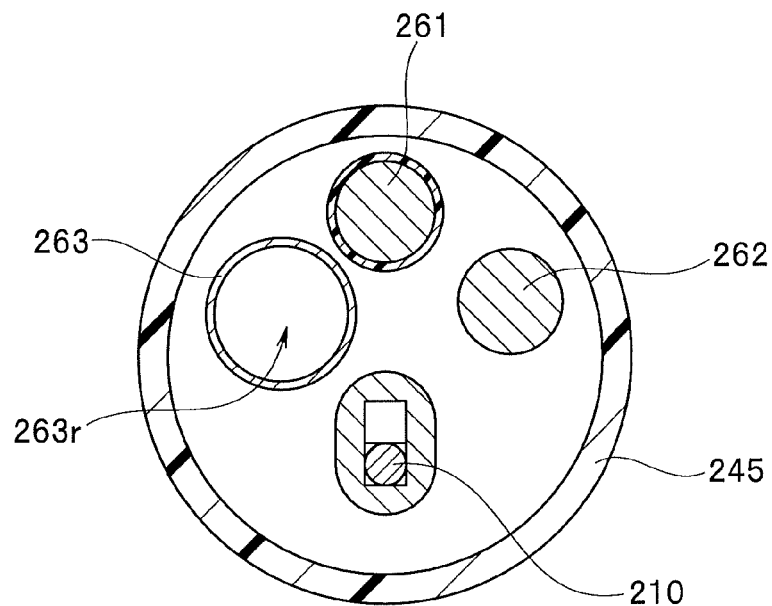
FIG. 45 is a cross-sectional view along the line IVXV-IVXV in FIG. 44.
Figure 46:
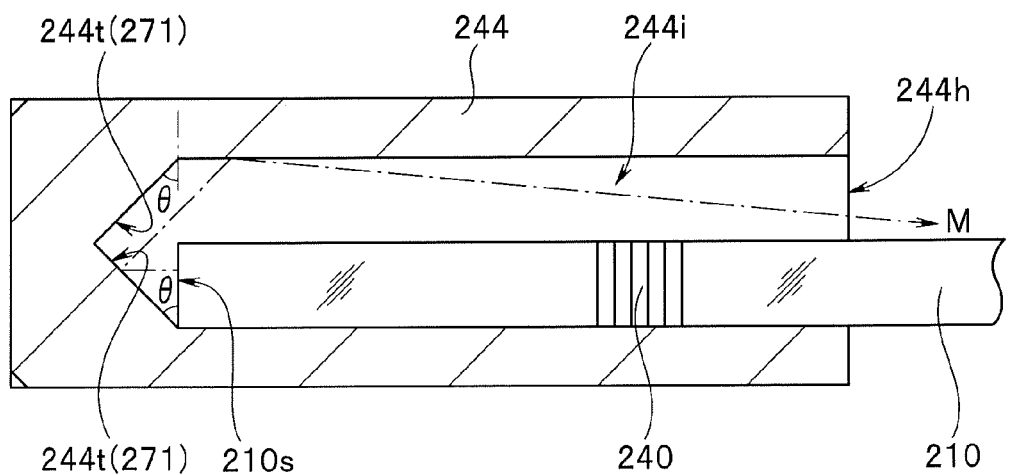
FIG. 46 is a partial enlarged cross-sectional view of a fixing member that fixes the distal end side of the optical fiber in FIG. 44 together with the optical fiber.

FIG. 44 is a partial cross-sectional view schematically illustrating an internal configuration on the distal end side of the insertion portion of an endoscope, FIG. 45 is a cross-sectional view along the line IVXV-IVXV in FIG. 44 and FIG. 46 is a partial enlarged cross-sectional view of a fixing member that fixes the distal end side of the optical fiber in FIG. 44 together with the optical fiber.

As shown in FIG. 44, the optical fiber 210 covered with the protective tube 241 is inserted in the interior of the insertion portion 202 on the distal end side covered with the skin 245 and the distal end side of the optical fiber 210 is fixed to the distal end rigid portion 242 provided inside the distal end of the insertion portion 202 via the holder 244 which is a fixing member. The holder 244 is fixed to the distal end rigid portion 242 by the stopper screw 269 inserted from the outer circumferential direction of the insertion portion 202.

As shown in FIG. 46, a bottomed hole 244i is formed in the holder 244 along the insertion direction S in which the distal end side of the optical fiber 210 is inserted and fixed, and the opening of the bottomed hole 244i provided on the proximal end side of the holder 244 constitutes an exit port 244h through which passing light M of laser light B emitted from the distal end 210s after passing through the FBG 240 of the optical fiber 210 is emitted into the insertion portion 202 from the bottomed hole 244i.

As shown in FIG. 44, the exit port 244h is located closer to the rear end side than the image pickup unit 243 provided in the distal end rigid portion 242, which will be described later. This is intended to prevent the passing light M emitted from the exit port 244h from entering the image pickup unit 243 and thereby prevent image disturbance from generating in an image picked up by the image pickup unit 243.

Returning to FIG. 46, in the bottomed hole 244i of the holder 244, an opposed surface 244t facing the distal end 210s of the optical fiber 210 has a quasi-V-shaped cross section inclined by a set angle θ with respect to the distal end face of the distal end 210s of the optical fiber 210.

Furthermore, a mirror film 271 which is incidence prevention means for guiding the passing light M emitted from the distal end 210s to the outside of the optical fiber 210 is formed in the opposed surface 244t by applying mirror finish to the opposed surface 244t.

Since the mirror film 271 is formed on the opposed surface 244t and the mirror film 271 is also inclined by the set angle θ with respect to the distal end face of the distal end 210s of the optical fiber 210, the mirror film 271 can reflect the passing light M emitted from the distal end 210s in a direction other than that of the distal end 210s. Thus, the mirror film 271 has the function of emitting the passing light M emitted from the distal end 210s to the inside of the insertion portion 202 on the distal end side from the bottomed hole 244i via the exit port 244h.

Furthermore, as shown in FIG. 45, in addition to the optical fiber 210, the image pickup cable 261, the light guide 262, a channel tube 263 or the like including a fluid supply channel 263r formed on the inside are inserted in the interior of the insertion portion 202 covered with the skin 245.

The distal end of the image pickup cable 261 is electrically connected to the image pickup unit 243 provided in the distal end rigid portion 242. Furthermore, the distal end of the light guide 262 is proximate to an illumination lens (not shown) provided in the distal end rigid portion 242, fixed to the distal end rigid portion 242 so as to be opposed thereto and the channel 263r is open to the distal end face of the distal end rigid portion 242.

Other members are inserted and various members are disposed in the interior of the insertion portion 202, but they are well known and descriptions thereof will be omitted.

The present embodiment has shown that in the bottomed hole 244i of the holder 244 which fixes the distal end 210s of the optical fiber 210 to the distal end rigid portion 242, the opposed surface 244t facing the distal end 210s of the optical fiber 210 has a quasi-V-shaped cross section inclined by a set angle θ with respect to the distal end face of the distal end 210s of the optical fiber 210 and the mirror film 271 is formed on the opposed surface 244t.

Furthermore, the present embodiment has also shown that the exit port 244h that emits passing light M from the bottomed hole 244i of the holder 244 to the outside of the holder 244 is formed on the proximal end side of the holder 244.

Thus, as shown in FIG. 46, the passing light M having passed through the FBG 240 and emitted from the distal end 210s of the optical fiber 210 is reflected in a direction other than that of the distal end 210s by the mirror film 271, and the reflected passing light M is emitted from the exit port 244h to the inside of the insertion portion 202, and therefore it is possible to prevent the passing light M emitted from the distal end 210s of the optical fiber 210 from re-entering the optical fiber 210 from the distal end 210s as returning light and thereby prevent the detector 222 from detecting the returning light and erroneously detecting the amount of distortion of the FBG 240. That is, it is possible to prevent the accuracy of shape detection of the insertion portion 202 from degrading.

As described above, by preventing the passing light M emitted from the distal end 210s of the optical fiber 210 from re-entering the optical fiber 210, it is possible to provide an endoscope and an endoscope shape detecting system having a configuration capable of accurately detecting the shape of the insertion portion 202.

Although the present embodiment assumes that the opposed surface 244t of the holder 244 has a quasi-V-shaped cross section, the present invention is not limited thereto, but it goes without saying that the opposed surface 244t can have any shape such as curvature surface as long as it is a shape that causes the transmitted light M to be reflected so that the transmitted light M emitted from the distal end 210s of the optical fiber 210 does not enter the distal end 210s.

Ninth Embodiment

Figure 47:
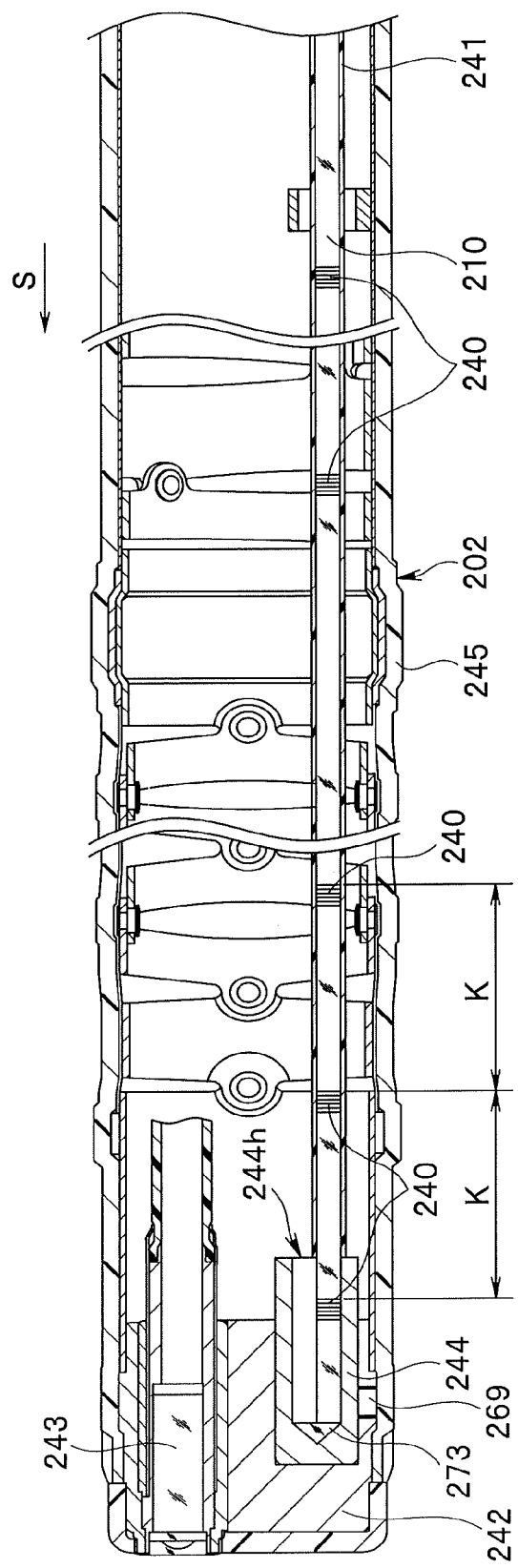
FIG. 47 is a partial cross-sectional view schematically illustrating an internal configuration on the distal end side of the insertion portion of an endoscope illustrating a ninth embodiment.
Figure 48:
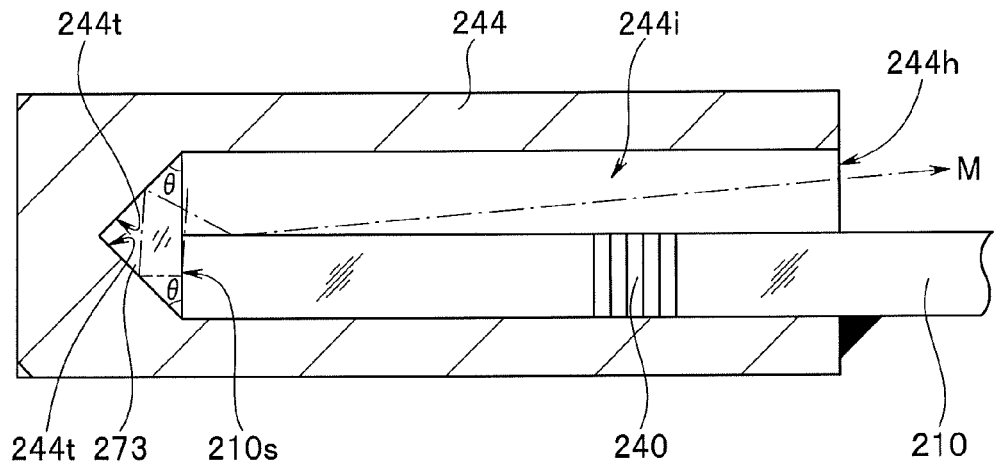
FIG. 48 is a partial enlarged cross-sectional view of the fixing member that fixes the distal end side of the optical fiber in FIG. 47 together with the optical fiber.

FIG. 47 is a partial cross-sectional view schematically illustrating an internal configuration on the distal end side of the insertion portion of an endoscope illustrating a ninth embodiment and FIG. 48 is a partial enlarged cross-sectional view of the fixing member that fixes the distal end side of the optical fiber in FIG. 47 together with the optical fiber.

Compared to the endoscope according to the eighth embodiment shown in FIG. 44 to FIG. 46 above, the configuration of the endoscope according to the ninth embodiment is different in that the incidence prevention means provided in the holder is made up of not a mirror film but a prism. Thus, only the difference will be described and the same components as those in the eighth embodiment will be assigned the same reference numerals and descriptions thereof will be omitted.

As shown in FIG. 47, FIG. 48, in the bottomed hole 244i of the holder 244, the opposed surface 244t facing the distal end 210s of the optical fiber 210 has a quasi-V-shaped cross section inclined by a set angle θ with respect to the distal end face of the distal end 210s of the optical fiber 210 as in the case of the aforementioned eighth embodiment. However, the shape of the opposed surface 244t is not limited to the quasi-V-shaped cross section in the present embodiment, either.

Furthermore, a prism 273 which is incidence prevention means for guiding the passing light M emitted from the distal end 210s to the outside of the optical fiber 210 is provided on the opposed surface 244t. The rest of the configuration is the same as that of the aforementioned eighth embodiment.

In such a configuration, as shown in FIG. 48, the passing light M having passed through the FBG 240 and emitted from the distal end 210s of the optical fiber 210 is reflected in a direction other than that of the distal end 210s by the prism 273 and the reflected passing light M is emitted from the exit port 244h to the inside of the insertion portion 202, and it is thereby possible to prevent the passing light M emitted from the distal end 210s of the optical fiber 210 from re-entering the optical fiber 210 from the distal end 210s as returning light and thereby prevent the detector 222 from detecting the returning light and erroneously detecting the amount of distortion of the FBG 240. That is, it is possible to prevent the accuracy of shape detection of the insertion portion 202 from degrading.

As described above, by preventing the passing light M emitted from the distal end 210s of the optical fiber 210 from re-entering the optical fiber 210, it is possible to provide an endoscope and an endoscope shape detecting system having a configuration capable of accurately detecting the shape of the insertion portion 202.

Tenth Embodiment

Figure 49:
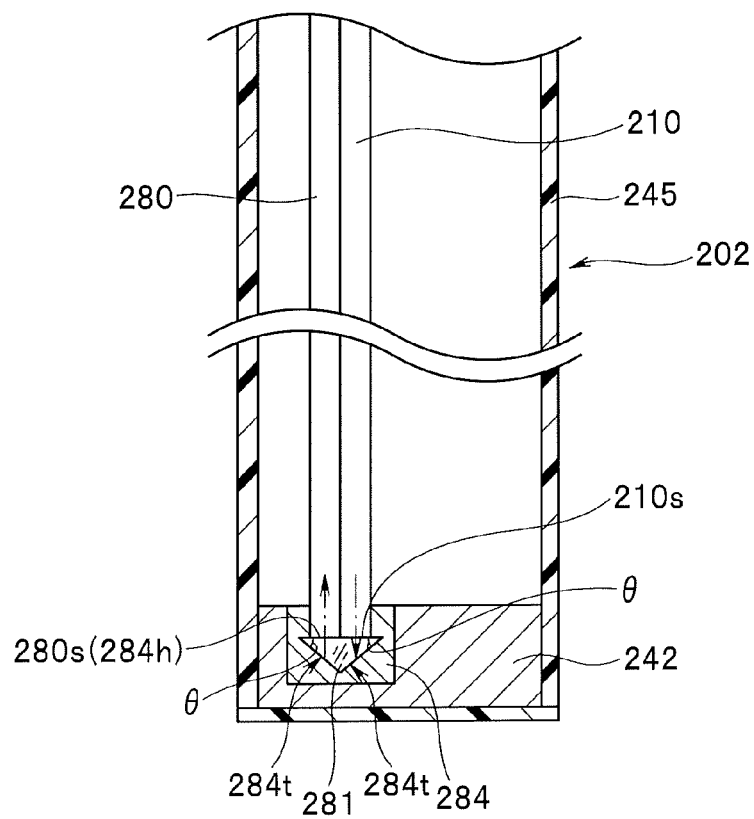
FIG. 49 is a partial cross-sectional view schematically illustrating an internal configuration on the distal end side of the insertion portion of an endoscope illustrating a tenth embodiment.

FIG. 49 is a partial cross-sectional view schematically illustrating an internal configuration on the distal end side of the insertion portion of an endoscope illustrating the present embodiment.

Compared to the endoscope according to the eighth embodiment shown in FIG. 44 to FIG. 46 above and the endoscope according to the ninth embodiment shown in FIG. 47 and FIG. 48, the configuration of the endoscope according to the tenth embodiment is different in that the incidence prevention means provided in the holder is made up of not a mirror film or prism but a reflecting mirror. Thus, only the difference will be described and the same components as those in the eighth and ninth embodiments will be assigned the same reference numerals and descriptions thereof will be omitted.

As shown in FIG. 49, in addition to the optical fiber 210 which is the above described one optical fiber, an optical fiber for returning light (hereinafter, simply referred to as "optical fiber") 280 which is another optical fiber is inserted parallel to the optical fiber 210 in the interior covered with the skin 245 of the insertion portion 202. The proximal end of the optical fiber 280 is left open in the insertion portion 202 or operation portion 203 or the like.

Furthermore, in a bottomed hole (not shown) of the holder 284 which fixes each distal end 210s, 280s of the optical fiber 210, 280 to the distal end rigid portion 242, an opposed surface 284t facing each distal end 210s, 280s of the optical fiber 210, 280 has a quasi-V-shaped cross section inclined by a set angle θ with respect to the distal end face of each distal end 210s, 280s of the optical fiber 210, 280 as in the case of the aforementioned eighth and ninth embodiments. However, the shape of the opposed surface 284t is not limited to the quasi-V-shaped cross section in the present embodiment, either.

Furthermore, a reflecting mirror 281 which is incidence prevention means for guiding the passing light M emitted from the distal end 210s to the outside of the optical fiber 210, specifically to the distal end 280s of the optical fiber 280 via the exit port 284h is provided on the opposed surface 284t. The exit port 284h is located closer to the rear end in the insertion direction S than the image pickup unit 243 in the present embodiment, too. The rest of the configuration is the same as that of the aforementioned eighth embodiment.

In such a configuration, as shown in FIG. 49, the passing light M having passed through the FBG 240 and emitted from the distal end 210s of the optical fiber 210 is reflected in a direction other than that of the distal end 210s by the reflecting mirror 281, and, to be more specific, reflected to the distal end 280s of the optical fiber 280 via the exit port 284h and the reflected passing light M is emitted to the inside of the optical fiber 280 and emitted from the proximal end to the inside of the insertion portion 202 or operation portion 203.

This can prevent the passing light M emitted from the distal end 210s of the optical fiber 210 from re-entering the optical fiber 210 from the distal end 210s as returning light, and thereby prevent the detector 222 from detecting the returning light and erroneously detecting the amount of distortion of the FBG 240. That is, it is possible to prevent the accuracy of detecting the shape of the insertion portion 202 from degrading.

As described above, by preventing the passing light M emitted from the distal end 210s of the optical fiber 210 from re-entering the optical fiber 210, it is possible to provide the endoscope 1 and the endoscope shape detecting system 100 having a configuration capable of accurately detecting the shape of the insertion portion 202.

Hereinafter, modification examples will be illustrated.

The aforementioned eighth to tenth embodiments have described cases where the mirror film 271 is formed on the opposed surface 244t of the holder 244, or the prism 273 is provided on the opposed surface 244t of the holder 244 or the reflecting mirror 281 is provided on the opposed surface 284t of the holder 284 so as to prevent the passing light M emitted from the distal end 210s of the optical fiber 210 from re-entering the distal end 210s of the optical fiber 210.

The present invention is not limited thereto, and even when an outgoing light spreading member is provided on the opposed surface 244t, 284t of the holder 244, 284 or projections and depressions for spreading the passing light M emitted from the distal end 210s of the optical fiber 210 are formed, it is also possible to prevent the passing light M emitted from the distal end 210s from re-entering the distal end 210s of the optical fiber 210 as returning light.

Furthermore, although the aforementioned eighth to tenth embodiments have described a case where the shape of the insertion portion 202 of the endoscope 1 is detected using the optical fiber 210 as an example, the present invention is not limited thereto, but effects similar to those of the present embodiment can be obtained even when the aforementioned shape detection configuration of the insertion portion is applied to any appliance other than an endoscope, for example, the insertion portion of the probe that can be inserted into the tube cavity formed in the endoscope insertion portion as long as such a configuration has an insertion portion to be inserted into a region to be inspected and an optical fiber can be inserted into the insertion portion.

Furthermore, the examples of the incidence prevention means shown in the aforementioned eighth to tenth embodiments are not limited to those described in the eighth to tenth embodiments, but, for example, the position opposed to the distal end of the optical fiber sensor may be painted in black so as to have a configuration in which light emitted from the distal end of the optical fiber sensor is absorbed.

Eleventh Embodiment

Compared to the configuration of the endoscope shape detecting system according to the seventh embodiment shown in aforementioned FIG. 33 to FIG. 43, the configuration of the endoscope shape detecting system according to the eleventh embodiment is different in that the shape detecting apparatus 211 inputs laser light into the optical fiber, detects reflected light R from each FBG of the optical fiber, measures an amount of distortion of each FBG from the detected reflected light, counts the number of times the measured amount of distortion exceeds a first amount of distortion and displays a warning on the monitor when the counted number of times of excess exceeds a set number of times. Thus, only the difference will be described and the same components as those in the seventh embodiment will be assigned the same reference numerals and descriptions thereof will be omitted.

Figure 50:
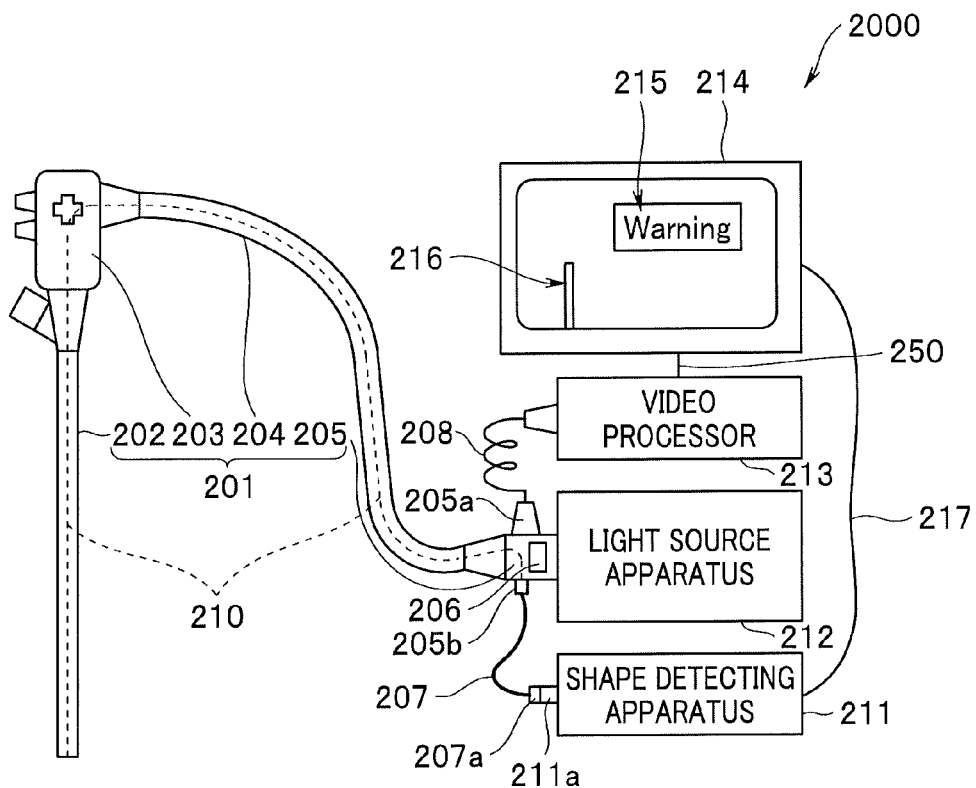
FIG. 50 is a diagram illustrating a shape detecting system of an endoscope illustrating an eleventh embodiment.
Figure 51:
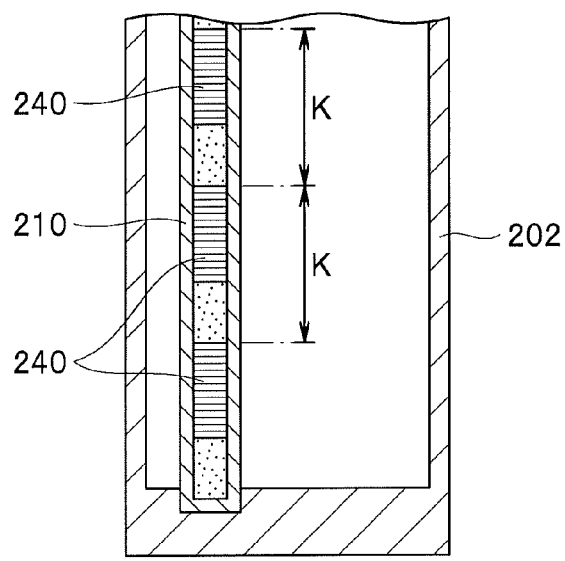
FIG. 51 is a partial enlarged cross-sectional view schematically illustrating an internal configuration on the distal end side of the insertion portion of the endoscope in FIG. 50.
Figure 52:
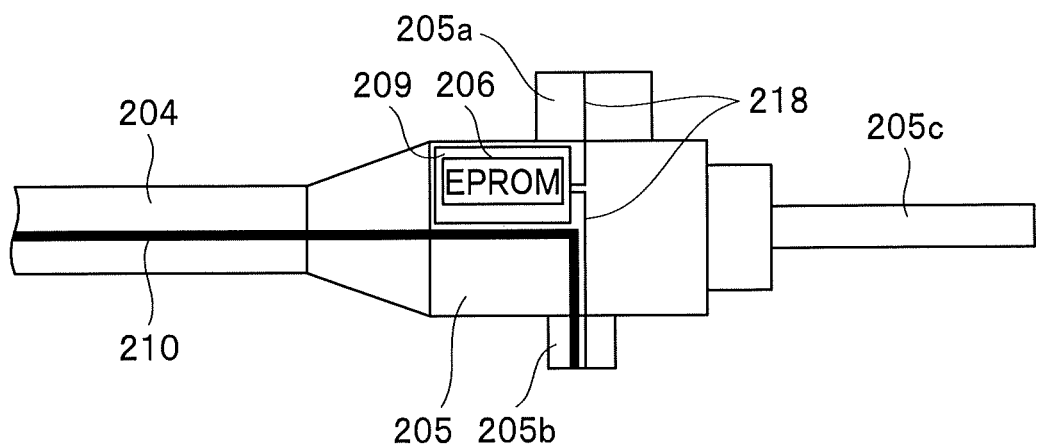
FIG. 52 is an enlarged view schematically illustrating an internal configuration of the endoscope connector in FIG. 50 together with part of the universal cord.

FIG. 50 is a diagram illustrating an endoscope shape detecting system illustrating the present embodiment, FIG. 51 is a partial enlarged cross-sectional view schematically illustrating an internal configuration on the distal end side of the insertion portion of the endoscope in FIG. 50 and FIG. 52 is an enlarged view schematically illustrating an internal configuration of the endoscope connector in FIG. 50 together with part of the universal cord.

As shown in FIG. 50, main parts of the endoscope shape detecting system 2000 are configured by including an endoscope 201, the endoscope shape detecting apparatus (hereinafter, simply referred to as "shape detecting apparatus") 211 which is an optical fiber distortion detecting apparatus, a light source apparatus 212, a video processor 213 and a monitor 214 which is a display section.

Main parts of the endoscope 201 are configured by including an insertion portion 202 which is inserted in a region to be inspected, an operation portion 203 provided on the proximal end side in the insertion direction of the insertion portion 202 (hereinafter, simply referred to as "proximal end side"), a universal cord 204 that extends from the operation portion 203, and an endoscope connector 205 provided at the extending end of the universal cord 204.

An optical fiber 210 for detecting at least the shape of the insertion portion 202 is inserted in the insertion portion 202, the operation portion 203, the universal cord 204 and the endoscope connector 205 of the endoscope 201, with the distal end thereof fixed to the distal end side in the insertion direction of the insertion portion 202 (hereinafter, simply referred to as "distal end side") as shown in FIG. 51.

Furthermore, as shown in FIG. 51, a plurality of aforementioned FBGs 240 are formed in the region inserted at least in the insertion portion 202 of the optical fiber 210 along the insertion direction at a set interval K. The FBG 240 may also be formed in the region inserted in the operation portion 203, the universal cord 204 or the endoscope connector 205 of the optical fiber 210.

As shown in FIG. 50, the endoscope connector 205 is connected to the light source apparatus 212 by a connector portion 205c for light source connection shown in FIG. 52 provided in the endoscope connector 205 being attached to the light source apparatus 212. A scope ID substrate 209 provided with an EPROM 206 which is a recording portion that can write the number of times of excess, which will be described later, is provided in the endoscope connector 205. A scope ID is recorded in the EPROM 206.

The light source apparatus 212 is intended to supply illumination light to, for example, a light guide (not shown) inserted in the endoscope 201. The illumination light supplied to the light guide is irradiated onto the region to be inspected from an illumination lens (not shown) provided at a distal end of the light guide on the distal end face of the distal end of the insertion portion.

Furthermore, the endoscope connector 205 is provided with a connector portion 205a and the connector portion 205a is electrically connected to the video processor 213 via a cable 208. In addition to signal lines for communication 218, which will be described later, that extend from the scope ID substrate 209, an image pickup cable (not shown) inserted in the endoscope 201 or the like is inserted in the cable 208.

The video processor 213 is intended to perform image pickup control of an image pickup device such as CCD (not shown) provided on the distal end side of the insertion portion 202 via the above described image pickup cable and perform image processing or the like on an endoscope image picked up by the image pickup device.

Furthermore, the endoscope connector 205 is provided with a connector portion 205b and the connector portion 205b is connected to a connector portion 211a of the shape detecting apparatus 211 via a cable 207. A detachable connector portion 207a provided at an extending end of the cable 207 is detachably attached to the connector portion 211a.

The signal lines for communication 218 that extend from the scope ID substrate 209 which will be described later, and the optical fiber 210 or the like are inserted in the cable 207. Furthermore, the extending end of the signal lines for communication 218 and the rear end of the optical fiber 210 are fixed to the detachable connector portion 207a.

The monitor 214 is electrically connected to the video processor 213 via a cable 250 and is also electrically connected to the shape detecting apparatus 211 via a cable 217.

Furthermore, the monitor 214 displays not only an endoscope image subjected to image processing by the video processor 213 but also a warning display 215 displaying a warning for the insertion portion 202, which will be described later, and a scope model 216 displaying the shape of the insertion portion 202 outputted from the shape detecting apparatus 211 or the like.

Figure 53:
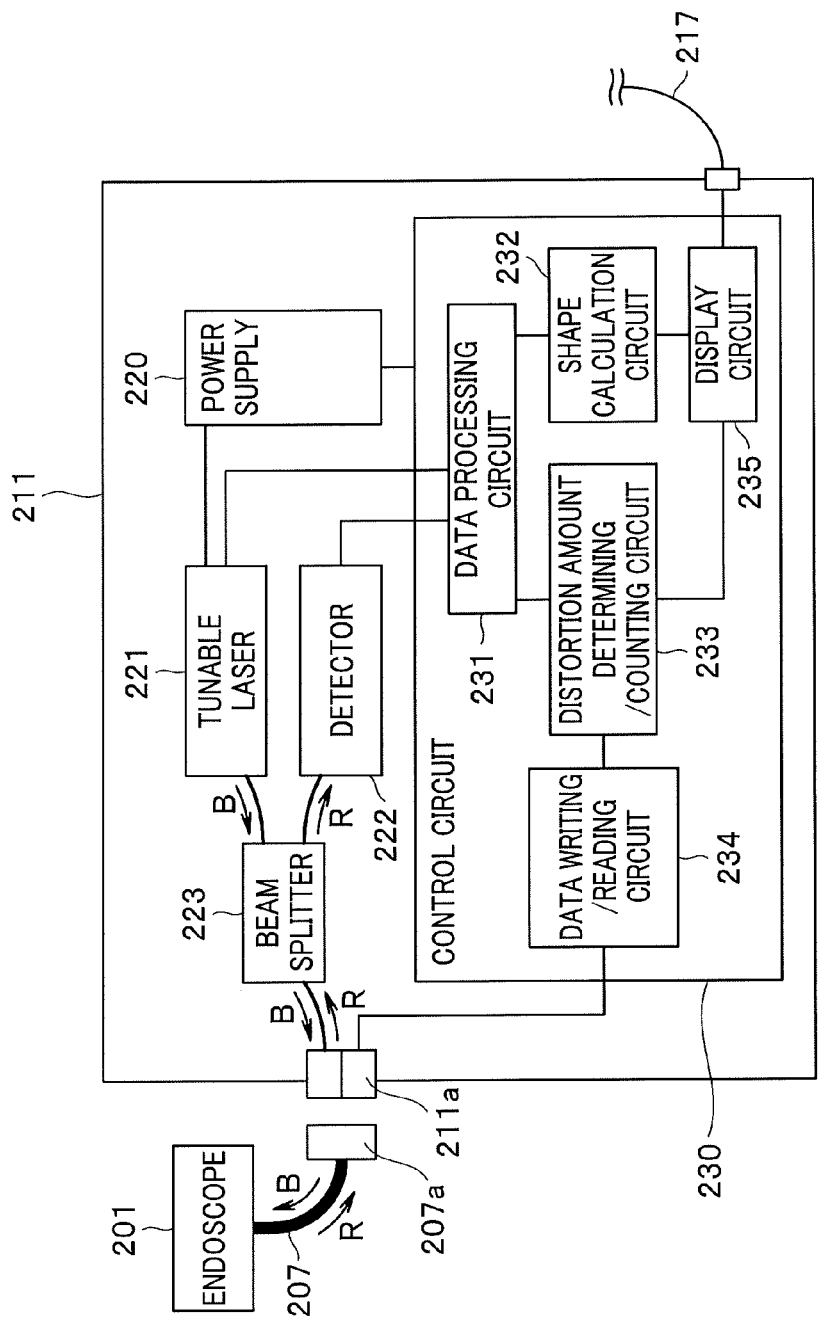
FIG. 53 is a block diagram schematically illustrating a configuration of the shape detecting apparatus in FIG. 50.

Next, the configuration of the shape detecting apparatus 211 will be described using FIG. 53. FIG. 53 is a block diagram schematically illustrating a configuration of the shape detecting apparatus in FIG. 50.

As shown in FIG. 53, main parts of the shape detecting apparatus 211 are configured by including a power supply 220, a tunable laser 221 which is a light input section, a detector 222, a beam splitter 223 and a control circuit 230.

The power supply 220 is intended to supply power to the tunable laser 221 and the control circuit 230 and the tunable laser 221 which is a wavelength variable laser is intended to input laser light B into the optical fiber 210 from the rear end side of the optical fiber 210 via the beam splitter 223, the connector portion 211a and the detachable connector portion 207a.

Furthermore, the detector 222 is intended to detect reflected light R from each FBG 240 of the laser light B inputted to the optical fiber 210 via a detachable connector portion 207a, the connector portion 211a and the beam splitter 223.

Main parts of the control circuit 230 are configured by including a data processing circuit 231 which is an amount of distortion measuring section, a shape calculation circuit 232 which is a shape calculation section, a distortion amount determining/counting circuit 233 which is a determining section and count section, a data reading writing/reading circuit 234 which is a data reading/writing section for performing writing or reading to/from the EPROM 206 and a display circuit 235 which is a warning section.

The data processing circuit 231 is electrically connected to the tunable laser 221 and the detector 222 and is intended to measure an amount of distortion of each FBG 240 from reflected light R detected by the detector 222.

The shape calculation circuit 232 is electrically connected to the data processing circuit 231 and the display circuit 235 and is intended to calculate the shape of the insertion portion 202 from the amount of distortion of each FBG 240 measured by the data processing circuit 231.

The distortion amount determining/counting circuit 233 is electrically connected to the data processing circuit 231, the data reading writing/reading circuit 234 and the display circuit 235 and is intended to determine whether or not the amount of distortion measured by the data processing circuit 231 exceeds a first amount of distortion and count, if the amount of distortion exceeds the first amount of distortion, the number of times of excess. A second amount of distortion is set to an amount of distortion that will not damage the optical fiber 210.

The data reading writing/reading circuit 234 is electrically connected to the connector portion 211a and is intended to either write or read the number of times of excess counted by the distortion amount determining/counting circuit 233 to or from the EPROM 206 via the connector portion 211a, the detachable connector portion 207a and the signal lines for communication 218.

Besides displaying the warning display 215 on the monitor 214 via the cable 217 when the distortion amount determining/counting circuit 233 determines that the number of times of excess is equal to or above a set count, the display circuit 235 is intended to display the shape of the insertion portion 202 calculated by the shape calculation circuit 232 on the monitor 214 as the scope model 216.

Figure 54:
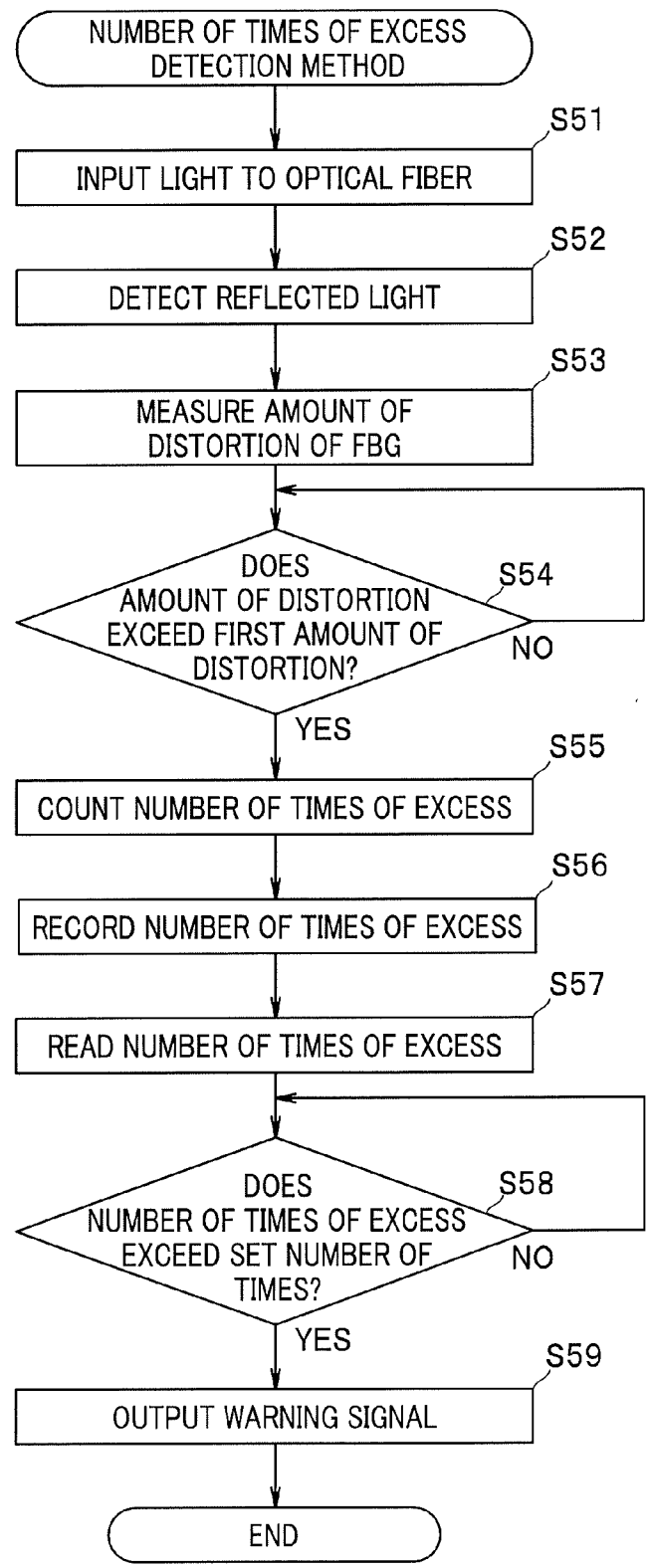
FIG. 54 is a flowchart illustrating a number of times of excess detection method carried out by the shape detecting apparatus in FIG. 50.

Next, the operation of the present embodiment will be described using aforementioned FIG. 53 and FIG. 54. FIG. 54 is a flowchart illustrating the number of times of excess detection method carried out by the shape detecting apparatus in FIG. 50. Since the operation that the shape detecting apparatus 211 displays the shape of the insertion portion 202 on the monitor 214 as the scope model 216 is well known, descriptions thereof will be omitted.

As shown in FIG. 54, in step S51, the laser light B is inputted to the optical fiber 210 from the tunable laser 221 to detect the shape of the insertion portion 202.

Next, in step S52, of the laser light B inputted to the optical fiber 210 from the tunable laser 221, the reflected light R from each FBG 240 formed in the optical fiber 210 is detected by the detector 222.

After that, in step S53, the data processing circuit 231 measures the amount of distortion of each FBG 240 from the reflected light R detected by the detector 222.

Next, in step S54, the distortion amount determining/counting circuit 233 determines whether or not the amount of distortion measured by the data processing circuit 231 has exceeded the first amount of distortion. When the amount of distortion measured by the data processing circuit 231 exceeds the first amount of distortion, the process moves to step S55, where the distortion amount determining/counting circuit 233 counts the number of times of excess.

After that, in step S56, the number of times of excess counted by the distortion amount determining/counting circuit 233 is written to, that is, recorded in, the EPROM 206 by the data reading writing/reading circuit 234 via the connector portion 211a, the detachable connector portion 207a and the signal lines for communication 218.

Next, in step S57, the data reading writing/reading circuit 234 reads the number of times of excess written to the EPROM 206, and in next step S58, the distortion amount determining/counting circuit 233 determines whether or not the number of times of excess has exceeded a set count.

When the number of times of excess exceeds the set count, that is, when the number of times the optical fiber 210 has been bent by an amount greater than a set amount exceeds the set count, the optical fiber 210 is determined to have deteriorated and in step S59, the display circuit 235 outputs a warning signal on the monitor 214 via the cable 217 and displays a warning display 215 on the monitor 214.

Thus, the present embodiment has shown that the shape detecting apparatus 211 inputs laser light B to the optical fiber 210, detects reflected light R from each FBG 240 of the optical fiber 210, measures the amount of distortion of each FBG 240 from the detected reflected light R, counts the number of times the measured amount of distortion exceeds the first amount of distortion and performs a warning display 215 on the monitor 214 when the counted number of times of excess exceeds a set count.

Thus, even when bending stress is repeatedly applied to the insertion portion 202 and the optical fiber 210 is repeatedly bent by a set amount or more and the optical fiber 210 thereby deteriorates, if the optical fiber 210 is bent by the set amount or more and exceeding the set count, a warning display 215 is displayed on the monitor 214 and therefore the operator can easily recognize the deterioration of the optical fiber 210 caused by repeated application of bending stress from the warning display 215.

Thus, since the operator can predict the degree of deterioration and durability of the optical fiber 210, the operator can change the optical fiber 210 before it breaks and can thereby prevent the optical fiber 210 from breaking during inspection causing the inspection to be interrupted.

As described so far, it is possible to provide the shape detecting apparatus 211, the shape detecting system 2000 of the endoscope 201 and the shape detection method of the endoscope 201 having a configuration capable of preventing damages to the optical fiber 210 during use.

Twelfth Embodiment

Figure 55:
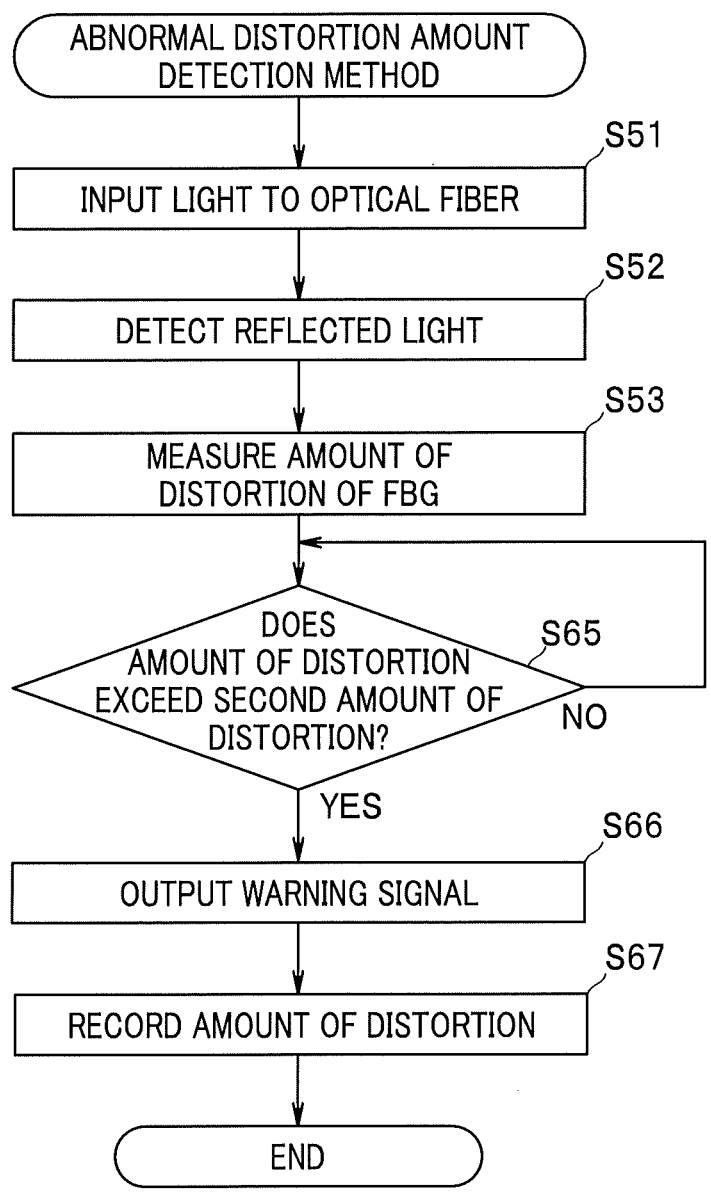
FIG. 55 is a flowchart illustrating an abnormal distortion amount detection method using a shape detecting apparatus according to a twelfth embodiment.

FIG. 55 is a flowchart illustrating an abnormal distortion amount detection method for a shape detecting apparatus according to the present embodiment.

Compared to the shape detecting apparatus according to the eleventh embodiment shown in aforementioned FIG. 50 to FIG. 53, the configuration of the shape detecting apparatus according to the twelfth embodiment is different in that the distortion amount determining/counting circuit 233 not only counts the number of times the measured amount of distortion exceeds a first amount of distortion but also determines whether or not the measured amount of distortion has exceeded a second amount of distortion, that even when the measured amount of distortion exceeds the second amount of distortion, the display circuit 235 outputs a warning signal and that when the second amount of distortion is exceeded, the data reading writing/reading circuit 234 writes the excess amount of distortion to the EPROM 206. The configuration of the endoscope shape detecting system 2000 is similar to that of the aforementioned eleventh embodiment. Thus, only the differences will be described and the same components as those in the eleventh embodiment will be assigned the same reference numerals and descriptions thereof will be omitted.

In the present embodiment, the distortion amount determining/counting circuit 233 has the function of not only determining whether or not the amount of distortion measured by the data processing circuit 231 has exceeded the first amount of distortion and counts the number of times of excess but also determining whether the measured amount of distortion has exceeded the second amount of distortion which is an abnormal amount of distortion. The second amount of distortion may or may not be the same as the first amount of distortion. Furthermore, the second amount of distortion is also set to an amount of distortion that will not damage the optical fiber 210.

Furthermore, the display circuit 235 has the function of not only displaying, when the number of times of excess that the measured amount of distortion has exceeded the first amount of distortion reaches or exceeds a set count, the warning display 215 on the monitor 214, but also displaying the warning display 215 on the monitor 214 every time the measured amount of distortion exceeds the second amount of distortion.

Furthermore, the data reading writing/reading circuit 234 has the function of not only writing or reading the number of times the measured amount of distortion has exceeded the first amount of distortion to or from the EPROM 206, but also writing, when the measured amount of distortion exceeds the second amount of distortion, the exceeded amount of distortion to the EPROM 206.

Next, the operation of the present embodiment will be described using aforementioned FIG. 53 and FIG. 55. The operation shown below is performed simultaneously with step S51 to step S59 in aforementioned FIG. 54.

First, in step S51 to step S53, as in the case of the aforementioned eleventh embodiment, of the laser light B inputted to the optical fiber 210 from the tunable laser 221, the reflected light R from each FBG 240 is detected by the detector 222 and the amount of distortion of each FBG 240 is measured by the data processing circuit 231.

Next, in step S65, the distortion amount determining/counting circuit 233 determines whether or not the measured amount of distortion exceeds the second amount of distortion which is an abnormal amount of distortion. If the measured amount of distortion exceeds the second amount of distortion, that is, when drastic bending stress is applied to the insertion portion 202 and the insertion portion 202 is drastically bent, the process moves to step S66, where the display circuit 235 causes the monitor 214 to display the warning display 215 via the cable 217.

After that, in step S67, the data reading writing/reading circuit 234 writes the amount of distortion that has exceeded the second amount of distortion to the EPROM 206.

Thus, the present embodiment has shown that the shape detecting apparatus 211 displays the warning display 215 on the monitor 214 every time the measured amount of distortion exceeds the second amount of distortion.

Thus, since the operator can easily recognize that drastic bending stress is applied to the optical fiber 210 during use, the operator can prevent continued use the optical fiber 210 without being aware that drastic bending stress is applied to the optical fiber 210 and thus prevent still greater bending stress from applying to the optical fiber 210 during use, causing the optical fiber 210 to be damaged. That is, during use, the operator can easily recognize from the warning display 215 that further bending the optical fiber 210 will damage the optical fiber 210.

As described so far, the present embodiment can also provide the shape detecting apparatus 211, the shape detecting system 2000 of the endoscope 201 and the shape detection method of the endoscope 201 having a configuration capable of preventing damage to the optical fiber 210 during use. The rest of the effects are similar to those of the aforementioned eleventh embodiment.

Hereinafter, modification examples will be described.

Although the aforementioned eleventh and twelfth embodiments have described the case where the shape of the insertion portion 202 of the endoscope 201 is detected using the optical fiber 210 as an example, the present invention is not limited thereto, but it is possible to obtain effects similar to those of the present embodiment even when the shape detection configuration of the aforementioned insertion portion is applied to an appliance other than the endoscope, for example, a probe, as long as such a configuration has an insertion portion inserted in the region to be inspected and allows an optical fiber to be inserted in the insertion portion.

Furthermore, the eleventh and twelfth embodiments have described the case where the shape detecting apparatus 211 displays a warning display 215 on the monitor 214 to inform the operator when the number of times the measured amount of distortion of each FBG 240 has exceeded the first amount of distortion reaches or exceeds a set count or when the measured amount of distortion of each FBG 240 exceeds the second amount of distortion.

Without being limited thereto, however, the shape detecting apparatus 211 may turn on a lamp (not shown) provided in the shape detecting apparatus 211 to give a warning or display warning characters on a monitor (not shown) provided in the shape detecting apparatus 211 or give a warning with voice or by issuing warning sound.

Moreover, there may also be a configuration in which a service person responsible for maintenance may read the number of times of excess or an amount of distortion that has exceeded a second amount of distortion from the EPROM 206 for maintenance instead of giving warning, thereby recognize deterioration of the optical fiber 210 and replace the optical fiber 210.

Furthermore, the present embodiment has described the case where when the measured amount of distortion of each FBG 240 has exceeded the first amount of distortion, the number of times of excess is written to the EPROM 206 provided in the endoscope connector 205 of the endoscope 201 or when the measured amount of distortion of each FBG 240 exceeds the second amount of distortion, the excess amount of distortion is written to the EPROM 206 provided in the endoscope connector 205 of the endoscope 201.

Without being limited thereto, however, it goes without saying that a separate memory may be provided in the shape detecting apparatus 211 and the number of times of excess or the amount of distortion that has exceeded the second amount of distortion may be recorded in the memory for each scope ID of the endoscope 201.

The embodiments of the present invention have been described so far, but the present invention is not limited to the above described embodiments and it goes without saying that various modifications can be made without departing from the spirit and scope of the present invention.

Furthermore, as has been described in detail so far, according to the embodiments of the present invention, it is possible to obtain the following configurations:

(1) A medical instrument including:

distortion detecting means provided with a plurality of distortion detection sections disposed in an insertion body to be inserted into an object to be examined for detecting distortion of the insertion body;

coordinate calculating means for calculating first three-dimensional coordinates of the respective distortion detection sections according to a first three-dimensional coordinate system using a predetermined position as an origin based on the detection result of the distortion detecting means;

coordinate system setting means for setting a second coordinate system based on the first three-dimensional coordinates of the respective distortion detection sections;

coordinate transformation means for transforming the first three-dimensional coordinates of the respective distortion detection sections into second three-dimensional coordinates in a second three-dimensional coordinate system set by the coordinate system setting means; and shape calculating means for calculating a two-dimensional shape of the insertion body based on the second three-dimensional coordinates transformed by the coordinate transformation means.

(2) The medical instrument according to addendum 1, wherein the coordinate system setting means calculates a plane corresponding to the minimum sum of squares of distances from the respective distortion detection sections and sets the second three-dimensional coordinate system based on a center of gravity, a distribution direction and a normal direction of the plane of points of projection of the respective distortion detection sections onto the plane.

(3) The medical instrument according to addendum 2, wherein the coordinate system setting means sets the second three-dimensional coordinate system whose origin is the center of gravity and which has the distribution direction and the normal direction of the plane as axial directions.

(4) The medical instrument according to addendum 1, wherein the insertion body includes gravity detecting means for detecting a direction of gravity, and the coordinate system setting means calculates a plane whose normal is the direction of gravity obtained by the gravity detecting means and sets the coordinate system based on a center of gravity, a distribution direction and the direction of gravity at points of projection of the respective distortion detection sections onto the plane.

(5) The medical instrument according to addendum 4, wherein the coordinate system setting means sets the second three-dimensional coordinate system whose origin is the center of gravity and whose axial directions correspond to the distribution direction and the direction of gravity.

(6) The medical instrument according to any one of addenda 1 to 5, wherein the distortion detecting means is a probe in which three or more distortion detection sections are formed at a predetermined interval and a center point of the three or more distortion detection sections is assumed as the position of the distortion detection section.

(7) The medical instrument according to any one of addenda 1 to 6, wherein the distortion detecting means is a probe having three or more optical fiber sensors in which fiber Bragg grating sensor sections which are the distortion detection sections are formed at the same positions in an axial direction, and distortions of the fiber Bragg grating sensor sections are measured from amounts of wavelength shift of reflected light from the optical fiber sensor.

(8) The medical instrument according to any one of addenda 1 to 7, wherein the insertion body is an insertion portion of the endoscope.

(9) A medical instrument including:

distortion detecting means which is a probe made up of an insertion body to be inserted into an object to be examined provided with a plurality of distortion detection sections for detecting distortion of the insertion body;

coordinate calculating means for calculating first coordinates of the respective distortion detection sections in an arbitrary coordinate system based on the detection results of the distortion detecting means;

reference coordinate system setting means for setting a reference coordinate system whose origin is a predetermined reference point;

coordinate transformation means for transforming the first coordinates in the arbitrary coordinate system calculated by the coordinate calculating means into second coordinates in the reference coordinate system set by the reference coordinate system setting means; and shape calculating means for calculating a shape of the insertion body based on the second coordinates of the respective distortion detection sections.

(10) The medical instrument according to addendum 9, wherein the insertion body is an insertion portion of the endoscope having an operation portion provided with movement sensors, and the reference point is an initial position of the movement sensor.

(11) The medical instrument according to addendum 10, wherein the movement sensors are an acceleration sensor and a gyroscope.

(12) The medical instrument according to addendum 9, further including magnetic field generating means for generating a magnetic field, wherein the insertion body is an insertion portion of the endoscope having an operation portion provided with a magnetic field sensor, and the reference point is the position of the magnetic field generating means.

(13) The medical instrument according to addendum 9, further comprising:

a first sensor probe disposed in the insertion body having the plurality of distortion detection sections;

a second sensor probe provided with a plurality of the distortion detection sections having a marker portion, at an end of which at least the three distortion detection sections are disposed; and a main unit to which an end on a proximal end portion side of the first sensor probe and an end of the second sensor probe which is different from the end provided with the marker portion are connected, wherein the reference point is located on a plane including the three distortion detection sections disposed in the marker portion are connected.

(14) The medical instrument according to addendum 13, wherein the marker portion is disposed on an outer surface of the object to be examined.

(15) The medical instrument according to addendum 13, wherein the marker portion is disposed on an inspection stand on which the object to be examined lies.

(16) A medical instrument including:

a first sensor probe which is distortion detecting means disposed in an insertion body to be inserted into an object to be examined having a plurality of the distortion detection sections for measuring distortion of the insertion body disposed in the insertion body;

a second sensor probe provided with a plurality of the distortion detection sections, at an end of which a marker portion provided with the one or more distortion detection sections are disposed;

a main unit to which an end of a proximal end of the first sensor probe and an end of the second sensor probe which is different from the end provided with the marker portion are connected;

shape calculating means for calculating a shape of the insertion portion based on coordinates of the respective distortion detection sections; and display means for displaying the shape of the insertion portion and the position of the marker portion.

(17) The medical instrument according to any one of addenda 9 to 16, wherein in the probe in which three or more distortion detection sections are formed at a predetermined interval, a center point of the three or more distortion detection sections is assumed as the position of the distortion detection sections.

(18) The medical instrument according to addendum 17, wherein the probe is a probe in which the fiber Bragg grating sensor sections are formed at the same positions of the three or more optical fiber sensors in the axial direction, and distortion of the insertion body is measured from an amount of wavelength shift of reflected light from the optical fiber sensor.

(19) An endoscope provided with an insertion portion to be inserted into a region to be inspected, including:

an optical fiber inserted in the insertion portion;

a fiber Bragg grating formed for the optical fiber;

a heat generating member provided in the insertion portion; and a reducing member provided in the insertion portion that reduces an amount of distortion generated in the fiber Bragg grating due to heat dissipated from the heat generating member and transmitted to the optical fiber.

(20) The endoscope according to addendum 19, further including a fixing member that fixes a distal end in an insertion direction of the optical fiber to an inside on the distal end side in the insertion direction of the insertion portion.

(21) The endoscope according to addendum 20, wherein the reducing member is the fixing member formed of a material of low thermal conductivity.

(22) The endoscope according to any one of addenda 19 to 21, wherein the reducing member is a support member provided on the inner surface of the insertion portion that supports the optical fiber so as to prevent the optical fiber from contacting the heat generating member.

(23) The endoscope according to addendum 22, wherein a plurality of the fiber Bragg gratings are formed in the optical fiber at a set interval in the insertion direction of the insertion portion, and the support member supports positions avoiding the fiber Bragg gratings.

(24) The endoscope according to any one of addenda 19 to 23, wherein the reducing member is protective tube covering an outer perimeter of the optical fiber along the insertion direction of the insertion portion so as to prevent the optical fiber from contacting the heat generating member.

(25) The endoscope according to any one of addenda 19 to 23, wherein the reducing member is a protective member covering an outer perimeter of the optical fiber along the insertion direction of the insertion portion at a set interval so as to prevent the optical fiber from contacting the heat generating member.

(26) The endoscope according to addendum 25, wherein a plurality of the fiber Bragg gratings are formed in the optical fiber at a set interval in the insertion direction, and the protective member covers positions avoiding the fiber Bragg gratings.

(27) The endoscope according to any one of addenda 19 to 26, wherein the heat generating member is an illumination unit for illuminating or guiding light to the region to be inspected.

(28) The endoscope according to any one of addenda 19 to 27, wherein the heat generating member is an image pickup unit that picks up an image of the region to be inspected.

(29) An endoscope shape detecting system, including:
the endoscope according to any one of addenda 19 to 28; and
a shape detecting apparatus that detects at least the shape of the insertion portion.

(30) The endoscope shape detecting system according to addendum 29, wherein the shape detecting apparatus includes:
a light inputting section that inputs light to the optical fiber inserted in at least the insertion portion;
a detector that detects reflected light from the fiber Bragg grating of the light inputted to the optical fiber from the light inputting section;
an amount of distortion measuring section that measures an amount of distortion of the fiber Bragg grating from the reflected light detected by the detector; and
a shape calculation section that calculates the shape of at least the insertion portion according to the amount of distortion measured by the amount of distortion measuring section.

(31) A probe provided with an insertion portion to be inserted into a region to be inspected, including:
an optical fiber inserted in the insertion portion;
a fiber Bragg grating formed in the optical fiber;
a heat generating member provided in the insertion portion; and
a reducing member provided in the insertion portion that reduces an amount of distortion generated in the fiber Bragg grating due to heat dissipated from the heat generating member and transmitted to the optical fiber.

(32) The probe according to addendum 31, further including a fixing member that fixes a distal end in an insertion direction of the optical fiber to an inside on the distal end side in the insertion direction of the insertion portion.

(33) The probe according to addendum 32, wherein the reducing member is the fixing member formed of a material of low thermal conductivity.

(34) The probe according to any one of addenda 31 to 33, wherein the reducing member is a support member provided on the inner surface of the insertion portion that supports the optical fiber so as to prevent the optical fiber from contacting the heat generating member.

(35) The probe according to addendum 34, wherein a plurality of the fiber Bragg gratings are formed in the optical fiber in at a set interval along the insertion direction of the insertion portion, and the support member supports positions avoiding the fiber Bragg gratings.

(36) The probe according to any one of addenda 31 to 35, wherein the reducing member is a protective tube covering an outer perimeter of the optical fiber along the insertion direction of the insertion portion so as to prevent the optical fiber from contacting the heat generating member.

(37) The probe according to any one of addenda 31 to 35, wherein the reducing member is a protective member covering an outer perimeter of the optical fiber along the insertion direction of the insertion portion at a set interval so as to prevent the optical fiber from contacting the heat generating member.

(38) The probe according to addendum 37, wherein a plurality of the fiber Bragg gratings are formed in the optical fiber at a set interval in the insertion direction, and the protective member covers positions avoiding the fiber Bragg gratings.

(39) A probe shape detecting system, including:
the probe according to any one of addenda 31 to 38; and
a shape detecting apparatus that detects the shape of at least the insertion portion.

(40) The probe shape detecting system according to addendum 39, wherein the shape detecting apparatus includes:
a light inputting section that inputs light to the optical fiber inserted in at least the insertion portion;
a detector that detects reflected light from the fiber Bragg grating of the light inputted to the optical fiber from the light inputting section;
an amount of distortion measuring section that measures an amount of distortion of the fiber Bragg grating from the reflected light detected by the detector; and
a shape calculation section that calculates the shape of at least the insertion portion according to the amount of distortion measured by the amount of distortion measuring section.

(41) An endoscope shape detecting apparatus provided with an insertion portion to be inserted into a region to be inspected, including:
a light inputting section that inputs light to an optical fiber inserted in at least the insertion portion;
a detector that detects reflected light from a fiber Bragg grating formed in the optical fiber of the light inputted to the optical fiber from the light inputting section;

an amount of distortion measuring section that measures an amount of distortion of the fiber Bragg grating from the reflected light detected by the detector; and an amount of distortion correcting section that corrects the amount of distortion measured by the amount of distortion measuring section based on endoscope information recorded in a recording section.

(42) The endoscope shape detecting apparatus according to addendum 41, further including a shape calculation section that calculates at least the shape of the insertion portion according to the amount of distortion corrected by the amount of distortion correcting section.

(43) The endoscope shape detecting apparatus according to addendum 41 or 42, further including a data reading section that reads the endoscope information recorded in the recording section.

(44) An endoscope shape detecting system including:
the endoscope shape detecting apparatus according to any one of addenda 41 to 43; and
the endo scope provided with the insertion portion to be inserted into the region to be inspected.

(45) The endoscope shape detecting system according to addendum 44, wherein a plurality of the fiber Bragg gratings are formed in the optical fiber at a set interval.

(46) The endoscope shape detecting system according to addendum 44 or 45, further including a display section that displays at least the shape of the insertion portion.

(47) The endoscope shape detecting system according to any one of addenda 44 to 46,
wherein the recording section is provided in the endoscope.

(48) An endoscope provided with an insertion portion to be inserted into a region to be inspected, including:
an optical fiber inserted in the insertion portion;
a fiber Bragg grating formed for the optical fiber;
a fixing member that fixes a distal end in an insertion direction of the insertion portion of the optical fiber to an inside on the distal end side in the insertion direction of the insertion portion; and
a light guiding section provided in the fixing member for guiding light which passes through the fiber Bragg grating and is emitted from the distal end of the optical fiber to the outside of the optical fiber that has emitted the light.

(49) The endoscope according to addendum 48, wherein a plurality of the fiber Bragg gratings are formed in the insertion direction of the optical fiber at a set interval.

(50) The endoscope according to addendum 48 or 49, wherein an image pickup unit that picks up an image of the region to be inspected is provided in the interior on the distal end side of the insertion portion, and
an exit port of the light guided to the light guiding section in the fixing member is located closer to the rear end side in the insertion direction than the image pickup unit.

(51) The endoscope according to any one of addenda 48 to 50, wherein an opposed surface facing the distal end of the optical fiber of the fixing member has a shape inclined at a set angle with respect to the distal end of the optical fiber, and
the light guiding section is made up of a mirror film formed on the opposed surface by mirror-finishing the opposed position.

(52) The endoscope according to any one of addenda 48 to 50, wherein the light guiding section is a prism provided on the surface opposed to the distal end of the optical fiber of the fixing member.

(53) The endoscope according to any one of addenda 48 to 50, wherein a separate optical fiber is inserted in the insertion portion in addition to the optical fiber, and the light guiding section is a reflecting mirror provided on a surface opposed to the each distal end of two optical fibers of the fixing member that guides light emitted from the distal end of the one optical fiber to the distal end of the other optical fiber.

(54) An endoscope shape detecting system including:
the endoscope according to any one of addenda 48 to 53; and
a shape detecting apparatus that detects the shape of the insertion portion.

(55) The endoscope shape detecting system according to addendum 54, wherein the shape detecting apparatus includes:
a light inputting section that inputs the light to the optical fiber inserted in the insertion portion;
a detector that detects reflected light from the fiber Bragg grating of the light inputted to the optical fiber from the light inputting section;
an amount of distortion measuring section that measures an amount of distortion of the fiber Bragg grating from the reflected light detected by the detector; and
a shape calculation section that calculates the shape of the insertion portion according to the amount of distortion measured by the amount of distortion measuring section.

(56) A probe provided with an insertion portion to be inserted into a region to be inspected, including:
an optical fiber inserted in the insertion portion;
a fiber Bragg grating formed for the optical fiber;
a fixing member that fixes a distal end in an insertion direction of the insertion portion of the optical fiber to an inside on the distal end side in the insertion direction of the insertion portion; and
a light guiding section provided in the fixing member for guiding light which passes through the fiber Bragg grating and is emitted from the distal end of the optical fiber to an outside of the optical fiber that has emitted the light.

(57) The probe according to addendum 56, wherein the insertion portion of the probe can be inserted into the tube cavity formed in the insertion portion of the endoscope.

(58) A probe shape detecting system including:
the probe according to addendum 56 or 57; and
a shape detecting apparatus that detects a shape of the insertion portion.

(59) The probe shape detecting system according to addendum 58, wherein the shape detecting apparatus includes:
a light inputting section that inputs the light to the optical fiber inserted in the insertion portion;
a detector that detects reflected light from the fiber Bragg grating of the light inputted to the optical fiber from the light inputting section;
an amount of distortion measuring section that measures an amount of distortion of the fiber Bragg grating from the reflected light detected by the detector; and
a shape calculation section that calculates the shape of the insertion portion according to the amount of distortion measured by the amount of distortion measuring section.

(60) An optical fiber distortion detecting apparatus including:
a light inputting section that inputs light to an optical fiber provided in an insertion portion that can be inserted into a region to be inspected in which a fiber Bragg grating is formed;
a detector that detects reflected light from the fiber Bragg grating formed in the optical fiber of the light inputted to the optical fiber from the light inputting section;
an amount of distortion measuring section that measures an amount of distortion of the fiber Bragg grating from the reflected light detected by the detector;

a determining section that determines whether or not the amount of distortion measured by the amount of distortion measuring section exceeds a first amount of distortion and counts, in the case of excess, the number of times of excess; and a warning section that issues a warning when the number of times of excess reaches or exceeds a set count.

(61) The optical fiber distortion detecting apparatus according to addendum 60, wherein the determining section further determines whether the amount of distortion measured by the amount of distortion measuring section exceeds a second amount of distortion and the warning section issues a warning when the amount of distortion exceeds the second amount of distortion.

(62) The optical fiber distortion detecting apparatus according to addendum 60 or 61, further including:

a recording section to which the number of times of excess can be written; and a data reading/writing section that performs writing or reading to/from the recording section.

(63) The optical fiber distortion detecting apparatus according to addendum 62, wherein the data reading/writing section writes, when the amount of distortion exceeds the second amount of distortion, the measured amount of distortion to the recording section.

(64) The optical fiber distortion detecting apparatus according to addenda 60 to 63, further including a shape calculation section that calculates a shape of the insertion portion according to the amount of distortion measured by the amount of distortion measuring section.

(65) A medical instrument shape detecting system including:

the optical fiber distortion detecting apparatus according to any one of addenda 60 to 64; and a medical instrument provided with the insertion portion.

(66) The medical instrument shape detecting system according to addendum 65, wherein a plurality of the fiber Bragg gratings are formed in the optical fiber at a set interval.

(67) The medical instrument shape detecting system according to any one of addenda 65 or 67, further including a display section that displays a warning by the warning section and displays a shape of the insertion portion.

(68) The medical instrument shape detecting system according to any one of addenda 65 to 67, wherein the recording section is provided in the endoscope.

(69) An optical fiber distortion detection method for detecting distortion of an optical fiber in which a fiber Bragg grating is formed, including:

a step of inputting light from a light inputting section to the optical fiber;

a step of detecting reflected light from the fiber Bragg grating formed in the optical fiber of the light inputted from the light inputting section to the optical fiber using a detector;

a step of an amount of distortion measuring section measuring an amount of distortion of the fiber Bragg grating from the reflected light detected by the detector;

a step of a determining section determining whether or not the amount of distortion measured by the amount of distortion measuring section exceeds a first amount of distortion and the determining section counting the number of times of excess in the case of excess; and a step of a warning section issuing a warning when the number of times of excess reaches or exceeds a set count.

(70) The optical fiber distortion detection method according to addendum 69, further including:

a step of the determining section determining whether or not the amount of distortion measured by the amount of distortion measuring section exceeds a second amount of distortion; and a step of the warning section issuing a warning when the amount of distortion exceeds the second amount of distortion.

(71) The optical fiber distortion detection method according to addendum 69 or 70, further including a step of a data reading/writing section writing the number of times of excess to a writable recording section or reading the number of times of excess from the recording section.

(72) The optical fiber distortion detection method according to addendum 71, further including a step of the data reading/writing section writing, when the amount of distortion exceeds the second amount of distortion, the measured amount of distortion to the recording section.

What is claimed is:

1. A medical instrument comprising:
an operation portion provided with a movement sensor and a switch;
an insertion body to be inserted into an interior of an object to be examined, the insertion body being connected to the operation portion;
a distortion detection unit disposed in the insertion body in which a plurality of distortion detection sections for detecting distortion of the insertion body are formed;
a coordinate calculation unit that calculates first coordinates of the respective distortion detection sections using any one of the plurality of distortion detection sections as a reference point in a first coordinate system defined by a correlation between the reference point and the distortion detection sections;
a reference coordinate system setting unit that sets a second coordinate system having a reference point and axial direction based on a position and an orientation of the movement sensor when the switch is pressed;
a coordinate transformation unit that transforms the first three-dimensional coordinates of the respective distortion detection sections to second three-dimensional coordinates in the second coordinate system set by the coordinate system setting unit based on a relative positional relationship between the reference point set by the reference coordinate system setting unit and the reference point set by the first coordinate system; and
a display unit that displays a shape of the insertion body based on the second coordinates transformed by the coordinate transformation unit.

2. The medical instrument according to claim 1, wherein the insertion body is an insertion portion of an endoscope.

3. The medical instrument according to claim 1, wherein the distortion detection unit is a probe in which three or more of the distortion detection sections are formed at a predetermined interval and a center point of the three or more of the distortion detection sections is assumed as a position of the distortion detection sections.

4. The medical instrument according to claim 1, wherein the distortion detecting unit is a probe having three or more optical fiber sensors in which fiber Bragg grating sensor sections which are the distortion detection sections are formed at the same positions in an axial direction and the medical instrument further comprises:
a light inputting section provided in the insertion body that inputs light to the optical fiber sensor;
a detector that detects reflected light from the fiber Bragg grating sensor section formed in the optical fiber of the light inputted to the optical fiber sensor from the light inputting section; and an amount of distortion measuring section that measures distortion of the fiber Bragg grating sensor section based on the amount of wavelength shift of the reflected light from the optical fiber sensor detected by the detector.

5. The medical instrument according to claim 4, further comprising an incidence prevention unit that prevents the light impinged from the light inputting section, having passed through the fiber Bragg grating sensor section and emitted from the distal end of the optical fiber sensor from impinging on the distal end of the optical fiber sensor.

6. The medical instrument according to claim 4, further comprising:
- a heat generating member provided in the insertion body; and
- a reducing member provided in the insertion body that reduces an amount of distortion generated in the fiber Bragg grating sensor section due to heat dissipated from the heat generating member and transmitted to the optical fiber sensor.

7. The medical instrument according to claim 4, further comprising:
- a determining section that determines whether or not the amount of distortion of the fiber Bragg grating sensor measured by the amount of distortion measuring section exceeds a first amount of distortion;
- a count section that counts, when the amount of distortion of the fiber Bragg grating sensor exceeds the first amount of distortion, the number of times of excess; and
- a warning section that issues a warning when the number of times of excess reaches or exceeds a set count.

8. The medical instrument according to claim 1, wherein the movement sensor comprises a gyroscope and an acceleration sensor.

9. The medical instrument according to claim 1, wherein the reference coordinate system setting unit resets the second coordinate system each time the switch is pressed.

10. The medical instrument according to claim 9, wherein the reference point of the second coordinate system is one point a first time the switch is pressed and is a second point the second time the switch is pressed.

* * * * *